(12) United States Patent
Shaikh et al.

(10) Patent No.: US 10,463,391 B2
(45) Date of Patent: *Nov. 5, 2019

(54) MAGNETIC FERROCENYL-FUNCTIONALIZED NANOPARTICLE

(71) Applicant: KING FAHD UNIVERSITY OF PETROLEUM AND MINERALS, Dhahran (SA)

(72) Inventors: M. Nasiruzzaman Shaikh, Dhahran (SA); Md. Abdul Aziz, Dhahran (SA); Aasif Helal, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/151,471

(22) Filed: Oct. 4, 2018

(65) Prior Publication Data
US 2019/0029718 A1 Jan. 31, 2019

Related U.S. Application Data

(63) Continuation of application No. 15/610,269, filed on May 31, 2017, now Pat. No. 10,125,159.

(60) Provisional application No. 62/406,449, filed on Oct. 11, 2016.

(51) Int. Cl.
| A61B 17/32 | (2006.01) |
| A61B 17/3207 | (2006.01) |
| A61B 17/22 | (2006.01) |
| A61B 17/00 | (2006.01) |

(52) U.S. Cl.
CPC ...... *A61B 17/320758* (2013.01); *A61B 17/22* (2013.01); *A61B 2017/00734* (2013.01); *A61B 2017/22038* (2013.01); *A61B 2017/22079* (2013.01); *A61B 2017/320775* (2013.01); *A61B 2217/005* (2013.01)

(58) Field of Classification Search
None
See application file for complete search history.

(56) References Cited

FOREIGN PATENT DOCUMENTS

WO  WO-2014164801 A1  10/2014

OTHER PUBLICATIONS

Shaikh, M.N., et al., "Magnetic Nanoparticle-Supported Ferrocenylphosphine: a Reusable Catalyst for Hydroformylation of Alkene and Mizoroki-Heck Olefination", RSC Advances, Issue 48, 5 Pages total (2016) (Abstract only).
Kayser, B., et al., "Metal Complexes of Alkyne-Bridged α-Amino Acids", European Journal of Inorganic Chemistry, vol. 1998, Issue 11, 3 Pages total, (Nov. 1998) (Abstract only).
Goswami, T.K., et al., "Photocytotoxic Ferrocene-Appended (L-Tyrosine)Copper(II) Complexes of Phenanthroline Bases", Polyhedron, vol. 52, 3 Pages total, (Mar. 22, 2013) (Abstract only).

*Primary Examiner* — Clinton A Brooks
(74) *Attorney, Agent, or Firm* — Oblon, McClelland, Maier & Neustadt, L.L.P.

(57) ABSTRACT

A functionalized magnetic nanoparticle including an organometallic sandwich compound and a magnetic metal oxide. The functionalized magnetic nanoparticle may be reacted with a metal precursor to form in a catalyst for various C—C bond forming reactions. The catalyst may be recovered with ease by attracting the catalyst with a magnet.

5 Claims, 56 Drawing Sheets

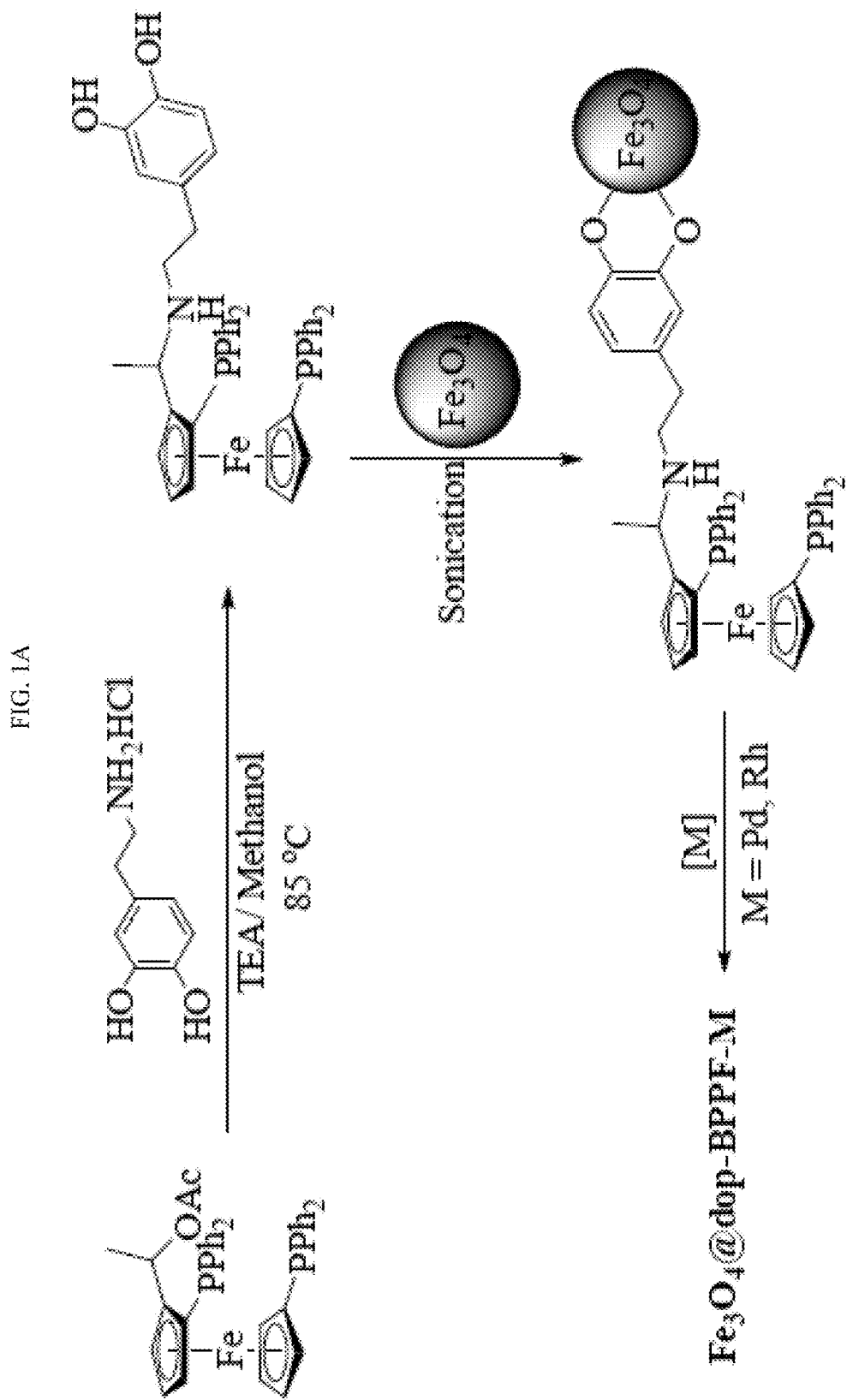

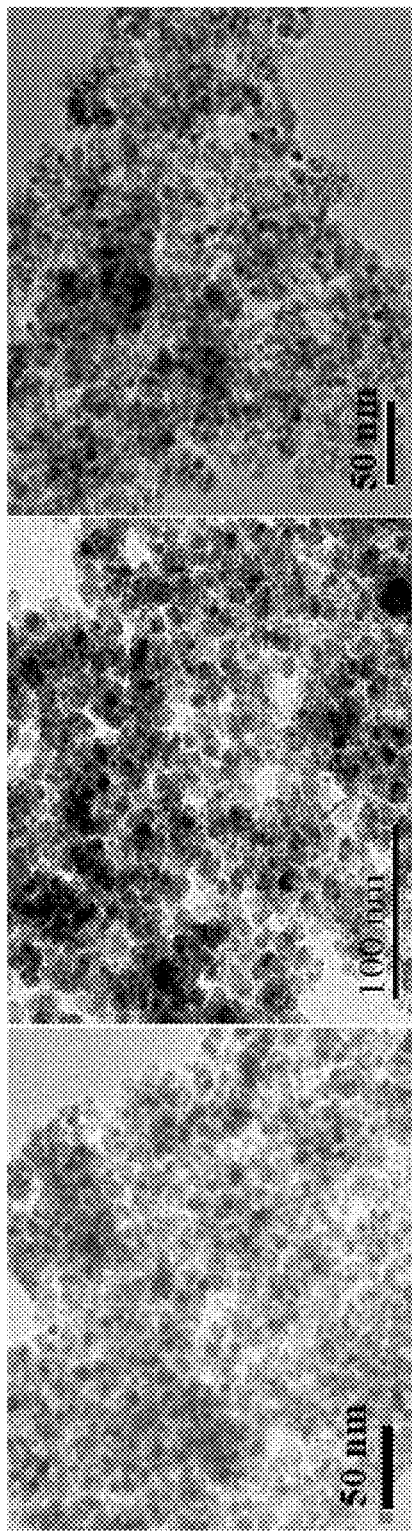

MAGNETIC FERROCENYL-FUNCTIONALIZED NANOPARTICLE

CROSS-REFERENCE TO RELATED APPLICATIONS

The present application is a Continuation of Ser. No. 15/610,269, now allowed, having a filing date of May 31, 2017 which claims priority to U.S. Provisional Application No. 62/406,449 having a filing date of Oct. 11, 2016 and which is incorporated herein by reference in its entirety.

STATEMENT OF FUNDING ACKNOWLEDGMENT

This project was funded by the National Plan for Science, Technology and Innovation (MAARIFAH)-King Abdulaziz City for Science and Technology through the Science and Technology Unit at King Fand University of Petroleum and Minerals (KFUPM), the Kingdom of Saudi Arabia, award number 15-NAN4650-04.

STATEMENT REGARDING PRIOR DISCLOSURES BY THE INVENTORS

Aspects of this technology are described in an article "Magnetic nanoparticle-supported ferrocenylphosphine: a reusable catalyst for hydroformylation of alkene and Mizoroki-Heck olefination" by M. Nasiruzzaman Shaikh, Md. Abdul Aziz, Aasif Helal, Mohamed Bououdina, Zain H. Yamania, and Tae-Jeong Kim, in RSC Advances, 2016, pages 41687-41695, which is incorporated herein by reference in its entirety.

BACKGROUND

Field of the Disclosure

The present disclosure relates to a functionalized magnetic nanoparticle including an organometallic sandwich compound and a functional group which can bind to a nanoparticle. The disclosure also relates to a magnetic catalyst which catalyzes C—C bond forming reactions such as hydroformylation and the Mizoroki-Heck coupling reaction.

Description of the Related Art

Carbon-carbon bond formation reactions mediated by various transition metals have emerged as increasingly important methodologies for the preparation of numerous organic building blocks for drugs, pesticides, dye, and natural products (M. A. Gauthier, H.-A. Klok, Chem. Commun. 23 (2008) 2591-2611; D.-W. Ryu, D. N. Primer, J. C. Tellis, G. A Molander, Chem. Eur. J. 22 (2016) 120-123; A. Brennfuhrer, H. Neumann, M. Beller, Angew. Chem. Int. Ed. 48 (2009) 4114-4133; T. Rybak, D. G Hall, Org. Lett. 17 (2015) 4156-4159; and R. Liu, M. Zhang, T. P. Wyche, G. N. Winston-McPherson, T. S. Bugni, W. Tang, Angew. Chem., Int. Ed. 51 (2012) 7503-7506, each incorporated herein by reference in their entirety). Among the many frequently used C—C bond formation protocols, such as Stille, Heck, Suzuki, Kumada, and Sonogashira, Mizoroki-Heck for olefination and alkene hydroformylation to the corresponding aldehyde are important in synthetic organic and industrial chemistry (J. K. Stille, Angew. Chem. Int. Ed. 25 (1986) 508-524; R. F. Heck, Acc. Chem. Res. 12 (1979) 146-151; N. Miyaura, A. Suzuki, Chem. Rev. 95 (1995) 2457-2483; A. Suzuki, Chem. Commun. (2005) 4759-4763; K. Tamao, K. Sumitani, M. Kumada, J. Am. Chem. Soc. 94 (1972) 4374-4376; T. W. Lyons, M. S. Sanford, Chem. Rev. 110 (2010) 1147-1169; S. Sobhani, Z. Pakdin-Parizi, Applied Catalysis A: General 479 (2014) 112-120; F. Ungvary, Coord. Chem. Rev. 251 (2007) 2087-2102, each incorporated herein by reference in their entirety). Mizoroki-Heck reactions are often catalyzed by different phosphine-based homogeneous Pd metal complexes. For example, $PPh_3$, $P(o-Tol)_3$ and $P(Mes)_3$ are used as monodentate ligands, and dippb (1,4-bis[(diisopropyl)phosphino]butane), dippp (1,4-bis[(diisopropyl)phosphino]propane) and dppf (1,1'-bis(diphenylphosphino)ferrocene) are considered bidentate ligands (H. A. Dieck, R. F. Heck, J. Am. Chem. Soc. 96 (1974) 1133-1136; R. F. Heck, Pure & Appl. Chem. 50 (1978) 691-701; W. A. Heinnann, C. Brobmer, K. Ofele, M. Belier, H. Fischer, J. Mol. Catal. A: Chem. 103 (1995) 133-146; Y. Bendavid, M. Portnoy, M. Gozin, D. Milstein, Organometallics 11 (1992) 1995-1996; M. Portnoy, Y. Bendavid, D. Milstein, Organometallics 12 (1993) 4734-4735; and T. Jia, P. Cao, B. Wang, Y. Lou, X. Yin, M. Wang, J. Liao, J. Am. Chem. Soc. 137 (2015) 13760-13763, each incorporated herein by reference in their entirety). In a similar fashion, Co-, Rh- and Ir-based metal complexes have been used for hydroformylation in the presence of syngas and provide high regioselectivities (C. Godard, S. B. Duckett, S. Polas, R. Tooze, A. C. Whitwood, Dalton Trans. 14 (2009) 2496-2509; C. Kubis, M. Sawall, A. Block, K. Neymeyr, R. Ludwig, A. Bçrner, D. Selent, Chem. Eur. J. 20 (2014) 11921-11931; I. Piras, R. Jennerjahn, R. Jackstell, A. Spannenberg, R. Franke, M. Beller, Angew. Chem. Int. Ed. 50 (2011) 280-284, each incorporated herein by reference in their entirety). However, the separation of the catalyst from the reaction mixture by chromatography, distillation, and extraction is highly tedious, cumbersome, and economically less viable. In addition, the valuable metal and ligands used in the process are not recoverable or reusable, which limits the scope of this process for cost-effective application.

In this context, the development of environmentally benign, reusable, and efficient organocatalysts is the central goal in current research to contribute towards a 'greener' and safe environment. Moreover, the use of a readily available feedstock, such as carbon monoxide, to produce more expensive functionalized organic intermediates via hydroformylation is important. Therefore, extensive efforts have been focused on the development of alternatives to homogeneous catalysis to minimize separation costs and maximize product purity. One of the options is heterogeneous catalysis (W. Dai, Y. Zhang, Y. Tan, X. Luo, X. Tu, Applied Catalysis A: General 514 (2016) 43-50; and R. Abu-Reziq, H. Alper, D. Wang, M. L. Post, J. Am. Chem. Soc. 128 (2006) 5279-5282, each incorporated herein by reference in their entirety). The method for making heterogeneous catalysts is based on the immobilization of ligands or metal complexes over solid supports, such as zeolites, polymers, silica and cellulose (Z.-M. Li, Y. Zhou, D.-J. Tao, W. Huang, X.-S. Chen, Z. Yang, RSC Adv. 4 (2014) 12160-12167; H. Zhang, W. Yang, J. Deng, Polymer 80 (2015) 115-122; A. R. McDonald, C. Müller, D. Vogt, G. P. M. van Klink, G. van Koten, Green Chem. 10 (2008) 424-432; and S. Zhou, M. Johnson, J. G. C. Veinot, Chem. Commun. 46 (2010) 2411-2413, each incorporated herein by reference in their entirety). For example, Koten et al. demonstrated the anchoring of chiral BINAP ligands on the surface of silica, which is highly stable, robust and easy to functionalize for the hydrogenation reaction. Recently, Wang et al. developed a heterocyclic carbene ligand-coated magnetic system and reported encouraging results for the coupling reaction (Z. Wang, Y. Yu, Y. X. Zhang, S. Z. Li, H. Qian, Z. Y. Lin, Green Chem. 17 (2015) 413-420, incorporated herein by reference in its entirety). However, the majority of the heterogeneous catalysts exhibit lower reactivity compared to that of their homogeneous counterpart because the catalytic sites can be obstructed by the solid support and become inaccessible to the substrate, decreasing the overall catalytic activity (V. Polshettiwar, B. Baruwati, R. S. Varma, Chem. Commun. (2009) 1837-1839; and R. S. Varma, Pure & Appl. Chem. 85 (2013) 1703-1710, each incorporated herein by reference in their entirety). Furthermore, solid catalyst separation processes, such as filtration, emulsification, and centrifugation, are complex, and can thus affect the activity and reduce the potential reusability of conventional heterogeneous catalysts (S. Vellalath, I. Coric, B. List, Angew. Chem. Int. Ed. 49 (2010) 9749-9752; and M. Gemmeren, F. Lay, B. List, Aldrichim. Acta 47 (2014) 3-13, each incorporated herein by reference in their entirety).

In view of the foregoing, an objective of the present disclosure is to provide a heterogeneous catalyst with an activity comparable to that of a homogenous catalyst. It is a further objective to provide a heterogeneous catalyst which can be separated from the reaction mixture with ease and which can be recycled with minimal loss in catalytic activity.

SUMMARY OF THE DISCLOSURE

A first aspect of the disclosure relates to a complex represented by Formula (IA), Formula (IB), Formula (IIA), or Formula (IIB), a solvate, or a stereoisomer thereof, wherein Formula (IA), Formula (IB), Formula (IIA), or Formula (IIB) are:

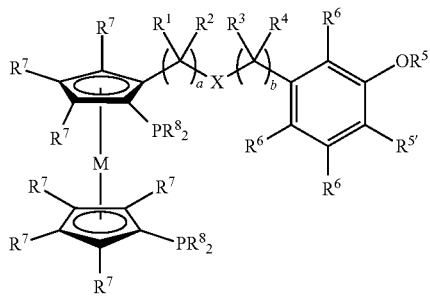
(IA)

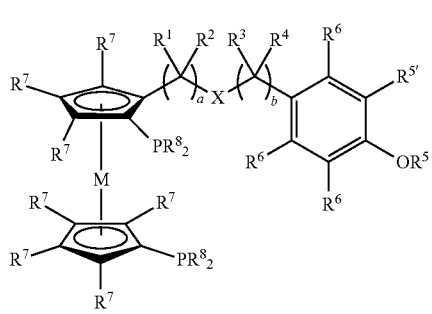
(IB)

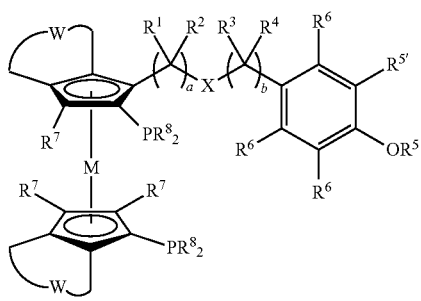
(IIA)

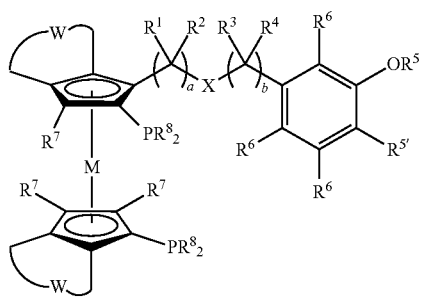
(IIB)

where each of $R^1$, $R^2$, $R^3$, $R^4$, and $R^5$ is independently a hydrogen, an optionally substituted alkyl, an optionally substituted cycloalkyl, an optionally substituted aryl, or an optionally substituted arylalkyl;

$R^{5'}$ is a hydrogen, hydroxy, cyano, nitro, an optionally substituted alkyl, an optionally substituted cycloalkyl, an optionally substituted aryl, an optionally substituted arylalkyl, an optionally substituted alkoxy, an optionally substituted cycloalkyloxy, an optionally substituted aryloxy, an optionally substituted arylalkoxy, or an optionally substituted carbamyl;

each of $R^6$ and $R^7$ is independently a hydrogen, cyano, nitro, an optionally substituted alkyl, an optionally substituted cycloalkyl, an optionally substituted aryl, an optionally substituted arylalkyl, an optionally substituted alkoxy, an optionally substituted cycloalkyloxy, an optionally substituted aryloxy, or an optionally substituted carbamyl;

each of $R^8$ is an optionally substituted alkyl, an optionally substituted cycloalkyl, an optionally substituted aryl, or an optionally substituted arylalkyl;

a and b are independently an integer in a range of 1-10;

X is O or NH;

M is selected from the group consisting of chromium, nickel, iron, lead, ruthenium, and rhodium; and W is an optionally substituted arylene.

In one embodiment, M is iron.

In one embodiment, $R^1$ is an optionally substituted alkyl.

In one embodiment, $R^8$ is an optionally substituted aryl.

In one embodiment, X is NH.

In one embodiment, the complex is:

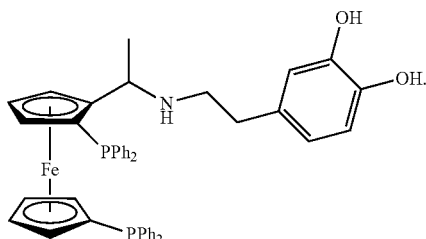

A second aspect of the disclosure relates to a functionalized magnetic nanoparticle, comprising: (i) a complex represented by Formula (IIIA), Formula (IIIB), Formula (IVA), or Formula (IVB), a solvate, or a stereoisomer thereof; and (ii) a nanoparticle comprising at least one magnetic metal oxide selected from the group consisting of nickel(II) oxide, chromium(IV) oxide, manganese(II) oxide, manganese(III) oxide, iron(II) oxide, and iron(III) oxide;

wherein the complex represented by Formula (IIIA), Formula (IIIB), Formula (IVA), or Formula (IVB) is:

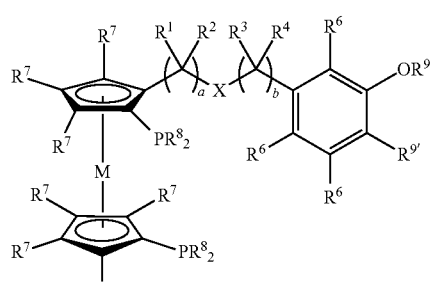
(IIIA)

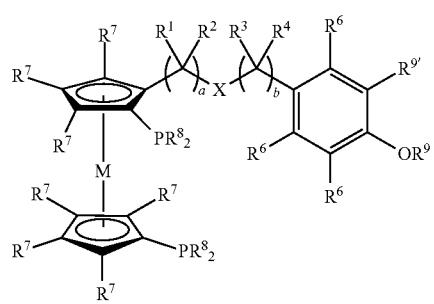
(IIIB)

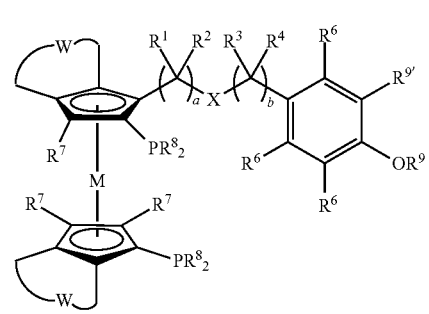
(IVA)

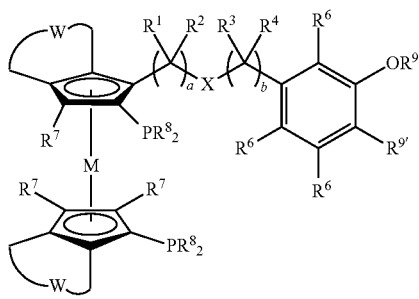
(IVB)

where each of $R^1$, $R^2$, $R^3$, and $R^4$ is independently a hydrogen, an optionally substituted alkyl, an optionally substituted cycloalkyl, an optionally substituted aryl, or an optionally substituted arylalkyl;

each of $R^6$ and $R^7$ is independently a hydrogen, cyano, nitro, an optionally substituted alkyl, an optionally substituted cycloalkyl, an optionally substituted aryl, an optionally substituted arylalkyl, an optionally substituted alkoxy, an optionally substituted cycloalkyloxy, an optionally substituted aryloxy, or an optionally substituted carbamyl;

each of $R^8$ is an optionally substituted alkyl, an optionally substituted cycloalkyl, an optionally substituted aryl, or an optionally substituted arylalkyl;

$R^9$ is a single bond, a hydrogen, an optionally substituted alkyl, an optionally substituted cycloalkyl, an optionally substituted aryl, or an optionally substituted arylalkyl;

$R^{9'}$ is a —O—, hydrogen, hydroxy, cyano, nitro, an optionally substituted alkyl, an optionally substituted cycloalkyl, an optionally substituted aryl, an optionally substituted arylalkyl, an optionally substituted alkoxy, an optionally substituted cycloalkyloxy, an optionally substituted aryloxy, an optionally substituted arylalkoxy, or an optionally substituted carbamyl;

a and b are independently an integer in a range of 1-10;

X is O or NH;

M is selected from the group consisting of chromium, nickel, iron, lead, ruthenium, and rhodium;

W is an optionally substituted arylene; and wherein an oxygen atom in —$OR^9$ group in the complex represented by Formula (IIIA), Formula (IIIB), Formula (IVA), or Formula (IVB) is bound to a surface of the nanoparticle.

In one embodiment, the nanoparticle comprises iron(II) oxide and iron(III) oxide.

In one embodiment, the nanoparticle has an average diameter in a range of 1-20 nm.

In one embodiment, the average diameter of the nanoparticle is in a range of 6-8 nm.

In one embodiment, the functionalized magnetic nanoparticle has a saturation magnetization in a range of 40-70 emu/g.

A third aspect of the disclosure relates to a catalyst, comprising a reaction product of the functionalized magnetic nanoparticle of the second aspect and a palladium complex or a rhodium complex, wherein the catalyst comprises palladium or rhodium bound to a phosphorous atom in at least one —$PR_2^8$ group.

In one embodiment, the complex is:

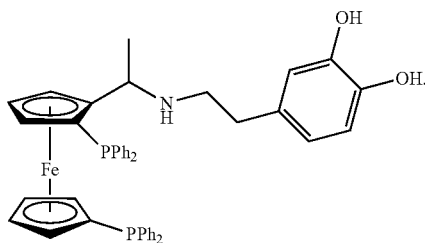

In one embodiment, the catalyst has a saturation magnetization in a range of 30-70 emu/g.

In one embodiment, the catalyst retains at least 90% of an initial catalytic activity when the catalyst is reused.

A fourth aspect of the disclosure relates to a hydroformylation method, comprising reacting an optionally substituted alkene with carbon monoxide and hydrogen in the presence of the catalyst of the third aspect and optionally a solvent thereby forming an aldehyde, wherein the catalyst comprises rhodium bound to a phosphorous atom in at least one —$PR_2^8$ group.

In one embodiment, the reacting is carried out at a pressure in a range of 100-1,000 psi for 5-20 hours at a temperature in a range of 40-80° C., the solvent is present, and the solvent comprises DCM, THF, or both.

In one embodiment, the method further comprises separating the catalyst from the aldehyde, and reusing the catalyst.

A fifth aspect of the disclosure relates to a Mizoroki-Heck coupling method, comprising reacting an optionally substituted styrene with an aryl halide in the presence of the catalyst of the third aspect, a solvent, and a base thereby forming a coupling product, wherein the catalyst comprises palladium bound to a phosphorous atom in at least one —$PR_2^8$ group.

In one embodiment, the reacting is carried out at a temperature in a range of 50-100° C. for 10 minutes to 30 hours, the solvent comprises at least one selected from the group consisting of DMF, water, and toluene, and the base comprises at least one selected from the group consisting of an alkali metal hydroxide, an alkali metal carbonate, and an amine.

In one embodiment, the method further comprises separating the catalyst from the coupling product, and reusing the catalyst.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1A is a reaction scheme for the synthesis of $Fe_3O_4$@dop-BPPF-Pd and $Fe_3O_4$@dop-BPPF-Rh.

FIG. 1B is a transmission electron micrograph of $Fe_3O_4$.

FIG. 1C is a transmission electron micrograph of $Fe_3O_4$@dop-BPPF.

FIG. 1D is a transmission electron micrograph of $Fe_3O_4$@dop-BPPF-Pd.

FIG. 1E is a transmission electron micrograph of $Fe_3O_4$@dop-BPPF-Rh.

FIG. 1F is a high resolution transmission electron micrograph of $Fe_3O_4$@dop-BPPF-Pd.

FIG. 1G is a selected area electron diffraction (SAED) pattern of $Fe_3O_4$@dop-BPPF-Pd.

DETAILED DESCRIPTION OF THE DISCLOSURE

Figure 2:
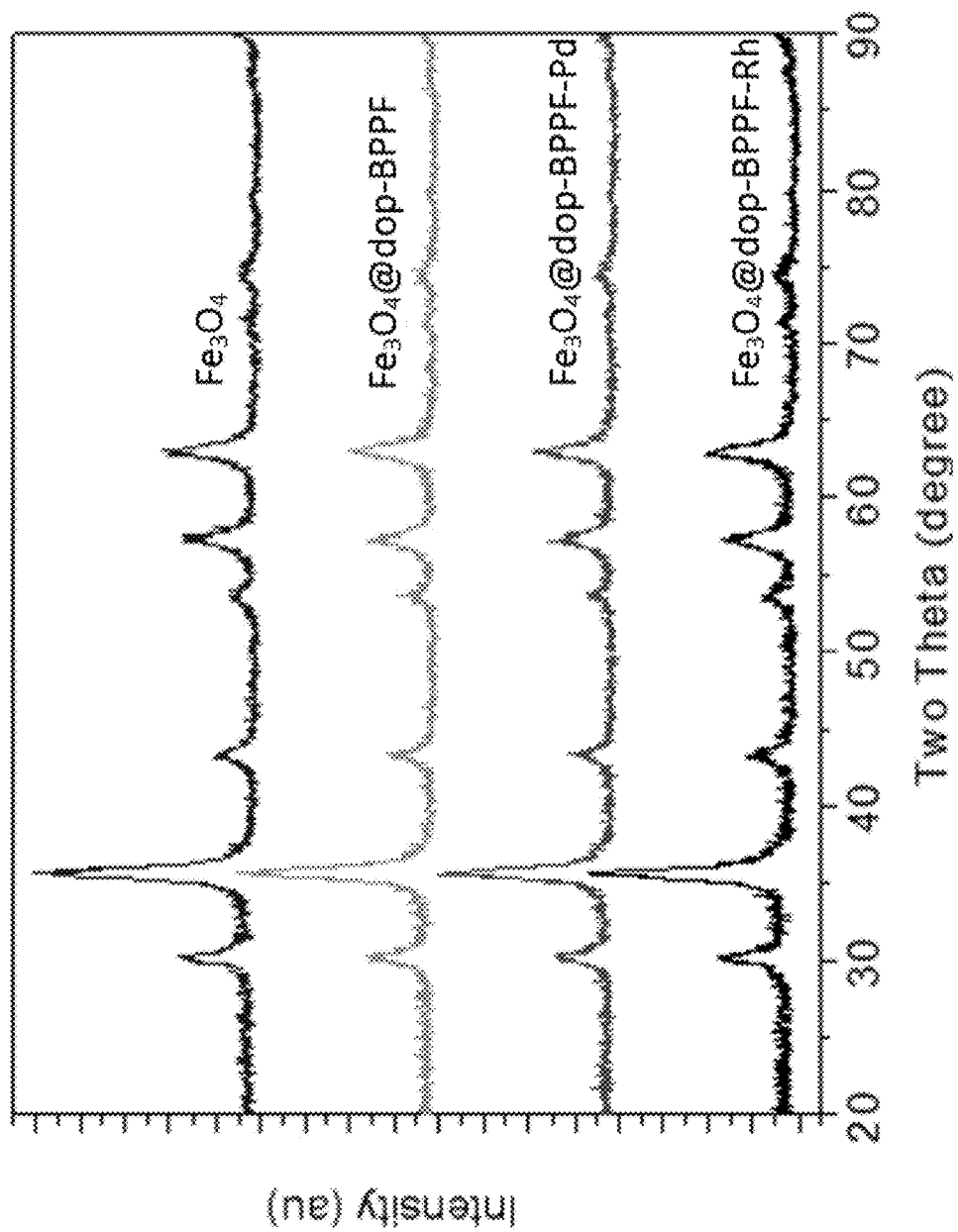
FIG. 2 is an overlay of the XRD patterns of $Fe_3O_4$, $Fe_3O_4$@dop-BPPF, $Fe_3O_4$@dop-BPPF-Pd, and $Fe_3O_4$@dop-BPPF-Rh.
Figure 3D:
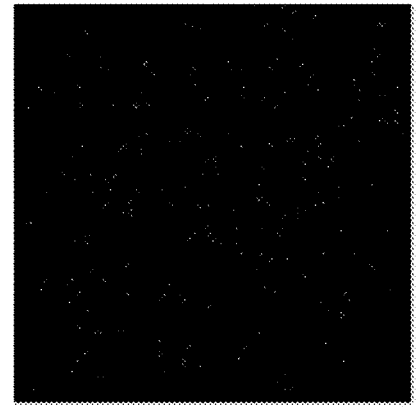
FIG. 3D is an elemental map of rhodium in $Fe_3O_4$@dop-BPPF-Rh.
Figure 3C:
FIG. 3C is an elemental map of palladium in $Fe_3O_4$@dop-BPPF-Pd.
Figure 3B:
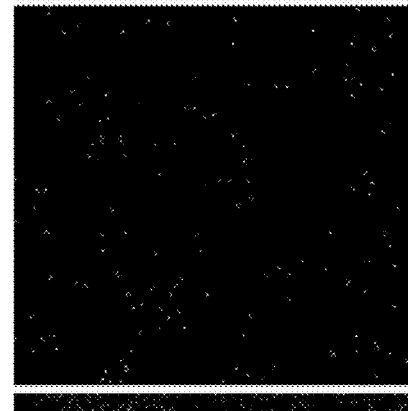
FIG. 3B is an elemental map of phosphorous in $Fe_3O_4$@dop-BPPF.
Figure 3A:
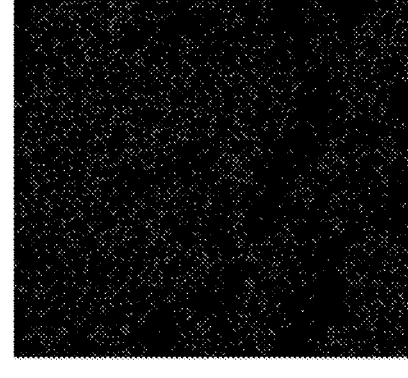
FIG. 3A is an elemental map of iron in $Fe_3O_4$@dop-BPPF.

Embodiments of the present disclosure will now be described more fully hereinafter with reference to the accompanying drawings, in which some, but not all embodiments of the disclosure are shown.

As used herein, the words "a", "an", and the like carry the meaning of "one or more". Within the description of this disclosure, where a numerical limit or range is stated, the endpoints are included unless stated otherwise. Also, all values and subranges within a numerical limit or range are specifically included as if explicitly written out.

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include $^{13}C$ and $^{14}C$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

The first aspect of the disclosure relates to the complex represented by Formula (IA), Formula (IB), Formula (IIA), or Formula (IIB):

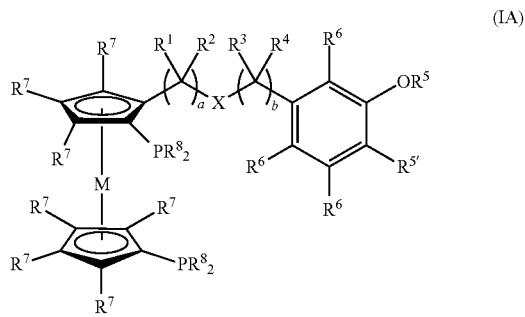

(IA)

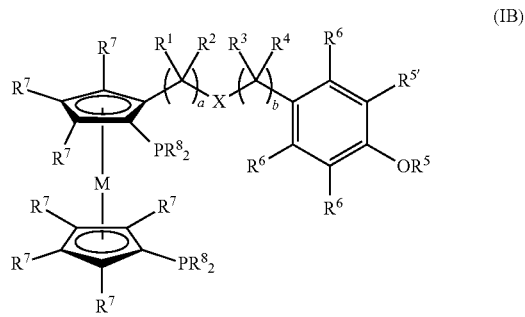

(IB)

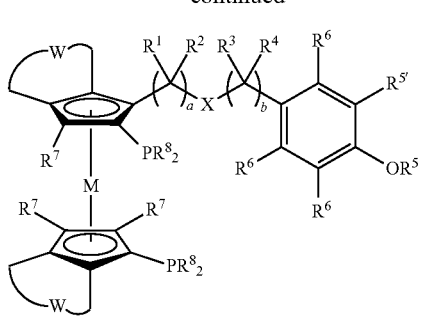

(IIA)

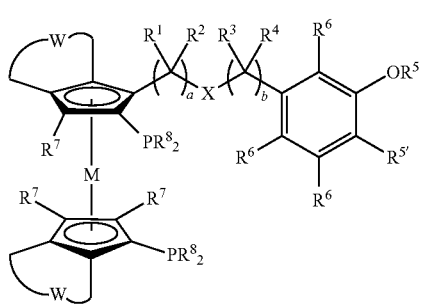

(IIB)

Each of $R^1$, $R^2$, $R^3$, $R^4$, and $R^5$ is independently a hydrogen, an optionally substituted alkyl, an optionally substituted cycloalkyl, an optionally substituted aryl, or an optionally substituted arylalkyl. In some embodiments, $R^1$ is an optionally substituted alkyl. Preferably, $R^1$ is methyl. In preferred embodiments, $R^2$, $R^3$, $R^4$, and $R^5$ are hydrogens.

$R^{5'}$ is a hydrogen, hydroxy, cyano, nitro, an optionally substituted alkyl, an optionally substituted cycloalkyl, an optionally substituted aryl, an optionally substituted arylalkyl, an optionally substituted alkoxy, an optionally substituted cycloalkyloxy, an optionally substituted aryloxy, an optionally substituted arylalkoxy, or an optionally substituted carbamyl. In preferred embodiments, $R^{5'}$ is a hydroxy group.

Each of $R^6$ and $R^7$ is independently a hydrogen, cyano, nitro, an optionally substituted alkyl, an optionally substituted cycloalkyl, an optionally substituted aryl, an optionally substituted arylalkyl, an optionally substituted alkoxy, an optionally substituted cycloalkyloxy, an optionally substituted aryloxy, or an optionally substituted carbamyl. Preferably, $R^6$ and $R^7$ are hydrogens.

Each of $R^8$ is an optionally substituted alkyl, an optionally substituted cycloalkyl, an optionally substituted aryl, or an optionally substituted arylalkyl. In some embodiments, $R^8$ is an optionally substituted aryl. Preferably, $R^8$ is phenyl.

The term "alkyl", as used herein, unless otherwise specified, refers to a straight, branched, or cyclic hydrocarbon fragment. Non-limiting examples of such hydrocarbon fragments include methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl. As used herein, the term "cyclic hydrocarbon" refers to a cyclized alkyl group. Exemplary cyclic hydrocarbon (i.e. cycloalkyl) groups include, but are not limited to, cyclopropyl, cyclobutyl, cyclopentyl, cyclohexyl, norbornyl, and adamantyl. Branched cycloalkyl groups, such as exemplary 1-methylcyclopropyl and 2-methycyclopropyl groups, are included in the definition of cycloalkyl as used in the present disclosure.

The term "aryl", as used herein, and unless otherwise specified, refers to a substituent that is derived from an aromatic hydrocarbon (arene) that has had a hydrogen atom removed from a ring carbon atom. Aryl includes phenyl, biphenyl, naphthyl, anthracenyl, and the like.

As used herein, the term "substituted" refers to compounds where at least one hydrogen atom is replaced with a non-hydrogen group, provided that normal valencies are maintained and that the substitution results in a stable compound. When a compound or a R group (denoted as $R^1$, $R^2$, and so forth) is noted as "optionally substituted", the substituents are selected from the exemplary group including, but not limited to, alkyl; alkoxy (i.e., straight or branched chain optionally substituted alkoxy having 1 to 10 carbon atoms, and includes, for example, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy); cycloalkyloxy (i.e., cyclopentyloxy, cyclohexyloxy, and cycloheptyloxy); aryloxy including an optionally substituted phenoxy; arylalkyloxy (e.g., benzyloxy); an optionally substituted hydrocarbyl; arylalkyl; hydroxy; amino; alkylamino; arylamino; arylalkylamino; disubstituted amines (e.g., in which the two amino substituents are selected from the exemplary group including, but not limited to, alkyl, aryl, or arylalkyl); arylamino; substituted arylamino; nitro; cyano; carbamyl (e.g. —$CONH_2$), substituted carbamyl (e.g. —CONHalkyl, —CONHaryl, —CONHarylalkyl or cases where there are two substituents on one nitrogen from alkyl, aryl, or arylalkyl); aryl; substituted aryl; and mixtures thereof and the like. The substituents may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety).

The term "arylalkyl" as used in this disclosure refers to a straight or branched chain alkyl moiety having 1 to 8 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimethylbenzyl, 2-(4-ethylphenyl)ethyl, 3-(3-propylphenyl)propyl.

The term "hydrocarbyl" as used herein refers to a univalent hydrocarbon group containing up to about 24 carbon atoms (i.e., a group containing only carbon and hydrogen atoms) and that is devoid of olefinic and acetylenic unsaturation, and includes alkyl, cycloalkyl, alkyl-substituted cycloalkyl, cycloalkyl-substituted cycloalkyl, cycloalkylalkyl, aryl, alkyl-substituted aryl, cycloalkyl-substituted aryl, arylalkyl, alkyl-substituted aralkyl, and cycloalkyl-substituted aralkyl.

The terms "a" and "b" are independently an integer in a range of 1-10, 1-8, 2-6, or 3-4. Preferably, "a" is 1 and "b" is 2. The substituent "X" may be O or NH. Preferably, X is NH.

The substituent "W" is an optionally substituted arylene, which is a substituent derived from an arene that has had a hydrogen atom removed from each of two adjacent ring carbon atoms. Exemplary arenes include an optionally substituted benzene, naphthalene, anthracene, phenanthrene, tetracene, chrysene, triphenylene, pyrene, pentacene, benzo[a]pyrene, corannulene, benzo[ghi]perylene, coronene, ovalene, benzo[c]fluorene. In some embodiments, the arylene is a phenylene.

The term "solvate" means a physical association of the complex of this disclosure with one or more solvent molecules, whether organic or inorganic. The physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution-phase and isolable solvates. Exemplary solvates include, but are not limited to, hydrates, ethanolates, methanolates, and isopropanolates. Methods of solvation are generally known in the art.

The term "stereoisomer" refers to isomers that have the same molecular formula and sequence of bonded atoms, but differ in the three-dimensional orientations of their atoms in space.

The metal "M" is chromium, nickel, iron, lead, ruthenium, or rhodium. Preferably, M is iron. During the past few decades, ferrocene-based complexes have been widely studied because their electron-rich aromatic structural motifs can be readily functionalized by electrophilic aromatic substitution reactions. In addition, their relatively low cost, thermal stability, high tolerance to moisture and oxygen, and very unique chemical properties make these materials attractive. Despite the impressive progress in ferrocene-based homogeneous catalysis, the use of ferrocene in heterogeneous catalysis has remained largely unexplored.

In some embodiments, the complex is:

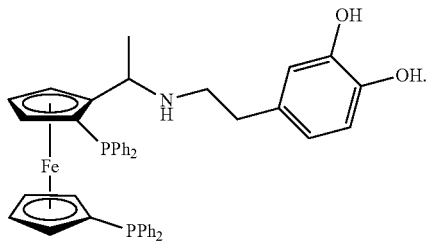

The complex represented by Formula (IA), Formula (IB), Formula (IIA), or Formula (IIB) may be prepared by the following procedure. The complex precursor represented by Formula (V) or Formula (VI) may be dissolved in a solvent (preferably an anhydrous solvent) and then mixed with the compound of Formula (VII) or Formula (VIII) and a base. The complex precursor is:

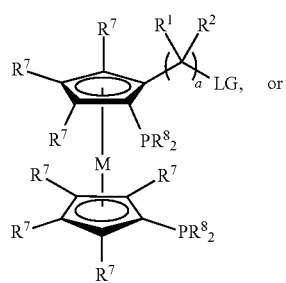

(V)

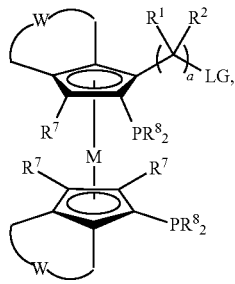

(VI)

where LG is Cl, Br, I, OTf (triflate), OTs (p-toluenesulfonate), or OAc (acetate).

The compound of Formula (VII) or Formula (VIII) is:

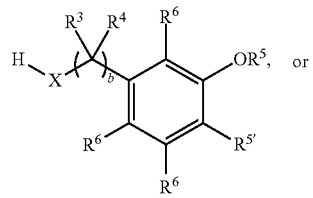

(VII)

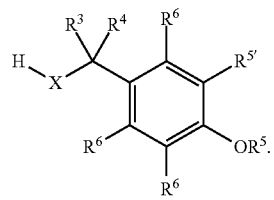

(VIII)

A concentration of the precursor represented by Formula (V) or Formula (VI) in the solvent may be in a range of 10-1,000 mM, 20-500 mM, or 40-100 mM. A concentration of the compound of Formula (VII) or (VIII) in the resulting reaction mixture may be in a range of 10-1,000 mM, 50-500 mM, or 100-200 mM. A concentration of the base in the resulting reaction mixture may be in a range of 0.1-2 M, 0.3-1.5 M, or 0.5-1 M. The resulting reaction mixture may be kept under an inert atmosphere provided by inert gases such as argon, nitrogen, or mixtures thereof. The reaction mixture may be agitated at a temperature of 30-95° C., 50-90° C., or 70-85° C. for 5-30 hours, 8-20 hours, or 10-15 hours thereby forming the complex represented by Formula (IA), Formula (IB), Formula (IIA), or Formula (IIB). The reaction mixture may be agitated throughout the duration of the reaction by employing a rotary shaker, a magnetic stirrer, a centrifugal mixer, or an overhead stirrer. In another embodiment, the reaction mixture is left to stand (i.e. not stirred). In one embodiment, the reaction mixture is sonicated in an ultrasonic bath or with an ultrasonic probe. An external heat source, such as a water bath or an oil bath, an oven, microwave, or a heating mantle, may be employed to heat the reaction mixture. In a preferred embodiment, the external heat source is a thermostatted thermocirculator. In some embodiments, the reaction mixture is heated with microwave irradiation. The complex may be isolated and purified by methods known to those skilled in the art, such as filtration through a celite containing cartridge, aqueous work-up, extraction with organic solvents, distillation, crystallization, column chromatography, and high pressure liquid chromatography (HPLC) on normal phase or reversed phase. Preferred methods include, evaporating the reaction mixture to dryness, purifying the residue with column chromatography, and recrystallization. An isolated yield of the complex may be in a range of 30-90%, 40-80%, or 50-70%.

As used herein, the term "solvent" includes, but is not limited to, water (e.g. tap water, distilled water, doubly distilled water, deionized water, deionized distilled water), organic solvents, such as ethers (e.g. diethyl ether, tetrahydrofuran, 1,4-dioxane, tetrahydropyran, t-butyl methyl ether, cyclopentyl methyl ether, di-iso-propyl ether), glycol ethers (e.g. 1,2-dimethoxyethane, diglyme, triglyme), alcohols (e.g. methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol), aromatic solvents (e.g. benzene, o-xylene, m-xylene, p-xylene, and mixtures of xylenes, toluene, mesitylene, anisole, 1,2-dimethoxybenzene, α,α,α,-trifluoromethylbenzene, fluorobenzene), chlorinated solvents (e.g. chlorobenzene, dichloromethane, 1,2-dichloroethane, 1,1-dichloroethane, chloroform), ester solvents (e.g. ethyl acetate, propyl acetate), amide solvents (e.g. dimethylformamide, dimethylacetamide, N-methyl-2-pyrrolidone), urea solvents, ketones (e.g. acetone, butanone), acetonitrile, propionitrile, butyronitrile, benzonitrile, dimethyl sulfoxide, ethylene carbonate, propylene carbonate, 1,3-dimethyl-3,4,5,6-tetrahydro-2(1H)-pyrimidinone, and mixtures thereof.

As used herein, the term "base" includes, but is not limited to, an alkali metal hydride (e.g. sodium hydride, potassium hydride), an alkali metal hydroxide (e.g. lithium hydroxide, potassium hydroxide, sodium hydroxide, cesium hydroxide), an alkali metal carbonate (e.g. lithium carbonate, potassium carbonate, sodium carbonate, cesium carbonate), an alkali metal acetate (e.g. lithium acetate, sodium acetate, potassium acetate), an amine (e.g. trialkylamine of formula NR'$_3$ (where each R' may be independently ethyl, n-propyl, and n-butyl) and dialkylamine of formula HNR'$_2$, or mixtures thereof, diethylamine, di-n-butylamine, pyrrolidine, piperidine, triethylamine, tri-n-butylamine, diisopropylethylamine, dicyclohexylmethylamine, pyridine, 2,6-dimethylpyridine, 4-aminopyridine, N-methyl-2,2,6,6-tetramethylpiperidine, 2,2,6,6-tetramethylpiperidine, 2,6-di-tert-butylpyridine, 1,4-diazabicyclo[2.2.2]octane), and mixtures thereof. In some embodiments, the base is ammonium hydroxide. Preferably, the base is triethylamine.

The second aspect of the disclosure relates to the functionalized magnetic nanoparticle comprising (i) a nanoparticle comprising a magnetic metal oxide, and (ii) a complex represented by Formula (IIIA), Formula (IIIB), Formula (IVA), or Formula (IVB), a solvate, or a stereoisomer thereof:

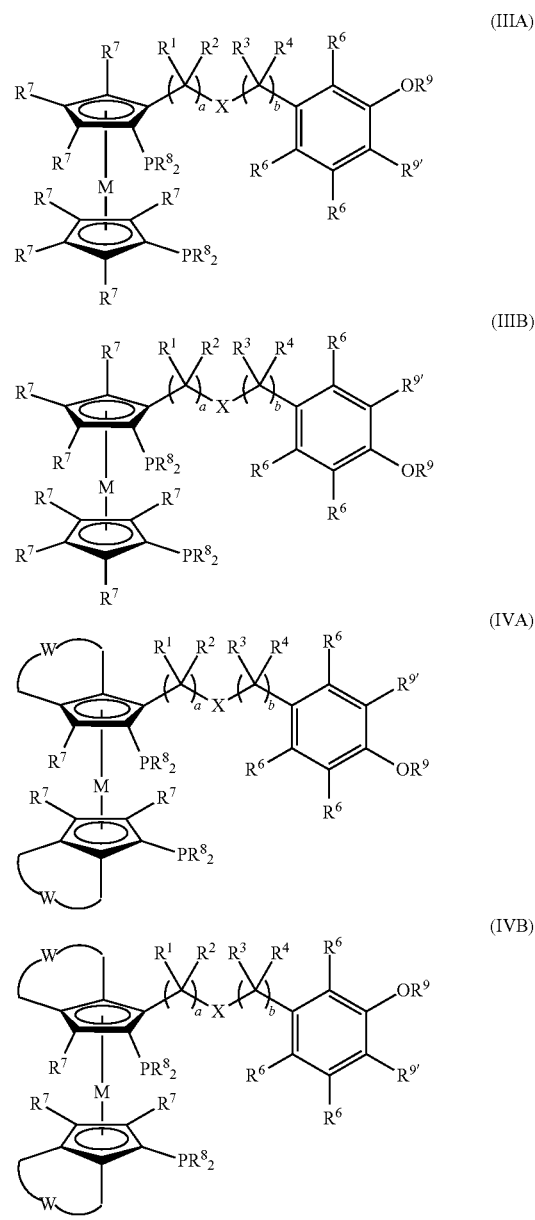

The use of nanoparticles in catalysis is advantageous because performance characteristics of homogeneous catalysts can be obtained without the separation problems of homogeneous catalysts.

The nanoparticle may preferably be spherical or substantially spherical (e.g., oval or oblong shape). In other embodiments, the nanoparticle can be of any shape that provides desired photocatalytic activity. In some embodiments, the nanoparticle is in the form of at least one shape such as a sphere, a rod, a cylinder, a rectangle, a triangle, a pentagon, a hexagon, a prism, a disk, a platelet, a flake, a cube, a cuboid, and an urchin (e.g., a globular particle possessing a spiky uneven surface).

The nanoparticles may be uniform. As used herein, the term "uniform" refers to no more than 10%, no more than 5%, no more than 4%, no more than 3%, no more than 2%, or no more than 1% of the distribution of the nanoparticles having a different shape. For example, the mixed metal spheres are uniform and have no more than 1% of nanoparticles in an oblong shape. In some embodiments, the nanoparticles may be non-uniform. As used herein, the term "non-uniform" refers to more than 10% of the distribution of the nanoparticles having a different shape.

Dispersity is a measure of the heterogeneity of sizes of molecules or particles in a mixture. In probability theory and statistics, the coefficient of variation (CV), also known as relative standard deviation (RSD) is a standardized measure of dispersion of a probability distribution. It is expressed as a percentage and is defined as the ratio of the standard deviation ($\sigma$) of to the mean ($\mu$, or its absolute value $|\mu|$). The CV or RSD is widely used to express precision and repeatability. It shows the extent of variability in relation to the mean of a population. The nanoparticles having a narrow size dispersion, i.e. monodispersity, is preferred. As used herein, "monodisperse", "monodispersed" and/or "monodispersity" refers to nanoparticles having a CV or RSD of less than 25%, preferably less than 20%.

The nanoparticles may be monodisperse with a coefficient of variation or relative standard deviation (ratio of the particle size standard deviation to the particle size mean) of less than 15%, less than 12%, less than 10%, less than 9%, less than 8%, less than 7%, less than 6%, less than 5%, or preferably less than 2%.

In one embodiment, the nanoparticles are monodisperse and have a particle diameter distribution in a range of 75% of the average particle diameter to 125% of the average particle diameter, 80-120%, 85-115%, 86-114%, 87-113%, 88-112%, 89-111%, 90-110%, or preferably 95-105% of the average particle diameter.

An average diameter (e.g., average particle diameter) of the nanoparticle, as used herein, refers to the average linear distance measured from one point on the nanoparticle through the center of the nanoparticle to a point directly across from it. The nanoparticles may have an average diameter in a range of 1-20 nm, 2-18 nm, 4-15 nm, or 6-8 nm. In some embodiments, the nanoparticles have an average diameter in a range of 20-100 nm, 25-70 nm, or 30-40 nm. The nanoparticles may be agglomerated or, preferably, non-agglomerated (i.e. the nanoparticles are well separated from one another and do not form clusters). In one embodiment, the nanoparticles are agglomerated and the agglomerates have an average diameter in a range of 10-500 nm, 50-300 nm, or 100-200 nm. The nanoparticles may be crystalline, polycrystalline, nanocrystalline, or amorphous. Preferably, the nanoparticles are nanocrystalline. The nanoparticles may have multiple phases or a single phase. A crystallite size may range from 1-20 nm, 5-15 nm, or 8-10 nm. The nanoparticles may have a microstrain in a range of 0.1-1%, 0.2-0.8%, or 0.3-0.5%. As used herein, the term "microstrain" refers to the root mean square of the variations in the lattice parameters across the individual nanocrystallites.

The nanoparticles may have a BET surface area in a range of 50-2,000 $m^2/g$, 200-1,600 $m^2/g$, or 500-1,400 $m^2/g$. The BET surface area may be determined by physical adsorption of a gas on the surface of the nanoparticles and then calculating the amount of adsorbate gas corresponding to a monomolecular layer on the surface.

The dimensions and the characteristics of the nanoparticles may vary from the described ranges and the functionalized magnetic nanoparticle can still function as intended.

The magnetic metal oxide may be at least one metal oxide selected from the group consisting of nickel(II) oxide, chromium(IV) oxide, manganese(II) oxide, manganese(III) oxide, iron(II) oxide, and iron(III) oxide. In some embodiments, the magnetic metal oxide is manganese(II) oxide and manganese(III) oxide, or manganese(II,III) oxide, $Mn_3O_4$. Preferably, the magnetic metal oxide is iron(II) oxide and iron(III) oxide. In some embodiments, the magnetic metal oxide is iron(II,III) oxide, $Fe_3O_4$. In some embodiments, the magnetic metal oxide is ferrimagnetic containing populations of atoms with opposing magnetic moments. However, the opposing moments are unequal and a spontaneous magnetization remains. In preferred embodiments, the magnetic metal oxide shows superparamagnetism which is a form of magnetism appearing in ferromagnetic or ferrimagnetic nanoparticles. In sufficiently small nanoparticles, such as the nanoparticles described herein, magnetization can randomly flip direction under the influence of temperature. In the absence of an external magnetic field, the magnetization appears to be zero and the nanoparticles are in the superparamagnetic state. In this state, an external magnetic field is able to magnetize the nanoparticles. Superparamagnetic nanoparticles have a magnetic susceptibility larger than that of paramagnets. The chemical and physical properties (i.e., shape, size, and morphology) of superparamagnetic iron oxide nanoparticles (SPION) can easily be manipulated. The synthesis of SPION is straightforward and the nanoparticles are easily functionalized (C. O. Dalaigh, S. A. Corr, Y. Gunko, S. J. Connon, Angew. Chem. Int. Ed. 46 (2007) 4329-4332, incorporated herein by reference in its entirety).

The presence of the magnetic metal oxide provides for an easy recovery of the functionalized magnetic nanoparticle and the catalyst of the present disclosure. For example, the functionalized magnetic nanoparticle or catalyst is insoluble in solvents and can be easily separated from other components of the reaction mixture by attracting the functionalized magnetic nanoparticle or the catalyst with a magnet.

The magnetic metal oxide may have a saturation magnetization in a range of 5-150 emu/g, 30-100 emu/g, or 50-70 emu/g. The magnetic susceptibilities may be measured with a laboratory magnetometer such as a vibrating sample magnetometer, a superconducting quantum interference device, inductive pickup coils, a pulsed field extraction magnetometer, a torque magnetometer, a faraday force magnetometer, and an optical magnetometer. The magnetic metal oxide may have a coercivity (Hc) in a range of 3-4 Oe, 3.3-3.99 Oe, or 3.8-3.97 Oe. As used herein, the term "coercivity" refers to the resistance of a magnetic material to changes in magnetization, and is equivalent to the field intensity necessary to demagnetize the fully magnetized material. The magnetic metal oxide may have a remanence (Mr) in a range of 0.75-2 emu/g, 0.8-1.5 emu/g or 0.8-1 emu/g. As used here, the term "remanence" refers to the magnetization left behind in the magnetic metal oxide after an external magnetic field is removed. Remanence is also the measure of that residual magnetization.

The magnetic metal oxide may be purchased or made in-house. The magnetic metal oxide may be produced by the following procedure. A metal salt may be mixed with an alkaline solution at 20-30° C., 22-28° C., 24-26° C. under an inert atmosphere. Exemplary metal salts include, halides (e.g., fluoride, chloride, bromide, and iodide), nitrates, acetylacetonates, acetates, perchlorates, sulfamates, trifluoroacetylacetonates, carbonates, bicarbonates, methanesulfonates, ethanesulfonates, p-toluenesulfonates, salicylates, malates, maleates, succinates, tartrates, citrates, trifluoromethanesulfonates (triflates), hexafluorophosphates, hexafluoroacetylacetonates, sulfites, phosphate, and sulfates of chromium, nickel, iron, lead, ruthenium, and rhodium. In most embodiments, the metal salt is a hydrate. The alkaline solution may have a pH in a range of 8-14, 9-13, or 10-12, and comprises any of the aforementioned base. Preferably, the base is ammonium hydroxide. The reaction mixture may be agitated with the aforementioned method for 1-10, 2-8 hours, or 4-6 hours. Preferably, the reaction mixture is stirred. The pH of the solution may be maintained with the periodic addition (e.g., every 30-100 minutes, every 40-70 minutes, or every 50-60 minutes) of the base. The magnetic metal oxide formed may be insoluble in the alkaline solution and may be collected with a magnet and washed with water several times to remove any unreacted metal salt precursors.

In some embodiments, the magnetic metal oxide is $Mn_3O_4$ and/or $Fe_3O_4$, and the magnetic metal oxide may be prepared by mixing the respective divalent and trivalent metal salts in a stoichiometric ratio of 1:2, or 0.8:2 to 1.2:2, 0.9:2 to 1.1:2, or 0.95:2 to 1.05:2. In some embodiments, the divalent metal salt may be in slight excess, for example, not more than 10 mol %, not more than 5 mol %, not more than 3 mol %, relative to the stoichiometric amount of the trivalent metal salt. In some embodiments, the trivalent metal salt may be in slight excess, for example, not more than 10 mol %, not more than 5 mol %, not more than 3 mol %, relative to the stoichiometric amount of the divalent metal salt.

The functionalized magnetic nanoparticle may be prepared by the following procedure. The complex of Formula (IA), Formula (IB), Formula (IIA), or Formula (IIB) may be dissolved in the aforementioned solvent (preferably an anhydrous organic solvent). Preferably, the solvent is chloroform. A concentration of the complex solution may be in a range of 1-1,000 mM, 2-500 mM, or 5-100 mM. The nanoparticles may be suspended in the same or different solvent. Preferably, the solvent is methanol. An amount of the nanoparticles in the suspension may be in a range of 1-500 mg/ml of solvent, 10-300 mg/ml, or 100-200 mg/ml. The complex solution may be mixed with the suspension of the nanoparticles under an inert atmosphere. The resulting reaction mixture may be agitated with the aforementioned methods of agitation for 0.5-20 hours, 1-15 hours, or 5-10 hours thereby forming the functionalized magnetic nanoparticles. In a preferred embodiment, the reaction mixture is sonicated at a range of 20-120 kHz, 30-90 kHz, or 40-80 kHz. In some embodiments, the sonication duration is about 3-20 min, about 5-15 min, or about 8-12 min. The functionalized magnetic nanoparticles may be collected with a magnet. The complex of Formula (IIIA), Formula (IIIB), Formula (IVA), or Formula (IVB) may be dispersed throughout the functionalized magnetic nanoparticle, and may be determined by EDX spectrum and elemental maps. The unreacted complex may be removed from the functionalized magnetic nanoparticles by washing the functionalized magnetic nanoparticles with the solvent.

The complex of Formula (IIIA), Formula (IIIB), Formula (IVA), or Formula (IVB) is bound to a surface of the nanoparticle through an oxygen atom in the —$OR^9$ group in a monodentate or bidentate manner via a covalent bond (e.g., non-ionic dative bond), an ionic bond, or van der Waals force. The binding of an oxygen atom in the —$OR^9$ group may stabilize and minimize aggregation of the functionalized magnetic nanoparticles (C. Duanmu, L. Wu, J. Gu, X. Xu, L. Feng, X. Gu, Catal. Commun. 48 (2014) 45-49, incorporated herein by reference in its entirety). In some embodiments, $R^9$ is a single bond and/or $R^{9'}$ is —O—, the oxygen atom is covalently bonded to the surface of the nanoparticle. In alternative embodiments, the —$OR^9$ group may be replaced with a —$NR_2^5$ group and the functionalized magnetic nanoparticle will still function as intended (F. Zhang, J. Jin, X. Zhong, S. Li, J. Niu, R. Li, J. Ma, Green Chem. 13 (2011) 1238-1243; T. Jiang, S. Du, T. Jafari, W. Zhong, Y. Sun, W. Song, Z. Luo, W. A. Hines, S. L. Suib Applied Catalysis A: General 502 (2015) 105-113; B. Baruwati, D. Guin, S. V. Manorama, Org. Lett. 9 (2007) 5377-5380; and V. Polshettiwar, R. S. Varma, Org. Biomol. Chem. 7 (2009) 37-40, each incorporated herein by reference in their entirety).

The functionalized magnetic nanoparticle may have a saturation magnetization in a range of 5-150 emu/g, 30-100 emu/g, or 40-70 emu/g. The loading of the complex of Formula (IIIA), Formula (IIIB), Formula (IVA), or Formula (IVB) on the surface of the nanoparticle is in a range of 0.01-10 mmol/g of the nanoparticles, 0.05-1 mmol/g, or 0.2-0.5 mmol/g. The loading may be determined from thermogravimetry.

The catalyst may be prepared by the following procedure. The functionalized magnetic nanoparticles may be suspended in the aforementioned solvent and agitated with the aforementioned method for 1-120 mins, 10-100 minutes, or 20-70 minutes. Preferably, the solvent is chloroform. An amount of the functionalized magnetic nanoparticles in the solvent may be in a range of 1-500 mg/ml of solvent, 10-300 mg/ml, or 50-200 mg/ml. The metal precursor may be dissolved in the same or different solvent. Preferably, the solvent is dichloromethane.

The metal precursor may be a binuclear metal complex, a mononuclear metal complex, or a metal salt of ruthenium, iridium, palladium, or rhodium. Exemplary metal precursors include, without limitation, allylpalladium(II) chloride dimer, (2-methylallyl)palladium(II) chloride dimer, palladium(π-cinnamyl) chloride dimer, (2-butenyl)chloropalladium dimer, palladium(II) chloride, palladium(II) bromide, palladium(II) iodide, bis(benzonitrile) palladium(II) chloride, bis(acetonitrile)palladium(II) chloride, palladium(II) acetate, dichloro(mesitylene)ruthenium(II) dimer, bis(2-methylallyl)(1,5-cyclooctadiene)ruthenium(II), bis(1,5-cyclooctadiene)iridium(I) tetrafluoroborate, bis(1,5-cyclooctadiene)diiridium(I) dichloride, bicyclo[2.2.1]hepta-2,5-diene-rhodium(I) chloride dimer, chloro(1,5-cyclooctadiene)rhodium(I) dimer, hydroxy(cyclooctadiene)rhodium(I) dimer, chlorobis(cyclooctene)rhodium(I) dimer, methoxy(cyclooctadiene)rhodium(I) dimer, chloro(1,5-hexadiene)rhodium(I) dimer, bis(1,5-cyclooctadiene)rhodium(I) tetrafluoroborate, bis(1,5-cyclooctadiene)rhodium (I) tetrakis[bis(3,5-trifluoromethyl)phenyl]borate, bis (acetonitrile)(1,5-cyclooctadiene)rhodium(I) tetrafluoroborate, bis(1,5-cyclooctadiene)rhodium(I) hexafluoroantimonate, and bis(norbornadiene)rhodium(I) trifluoromethanesulfonate.

A concentration of the metal precursor may be in a range of 0.01-100 mM, 0.05-50 mM, or 0.1-10 mM. A molar ratio of the metal precursor to the bound complex of Formula (IIIA), Formula (IIIB), Formula (IVA), or Formula (IVB) may be in a range of 1:1 to 2:1, 1.1:1 to 1.9:1, or 1.3:1 to 1.5:1. The solution of the metal precursor may then be added to the suspension of the functionalized magnetic nanoparticles and agitated by the aforementioned method for 0.5-10 hours, 1-8 hours, or 3-6 hours under an inert atmosphere. The catalyst may be collected with magnet and washed with the solvent to removed unreacted metal precursor.

The catalyst comprises palladium, rhodium, iridium, or ruthenium bound to a phosphorous atom in at least one —$PR_2^8$ group in the complex of Formula (IIIA), Formula (IIIB), Formula (IVA), or Formula (IVB). The functionalized nanoparticle may bind to the palladium, rhodium, iridium, or ruthenium in a monodentate manner via a covalent bond (preferably a non-ionic dative bond) through a phosphorous atom in one —PR$_2^8$ group, or in a bidentate manner via a covalent bond (preferably a non-ionic dative bond) through a phosphorous atom in both —PR$_2^8$ groups.

The catalyst may have a saturation magnetization in a range of 5-150 emu/g, 30-100 emu/g, 30-70 emu/g, or 30-60 emu/g. The catalyst may have a turnover number in a range of 1,500-2,500, preferably 1,500-2,000, more preferably 1,700-2,000 and a turnover frequency in a range of 200-1,500 per hour, preferably 200-1,000 per hour, more preferably 200-500 per hour. Preferably, the catalyst tolerates a variety of functional groups on the reactants. That is, the catalyst maintains the aforementioned turnover number and turnover frequency regardless of the functional groups on the reactants.

The catalyst may be useful for reactions such as Mizoroki-Heck reaction, Mizoroki-Heck-Matsuda, Sonogashira, Kumada, Negishi, Stille, Suzuki, Hiyama, Buchwald-Hartwig, hydroformylation, hydrogenation, allylic alkylation, Michael addition, cyclopropanation, hydroboration, olefin isomerization and hydroacylation, hydrosilylation and silylformylation, cycloisomerization and cyclotrimerization, Alder-ene, allylic substitution, carbocyclizations, carbon-hydrogen insertion, oxidative amination, ylide rearrangements, and 1,3-dipolar cycloadditions. Preferably, it catalyzes reactions such as a hydroformylation reaction and a Heck reaction.

In some embodiments, the catalyst is not preformed but is formed in situ in a reaction flask (i.e., at least one of the aforementioned metal precursors and the functionalized magnetic nanoparticles are added to the reaction flask separately).

In some embodiments, the catalyst comprises rhodium, ruthenium, or iridium bound to a phosphorous atom in at least one —PR$_2^8$ group and the catalyst catalyzes the hydroformylation reaction. Preferably, the catalyst comprises rhodium bound to a phosphorous atom in at least one —PR$_2^8$ group. In a hydroformylation reaction, an optionally substituted alkene is mixed with carbon monoxide and hydrogen gases in the presence of the catalyst and optionally a solvent thereby forming an aldehyde. The aldehyde may be a linear or branched aldehyde. Prior to the mixing with carbon monoxide and hydrogen gases, the optionally substituted alkene and the catalyst may be mixed under an inert atmosphere in the reaction vessel and the mixture is optionally agitated. After which, the reaction vessel is purged with the carbon monoxide and hydrogen gases for 1-10 times, 2-8 times, or 3-6 times. A molar ratio of the carbon monoxide gas to the hydrogen gas may be in a range of 1:3 to 3:1, 1:2 to 2:1, about 1:1. Preferably, syngas is used. The carbon monoxide gas may be replaced by aldehydes, higher alcohols (e.g., cinnamyl alcohol, polyols), and metal carbonyls (e.g., Mo(CO)$_6$ and W(CO)$_6$) to reduce the use of toxic and flammable carbon monoxide gas, and the hydroformylation may still proceed as intended. The reacting may be carried out at a pressure in a range of 100-2,000 psi, 200-1,500 psi, or 500-1,000 psi for 5-20 hours, 8-16 hours, or 10-14 hours at a temperature in a range of 30-90° C., 40-80° C., or 45-70° C. under an inert atmosphere. The reaction mixture may be optionally agitated. The progress of each reaction may be monitored by methods known to those skilled in the art, such as thin layer chromatography, gas chromatography, nuclear magnetic resonance, infrared spectroscopy, and high pressure liquid chromatography combined with ultraviolet detection or mass spectroscopy. Preferably, gas chromatography combined with mass spectroscopy is used.

The conversion of the optionally substituted alkene to the aldehyde may be more than 80%, more than 90%, more than 95%, or more than 99%, based on the number of moles of the optionally substituted alkene. The aldehyde may be linear or branched (see Table 3 for examples of linear and branched aldehydes). In most embodiments, the hydrogenated by-product was not observed in the reaction mixture. For example, there may be less than 0.1 wt %, less than 0.05 wt %, or less than 0.01 wt % of the hydrogenated by-product.

The optionally substituted alkene may be an optionally substituted vinyl arene (e.g., styrene, 4-methyistyrene, 4-vinylanisole, 4-chlorostyrene, 3-nitrostyrene, 2-bromostyrene, and vinylbenzoate) or n-alkene (e.g., 1-octene). An amount of the optionally substituted alkene may be in a range of 0.1-50 mmol, 0.5-20 mmol, or 1-10 mmol. In some embodiments, the optionally substituted alkene may be substituted with electron-donating groups such as amino, amido, hydroxy, alkoxyl, and alkyl. In other embodiments, the optionally substituted alkene is substituted with electron-withdrawing groups such as nitro, cyano, and acetyl. Electron-withdrawing substituents are preferred because the branched aldehydes are formed in high yields (more than 90%, more than 95%, or more than 98%).

In some embodiments, the optionally substituted alkene is a substituted styrene, and the aryl group may comprise up to 5 substituents. Preferably, there is one substituent. The substituent may be located ortho, meta, or para to the vinyl group. Preferably, the substituent is located para to the vinyl group.

The amount of catalyst may be in a range of 0.1-30 mol %, 0.5-20 mol %, or 1-10 mol %, based on the number of moles of the optionally substituted alkene. Higher catalyst loadings (e.g. up to 20 mol %, 30 mol %, 40 mol %, 80 mol %) may be used and the method will still proceed as intended.

In some embodiments, the solvent is present and may be DCM, THF, or mixtures thereof. In these embodiments, a concentration of the optionally substituted alkene is in a range of 10-1,000 mM, 50-500 mM, or 100-300 mM. The polarity of the solvent affects the regioselectivity of the hydroformylation reaction and thus non-polar solvents are preferably used to obtain the branched aldehyde in high yields. A weight ratio of the branched aldehyde to the linear aldehyde may be in a range of 200:1 to 1:200, 100:1 to 1:100, or 100:1 to 1:1. The selectivity toward the branched aldehyde may be due to: (1) the catalytic metal binding sites being far away from the metal nanoparticle surface and thus are not hindered by the nanoparticles; and (2) the steric environment around the phosphines coordinated to the catalytic metal resulted in the predominant production of one isomer.

In some embodiments, the optionally substituted alkene is an n-alkene, and the weight ratio of the branched aldehyde to the linear aldehyde is in a range of 1:50 to 1:150, 1:80 to 1:120, or 1:100 to 1:110.

In some embodiments, the catalyst comprises palladium bound to a phosphorous atom in at least one —PR$_2^8$ group and the catalyst catalyzes the Mizoroki-Heck coupling reaction. In a Mizoroki-Heck coupling reaction, an optionally substituted styrene (e.g., styrene, 4-methylstyrene, 4-vinylanisole, 4-chlorostyrene, 3-nitrostyrene, 2-bromostyrene) reacts with an aryl halide in the presence of the catalyst, the aforementioned solvent, and the aforementioned base thereby forming a coupling product. The reaction may be carried out at a temperature in a range of 50-100° C., 60-95° C., or 70-90° C., for 10 minutes to 30 hours, 30 minutes to 24 hours, or 60 minutes to 4 hours. The reaction may be carried out in an inert atmosphere or in air. The reaction mixture may be optionally agitated.

Preferably, the aryl halide is bromobenzene or iodobenzene. In other embodiments, a benzyl halide, a vinyl halide, an aryl triflate, a benzyl triflate, a vinyl triflate, an aryl tosylate, a benzyl tosylate, or a vinyl tosylate may be used in place of the aryl halide.

Exemplary halides, triflates, and tosylates include, without limitation, 1-bromonaphthalene, 2-bromonaphthalene, bromobenzene, 4-bromoanisole, 4-bromotoluene, 1-bromo-4-fluorobenzene, 2-bromoanisole, N-methyl-2-bromopyrrole, 3-bromoindole, 5-bromo-2-methyl-1,3-benzothiazole, 3-bromobenzofuran, 3-bromobenzothiophene, 2-bromothiophene, 2-bromothiophene, 4-bromo-3-chromene, 1-bromostyrene, (E)-2-bromostyrene, 1-bromocyclohexene, 1-bromocyclopentene, bromoethene, (E)-1-bromopropene, 2-bromopropene, iodobenzene, 1-iodonaphthalene, 2-iodonaphthalene, 4-iodoanisole, 4-iodotoluene, 4-chlorotoluene, 2-chlorotoluene, 1-chloronaphthalene, 2-chloronaphthalene, chlorobenzene, 4-chloroanisole, 2-chloroanisole, 3-chloroindole, N-methyl-2-chloropyrrole, 5-chloro-1,3-benzothiazole, 3-chlorobenzofuran, 3-chlorobenzothiophene, 2-chlorothiophene, 2-chlorothiophene, phenyl tosylate, allyl tosylate, 1-naphthyl tosylate, 2-naphthyl tosylate, phenyl tosylate, p-(ethoxycarbonyl)phenyl tosylate, p-anisyl tosylate, p-tert-butylphenyl tosylate, o-methylphenyl tosylate, o-anisyl tosylate, p-chlorophenyl tosylate, parabenzophenonyl tosylate, p-formylphenyl tosylate, 2-methylcyclohexenyl tosylate, 2-methylbenzo[d]thiazol-5-yl tosylate, 1-tosyl-1H-indol-5-yl tosylate, m-anisyl tosylate, p-(trifluoromethyl)phenyl tosylate, and p-fluorophenyl tosylate, 1-naphthyl triflate, 2-naphthyl triflate, phenyl triflate, p-(ethoxycarbonyl)phenyl triflate, p-anisyl triflate, p-tert-butylphenyl triflate, o-methylphenyl triflate, o-anisyl triflate, p-chlorophenyl triflate, parabenzophenonyl triflate, p-formylphenyl triflate, 2-methylcyclohexenyl triflate, 2-methylbenzo[d]thiazol-5-yl triflate, 1-tosyl-1H-indol-5-yl triflate, m-anisyl triflate, p-(trifluoromethyl)phenyl triflate, and p-fluorophenyl triflate, 2-thienyl and 3-thienyl triflates and their benzoderivatives, 2-furanyl and 3-furanyl triflates and their benzoderivatives, N-Boc-2-pyrrolidinyl and N-Boc-3-pyrrolidinyl triflates, cyclohexenyl triflate, 1-styryl and (E)-2-styryl triflates. Other traditional Heck cross-coupling partners (e.g. mesylates) and non-traditional Heck cross-coupling partners (e.g. alkyl halides, triflates, tosylates, etc.) are known to those of ordinary skill and may also be suitable reaction partners in the disclosed method.

The aryl halide comprises an optionally substituted aryl group which may comprise the aforementioned substituents. Preferably, the aryl group is phenyl. In a preferred embodiment, the substituents are electron-donating groups such as amino, alkoxyl, and alkyl. In another preferred embodiment, the substituents are electron-withdrawing groups such as nitro, cyano, and acetyl. The aryl group may comprise up to 5 substituents. Preferably, there is one substituent. The substituent may be located ortho, meta, or para to the halogen atom. Preferably, the substituent is located para to the halogen atom.

The aryl halide may be an aryl monohalide such as aryl chloride, aryl bromide, and aryl iodide. Preferably, the aryl monohalide is an aryl iodide such as iodobenzene. Exemplary aryl monohalide includes, without limitation, iodobenzene, 4-iodoaniline, 4-iodoacetophenone, 4-iodobenzonitrile, 4-iodoanisole, bromobenzene, 4-bromoacetophenone, and 1-iodo-4-nitrobenzene. In another embodiment, the aryl halide is an aryl dihalide such as 1,4-dichlorobenzene, 1,4-dibromobenzene, and 1,4-diiodobenzene.

The aforementioned base may be used in the Mizoroki-Heck reaction. Preferably the base is potassium hydroxide. The presence of a base is often important for the palladium-catalyzed Mizoroki-Heck coupling reaction in order to neutralize the hydrogen halide produced as the by-product of the coupling reaction (Chih-chung, T.; Mungyuen, L.; Bingli, M.; Sarah, W.; Alan, S. C.; Chem. Lett. 2011, 40:9 955. Thorwirth, R.; Stolle, A.; Ondruschka, B.; Green Chem. 2010, 12, 985. Bakherad, M.; Keivanloo, A.; Samangooei, S.; Omidian, M. J. Organometal. Chem. 2013, 740, 78. Feng, Z.; Yu, S.; Shang, Y. Appl. Organometal. Chem. 2008, 22, 577. Shingo, A.; Motohiro, S.; Yuki, S.; Hirojiki, S.; Takuya, Y.; Aiky, O. Chem. Lett. 2011, 40:9, 925. Korzec, M.; Bartczak, P.; Niemczyk, A.; Szade, J.; Kapkowski, M.; Zenderowska, P.; Balin, K.; Lelarko, J.; Polariski, J. J. Catal, 2014, 313, 1. Zhang, G.; Luan, Y.; Han, X.; Wang, Y.; Wen, X.; Ding, C. Appl. Organometal. Chem. 2014, 28, 332, each incorporated herein by reference in their entirety).

A concentration of the optionally substituted styrene may be in a range of 10-1,000 mM, 50-500 mM, or 100-300 mM. A concentration of the base in the reaction mixture may be in a range of 10-1,000 mM, 50-500 mM, or 100-300 mM. A concentration of the aryl halide in the reaction mixture may be in a range of 5-1,000 mM, 50-500 mM, or 100-300 mM. The aryl halide may be the limiting reagent. The amount of the optionally substituted styrene may be more than 1 molar equivalent, more than 1.5 molar equivalents, and up to 5 molar equivalents, up to 3 molar equivalents, or up to 2 molar equivalents of the amount of aryl halide.

A molar ratio of the base to the optionally substituted styrene may be in range of 10:1 to 1:10, 5:1 to 1:5, 2:1 to 1:2, or about 1:1.

The amount of catalyst may be in a range of 0.1-30 mol %, 0.5-20 mol %, or 1-10 mol %, based on the number of moles of the aryl halide. Higher catalyst loadings (e.g. up to 20 mol %, 30 mol %, 40 mol %, 80 mol %) may be used and the method will still proceed as intended.

The aforementioned solvent may be used in the Mizoroki-Heck coupling reaction. Preferably, the solvent comprises at least one selected from the group consisting of DMF, water, and toluene. Preferably, the solvent is a mixture consisting of dimethyl formamide and water and contains 10-50 vol %, preferably 30-50 vol %, more preferably 40-50 vol % of water, based on a total volume of the solvent.

In some embodiments, the solvent is water and a surfactant (e.g., sodium dodecylsulfate, TWEEN®, and PLURONICS™) may be present to dissolve the organic reactants and facilitate their interaction with the catalyst.

The reaction may be monitored by gas chromatography which is optionally coupled to a mass spectrometer. The yield of the reaction may be more than 40%, more than 60%, more than 80%, or more than 95%. In most embodiments, the biphenyl by-product was not observed in the reaction mixture. For example, there may be less than 0.1 wt %, less than 0.05 wt %, or less than 0.01 wt % of the biphenyl by-product.

The products obtained by the catalyzed methods of the present disclosure are isolated and purified by employing the aforementioned methods which are well-known to those skilled in the art. The products, resulting either from a single run or a combination of runs, comprises less than 10 ppb iron, and/or palladium, rhodium, ruthenium, or iridium, (measured by ICP-MS), preferably less than 5 ppb, more preferably less than 1 ppb, based on a total weight of the product. The leaching of the catalytic metal from the catalyst of the present disclosure into the products is minimal and thus the catalyst may be recycled and reused without much loss in the catalytic activity.

The reaction mixture is preferably heterogeneous and comprises suspended catalyst particles in the liquid reaction mixture. In one embodiment, the catalyst particles are dispersed within the reaction mixture, and may further be filtered and recycled at the end of the reaction. In one embodiment, the catalyst is placed in a bag and the bag is immersed in the reaction mixture. Accordingly, the catalyst remains in the bag until the catalyzed reaction is completed.

In some embodiments, the method further comprises separating the catalyst from the products, followed by recycling the used catalyst. The catalyst may be separated by removing the bag of catalyst, dialysis in a solvent, or using a micro-filter or a paper filter. Preferably, the catalyst is separated from the products by attracting the catalyst with a magnet placed at the bottom of the exterior of the reaction vessel and then decanting the reaction mixture.

The phrase "recycling the catalyst" refers to a process whereby the catalyst is washed by an organic solvent, dried, and then added to a new batch of reactants (either for the same or a different type of catalyzed reaction). Preferred organic solvents for washing the catalyst and/or dialysis may include, without limitation, methanol, acetone, ethanol, tetrahydrofuran, acetonitrile, dichloromethane, ether, glycol ether, acetamide, dimethyl acetamide, dimethyl sulfoxide, water, or combinations thereof. The catalyst may be dried in vacuum (e.g., in a pressure of 0.01-100 mbar, 0.1-50 mbar, or 1-10 mbar), and/or with heating, for example, the catalyst may be dried in a vacuum oven. Dried catalyst may be stored in a desiccator until the next run.

In one embodiment, the catalyst is recycled for at least 2 runs, preferably at least 10 runs, more preferably at least 20 runs, even more preferably at least 30 runs. In some embodiments, the catalyst may be used continuously for 10-50 days, 20-40 days, or 28-32 days. The catalyst may lose less than 5 wt %, preferably less than 2 wt %, more preferably less than 0.1 wt % of palladium/rhodium/iridium/ruthenium (based on an initial amount of palladium/rhodium/iridium/ruthenium present in the catalyst) after the catalyst is used for several runs or several days. The yield of the catalyzed reaction may decrease less than 20 percentage points, less than 10 percentage points, or 5 percentage points after the catalyst is used for several runs or several days. Preferably, the yield of the catalyzed reaction decreases 4-8 percentage points after the catalyst is used for 8-12 runs or 29-31 days. The turnover number and the turnover frequency of the catalyst may decrease less than 10%, preferably less than 5%, more preferably less than 2% after the catalyst is used for several runs or several days.

Having generally described this disclosure, a further understanding can be obtained by reference to certain specific examples which are provided herein for purposes of illustration only and are not intended to be limiting unless otherwise specified. The examples were published in an article "Magnetic nanoparticle-supported ferrocenylphosphine: a reusable catalyst for hydroformylation of alkene and Mizoroki-Heck olefination" by M. Nasiruzzaman Shaikh, Md. Abdul Aziz, Aasif Helal, Mohamed Bououdina, Zain H. Yamania, and Tae-Jeong Kim, in RSC Advances, 2016, pages 41687-41695, which is incorporated herein by reference in its entirety.

EXAMPLE 1 EXPERIMENTAL MATERIALS AND METHODS

All of the chemicals were purchased from Sigma-Aldrich and used as received unless otherwise stated. An inert atmosphere and standard Schlenk techniques were used wherever needed. Standard procedures were followed for preparing dry and deoxygenated solvents. Deionized (DI) water was used throughout the experiments. The surface coating was carried out in a low-power bath sonicator (Cole-Parmer model 08892-21). The $^1$H and $^{13}$C NMR spectra were recorded on a JEOL JNM-LA 500 spectrometer with tetramethylsilane (TMS) as the internal standard. The $^{31}$P NMR spectra were recorded on the same spectrometer using a phosphorous probe and 85% $H_3PO_4$ as the internal reference. The FTIR spectra were obtained on a Nicolet 720 in the range of 400 to 4000 $cm^{-1}$ using KBr pellet. The thermogravimetric analysis (TGA) data were obtained on a Mettler-Toledo model TGA1 STAR$^e$ System at a heating rate of 10° C./min in a temperature range of 25-600° C. in an argon atmosphere. The X-ray diffraction data were collected on a Rigaku model Ultima-IV diffractometer using Cu-K$\alpha$ radiation. The nanoparticles were imaged by field emission scanning electron microscopy (FESEM) on a LYRA 3 Dual Beam Tescan operated at 30 kV. The SEM samples were prepared from ethanolic suspensions on alumina stabs and coated with gold in an automatic gold coater (Quorum, Q150T E). For the elemental analysis and mapping, the energy dispersive X-ray spectra (EDS) were collected on the LYRA 3 Dual Beam Tescan. The transmission electron micrographs were collected on a transmission electron microscope (TEM) (JEOL, JEM 2011) operated at 200 kV with a 4 k×4 k CCD camera (Ultra Scan 400SP, Gatan). The TEM samples were prepared by dropwise application of an ethanolic suspension onto a copper grid and the sample was allowed to dry at room temperature. The catalytic reactions were performed in a STEM Omni® 10-place reaction station and a Teflon-lined autoclave from HiTech, USA (model: M010SSG0010-E129A-00022-1D1101), which was equipped with a pressure gauge and mechanical stirrer. The magnetic susceptibilities were measured using a vibrating sample magnetometer (VSM, model PMC Micromag 3900) equipped with a 1 tesla magnet at room temperature.

EXAMPLE 2 SYNTHESES OF THE COMPOUNDS, COMPLEX, FUNCTIONALIZED MAGNETIC NANOPARTICLE, AND CATALYST

The syntheses of N,N-dimethylferrocenyl ethyl amine (FA), N,N-dimethyl-1-[-1',2-bis(diphenylphosphino)ferrocenyl]ethyl amine (BPPFA) and 1-[-1',2-bis(diphenylphosphino)ferrocenyl]ethyl acetate (BPPFA-OAc) were performed according to previously reported procedures (G.-H. Hwang, E.-S. Ryu, D.-K. Park, S. C. Shim, C. S. Cho, T.-J. Kim, J. H. Jeong, M. Cheong, Organometallics 20 (2001) 5784-5787; and T. Hayashi, T. Mise, M. Fukushima, M. Kagotani, N. Nagashima, Y. Hamada, A. Matsumoto, S. Kawakami, M. Konishi, Bull. Chem. Soc. Japan 53 (1980) 1138-1151, each incorporated herein by reference in their entirety).

Figure 6:
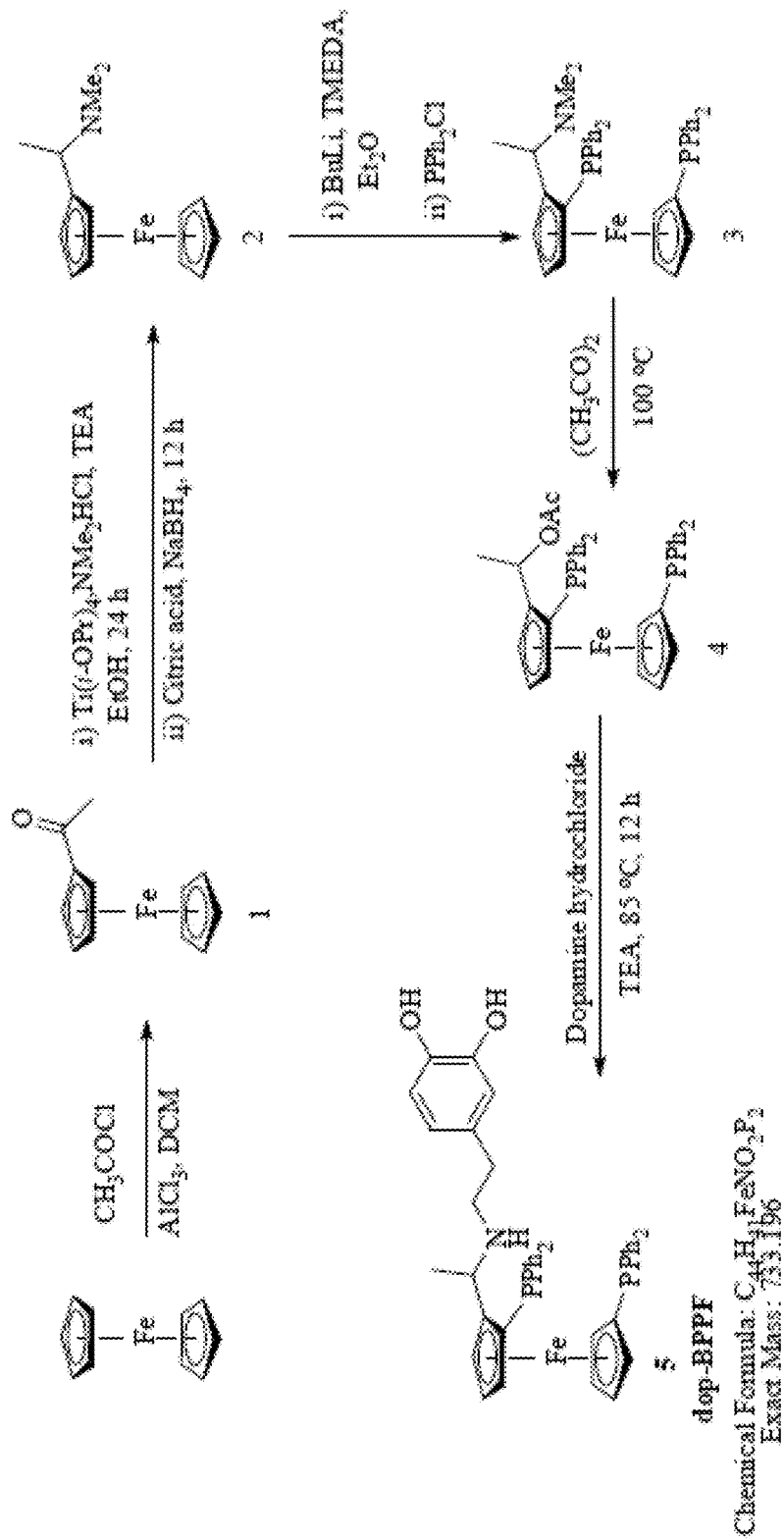
FIG. 6 is a reaction scheme for the synthesis of dop-BPPF.

The synthesis involved the preparation of N,N-dimethyl-1-ferrocenylethylamine followed by dilithiation and reaction with chlorodiphenylphosphine to afford BPPFA (see FIG. 6) (T. Hayashi, K. Yamamoto, M. Kumada, Tetrahedron Lett. (1974) 4405-4408, incorporated herein by reference in its entirety). The freshly prepared BPPFA was acetylated to replace the —NMe$_2$ functional group by reaction with acetic anhydride at 100° C. for 1 hour to yield BPPFA-OAc.

The synthesis of a new ferrocene-based ligand (dop-BPPF, $\{\eta^5\text{-}C_5H_4\text{—}PPh_2\}Fe\{\eta^5\text{-}C_5H_3\text{-}1\text{-}PPh_2\text{-}2\text{-}CH(Me)NH\text{—}CH_2\text{—}CH_2\text{-}4\text{-}C_6H_3\text{-}1,2\text{-}OH\}$) from BPPFA-OAc (1-[1',2-bis(diphenylphosphino)-ferrocenyl]ethyl acetate) is described hereinafter (M. N. Shaikh, M. Bououdina, A. A. Jimoh, M. A. Aziz, A. Helal, A. S. Hakeem, Z. H. Yamani, T.-J. Kim, New J. Chem. 39 (2015) 7293-7299; M. N. Shaikh., V. D. M. Hoang, T-J. Kim, Bull. Korean Chem. Soc. 30 (2009) 3075-3078; and H.-K. Kim, J.-A. Park, K. M. Kim, M. N. Shaikh, D.-S. Kang, J. Lee, Y. Chang, T.-J. Kim, Chem. Commun. 46 (2010) 8442-8444, each incorporated herein by reference in their entirety). Ferrocenylphosphine was used because the phosphine group can coordinate to the catalytic metal (i.e., rhodium or palladium) and the resulting catalyst was found to be stable with excellent catalytic activity. FIG. 1 shows the preparation route for the formation of dopamine-functionalized ferrocenylphosphine.

Synthesis of $\{\eta^5\text{-}C_5H_4\text{—}PPh_2\}Fe\{\eta^5\text{-}C_5H_3\text{-}1\text{-}PPh_2\text{-}2\text{-}CH(Me)NH\text{—}CH_2\text{—}CH_2\text{-}4\text{-}Ph\text{-}1,2\text{-}OH\}$ (dop-BPPF): To a solution of BPPFA-OAc (0.28 g, 0.43 mmol) in anhydrous methanol (10 mL), dopamine hydrochloride (0.19 g, 1.0 mmol) and freshly distilled triethylamine (1 mL) were added under an argon atmosphere (dopamine hydrochloride was made soluble in anhydrous methanol by the excess trimethylamine). The mixture was stirred at 85° C. for 12 hours, and then the solvent was removed under vacuum. The solid residue was dissolved in a minimal amount of methanol and transferred to a silica gel column for separation. The desired orange band was eluted using a combination of ethyl acetate and methanol (9:1) to produce orange solids after removal of the solvents. Recrystallization from methanol/cyclohexane yielded 0.18 g of product (56%). $^{31}P$ NMR (202 MHz, in DMSO-$d_6$): δ −28.14 (s, $PPh_2$), −20.78 (s, $PPh_2$). $^1H$ NMR (DMSO-$d_6$): δ 1.30 (d, J=6.7, 3H, $CHCH_3$), 1.78 (t, 2H, $NCH_2CH_2$), 2.29 (t, 2H, $NCH_2CH_2$), 3.55 (m, 3H, $C_5H_3$), 4.04-4.49 (m, 4H, $C_5H_4$), 6.20 (d, 1H, $C_6H_3$), 6.39 (s, 1H, $C_6H_3$), 6.60 (d, 1H, $C_6H_3$), 7.24-7.50 (m, 20H, $PPh_2$), 8.62 (s, 1H, OH), 8.74 (s, 1H, OH). $^{13}C$ NMR (DMSO-$d_6$): 19.03 ($CHCH_3$), 35.12 ($NCH_2CH_2$), 69.37 ($NCH_2CH_2$), 72.81 ($CHCH_3$), 115.29, 118.91, 128.20, 129.23, 132.11 ($C_6H_3$), 132.67, 132.82, 133.04, 134.43, 143.20, 144.81 ($C_5H_3$, $C_5H_4$ and $PPh_2$). FTIR in KBr (cm$^{-1}$): v=3426 (O—H), 3058 (arC—H), 2920 (Csp$^3$-H) 1522(arC—C). FAB-MS(m/z): calc. for $C_{44}H_{41}FeNO_2P_2$, 733.198([M]$^+$); found, 733.196. Anal. Calcd for $C_{44}H_{41}FeNO_2P_2 \cdot CH_3OH$: C, 70.59; H, 5.92; N, 1.83. Found: C, 70.67; H, 6.17; N, 2.01.

Figure 7:
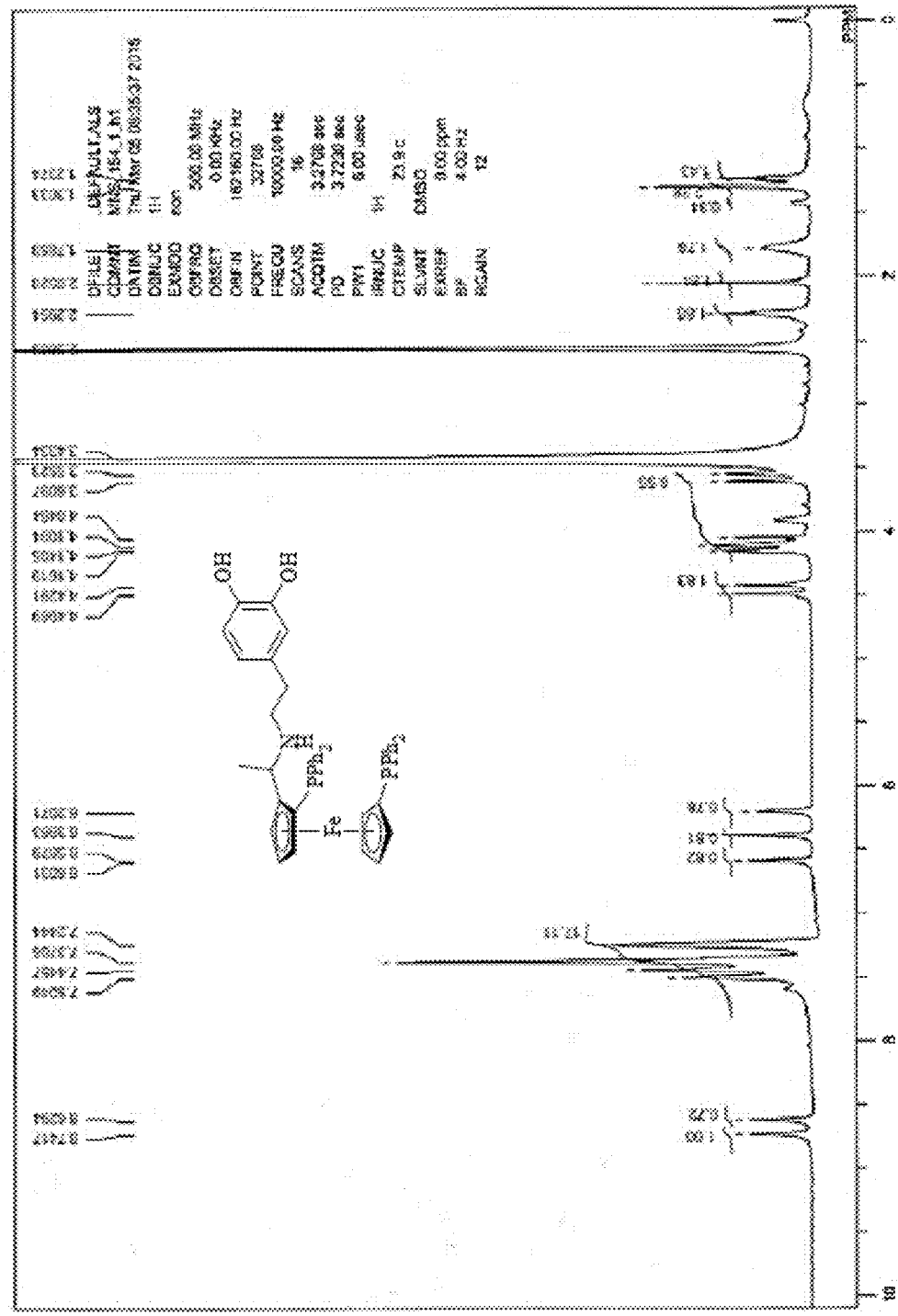
FIG. 7 is a $^1$H NMR spectrum of dop-BPPF in DMSO-$d_6$.
Figure 8:
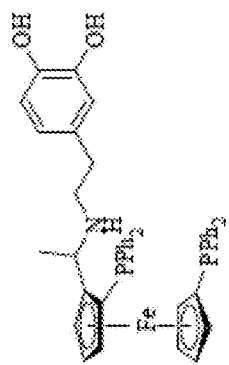
FIG. 8 is a $^{31}$P NMR spectrum of dop-BPPF in DMSO-$d_6$.
Figure 9:
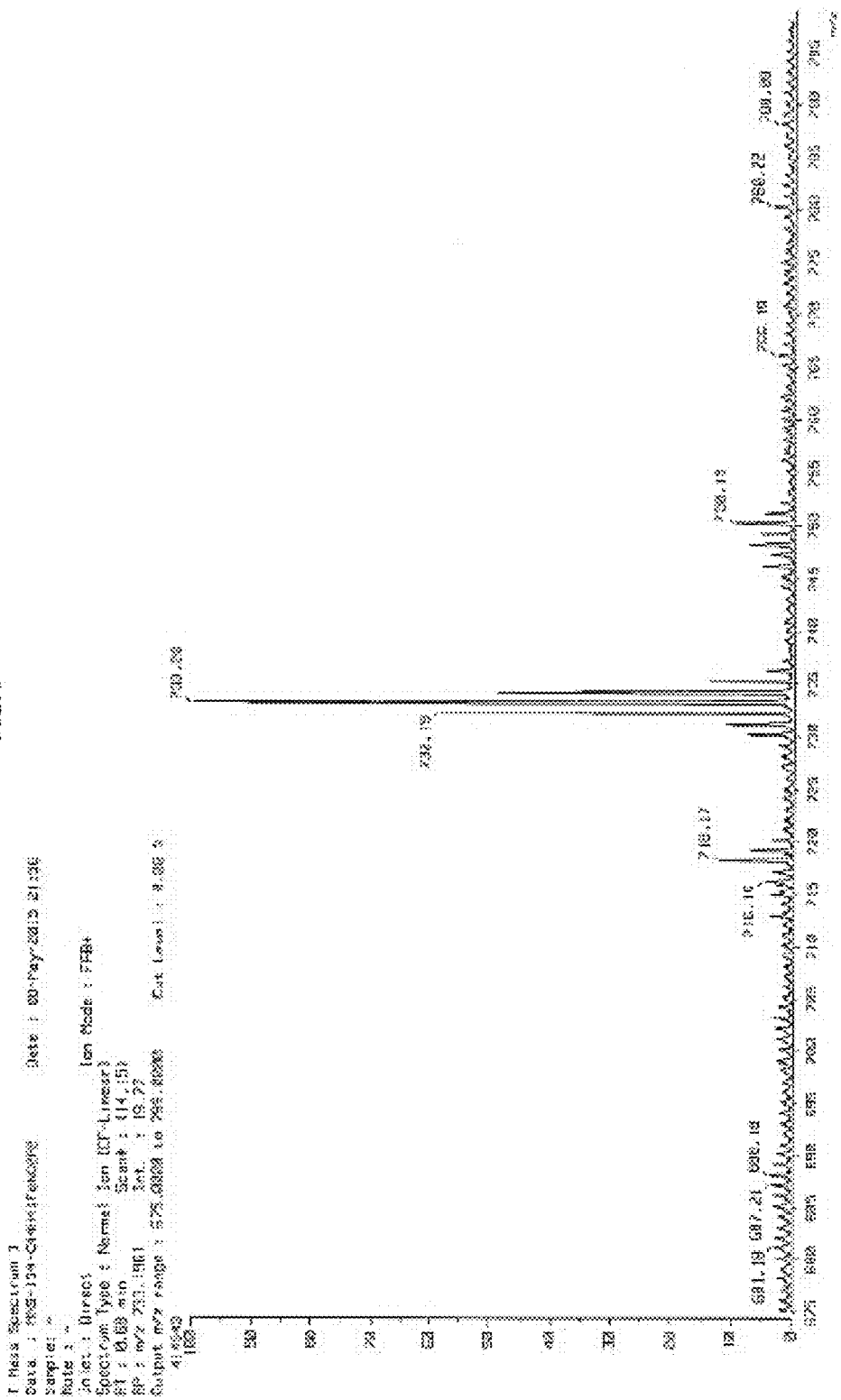
FIG. 9 is a fast atom bombardment (FAB) mass spectrum of dop-BPPF.

Characteristic singlets appeared in the highly shielded (upfield) region (−20 and −28 ppm) in the $^{31}P$ NMR spectra and were assigned to the phosphorous atom in the diphenylphosphine groups attached to the ferrocene ring (see FIG. 8). The presence of ferrocenyl ring protons in the 3.5-4.5 ppm region, an axial methyl proton chemical shift (δ) at 1.30 ppm, and three protons of the phenyl ring of dopamine at 6.20, 6.39 and 6.60 ppm confirmed the formation of the desired compound (see FIG. 7). This compound was further characterized by FAB-mass spectrometry and exhibited the characteristic molecular ion peak (m/z=733.196) (see FIG. 9).

Synthesis of $Fe_3O_4$: Magnetite nanoparticles of 6-8 nm in size were prepared by reaction of divalent and trivalent iron in a 1:2 ratio in an alkaline medium at room temperature under an argon atmosphere with constant stirring (500 rpm). The pH of the solution was held constant with the periodic addition of conc. $NH_4OH$ for 4 hours. A black precipitate was collected using a magnet and washed with DI water several times to remove any unreacted iron precursors.

Synthesis of $Fe_3O_4@\{\eta^5\text{-}C_5H_4\text{—}PPh_2\}Fe\{\eta^5\text{-}C_5H_3\text{-}1\text{-}PPh_2\text{-}2\text{-}CH(Me)NH\text{—}CH_2\text{—}CH_2\text{-}4\text{-}Ph\text{-}1,2\text{-}OH\}$ ($Fe_3O_4@$dop-BPPF): The magnetite nanoparticles (MNPs) were functionalized (see FIG. 1) using a previously reported procedure modified as follows: To a suspension of magnetic nanoparticles (200 mg) in anhydrous chloroform, dop-BPPF (200 mg) solution in dry methanol was added under an argon atmosphere. The mixture was sonicated in a bath sonicator for 6 hours. The surface functionalized magnetic nanoparticles were collected using a magnet after repeated washing with methanol followed by characterization. FTIR in KBr (cm$^{-1}$): v=3435 (O—H+N—H), 2938 (arC—H), 1428 (arC—C), 590 (Fe—O).

Ferrocenylphosphine was linked to the dopamine moiety, which was used as an anchoring unit to attach the complex onto the surface of the magnetic nanoparticles. Bidentate enediol ligands provide higher stability and tight binding to iron oxide by transforming under-coordinated Fe surface sites back to a bulk-like octahedral lattice structure for oxygen-coordinated magnetite, and this behavior is further supported by the Langmuir isotherm, which indicated that the adsorption of dopamine moiety via the 1,2-dihydroxyl functional group was more favorable than its desorption from the metal nanoparticles surface (G. W. Gokel, I. K. Ugi, J. Chem. Educ. Chem. 49 (1972) 294-296; and L. X. Chen, T. Liu, M. C. Thurnauer, R. Csencsits, T. Rajh, J. Phys. Chem. B 106 (2002) 8539-8546, each incorporated herein by reference in their entirety).

Synthesis of $Fe_3O_4@\{\eta^5\text{-}C_5H_4\text{—}PPh_2\}Fe\{\eta^5\text{-}C_5H_3\text{-}1\text{-}PPh_2\text{-}2\text{-}CH(Me)NH\text{—}CH_2\text{—}CH_2\text{-}4\text{-}Ph\text{-}1,2\text{-}OH\}$-M ($Fe_3O_4@$dop-BPPF-M): The suspension of the magnetite nanoparticles (100 mg) in chloroform was sonicated for 1 hour. The solution of $[Rh(NBD)Cl]_2$ (0.015 mmol), slightly excess, in dichloromethane was added to the suspension and stirred for 4 hours under argon atmosphere. The materials was collected and washed with dichloromethane to remove unreacted metal precursor.

The same procedure was followed to prepare $Fe_3O_4@$dop-BPPF-Pd and $[Rh(NBD)Cl]_2$ was replaced with $[Pd(C_3H_5)Cl]_2$.

EXAMPLE 3 CHARACTERIZATION OF THE SYNTHESIZED COMPLEX, FUNCTIONALIZED MAGNETIC NANOPARTICLE, AND CATALYST

Figures 16A, 16B:
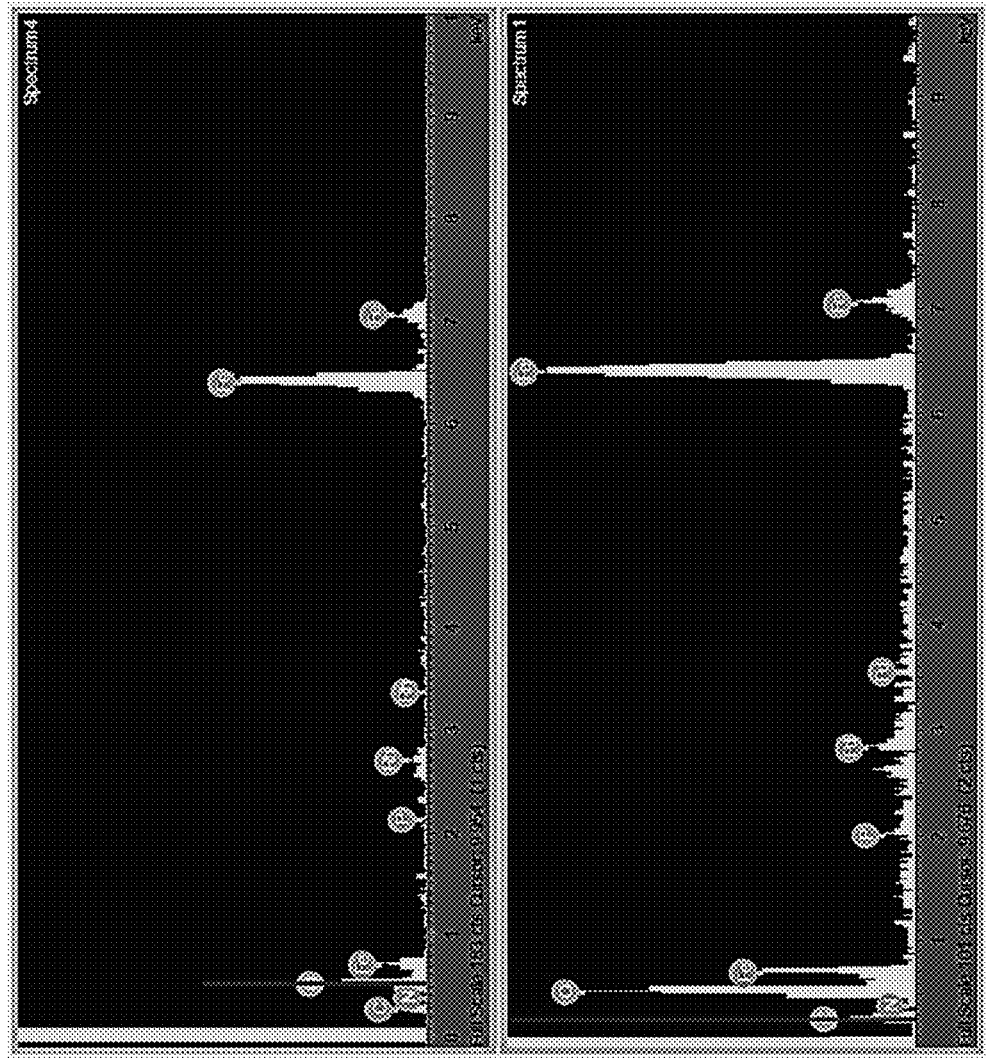
FIG. 16A is an energy dispersive X-ray (EDX) spectrum of $Fe_3O_4$@dop-BPPF-Rh.
FIG. 16B is an EDX spectrum of $Fe_3O_4$@dop-BPPF-Pd.
Figure 17:
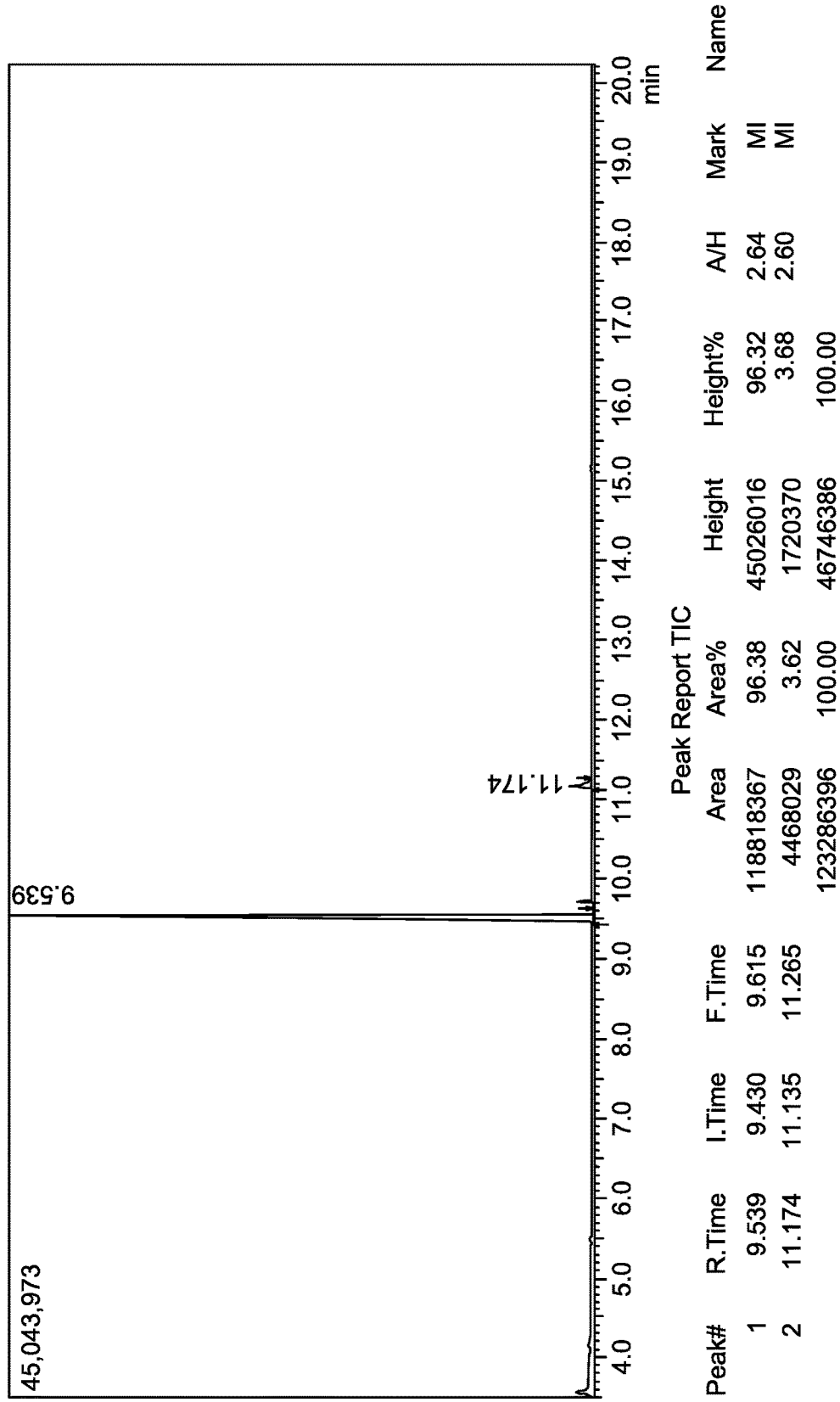
FIG. 17 is a gas chromatogram of the hydroformylated products of styrene formed in DCM at 45° C.
Figure 18:
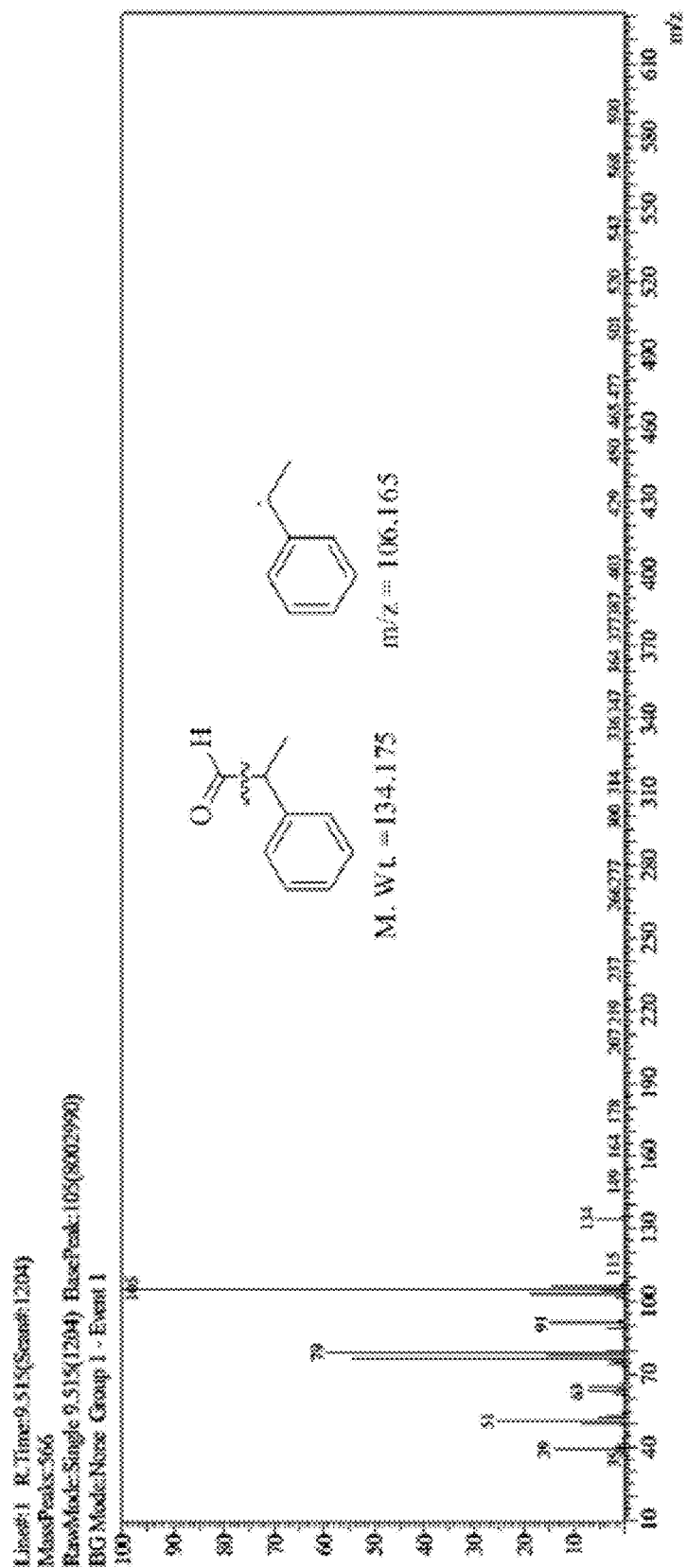
FIG. 18 is a mass spectrum of the branched aldehyde formed by hydroformylating styrene.
Figure 19:
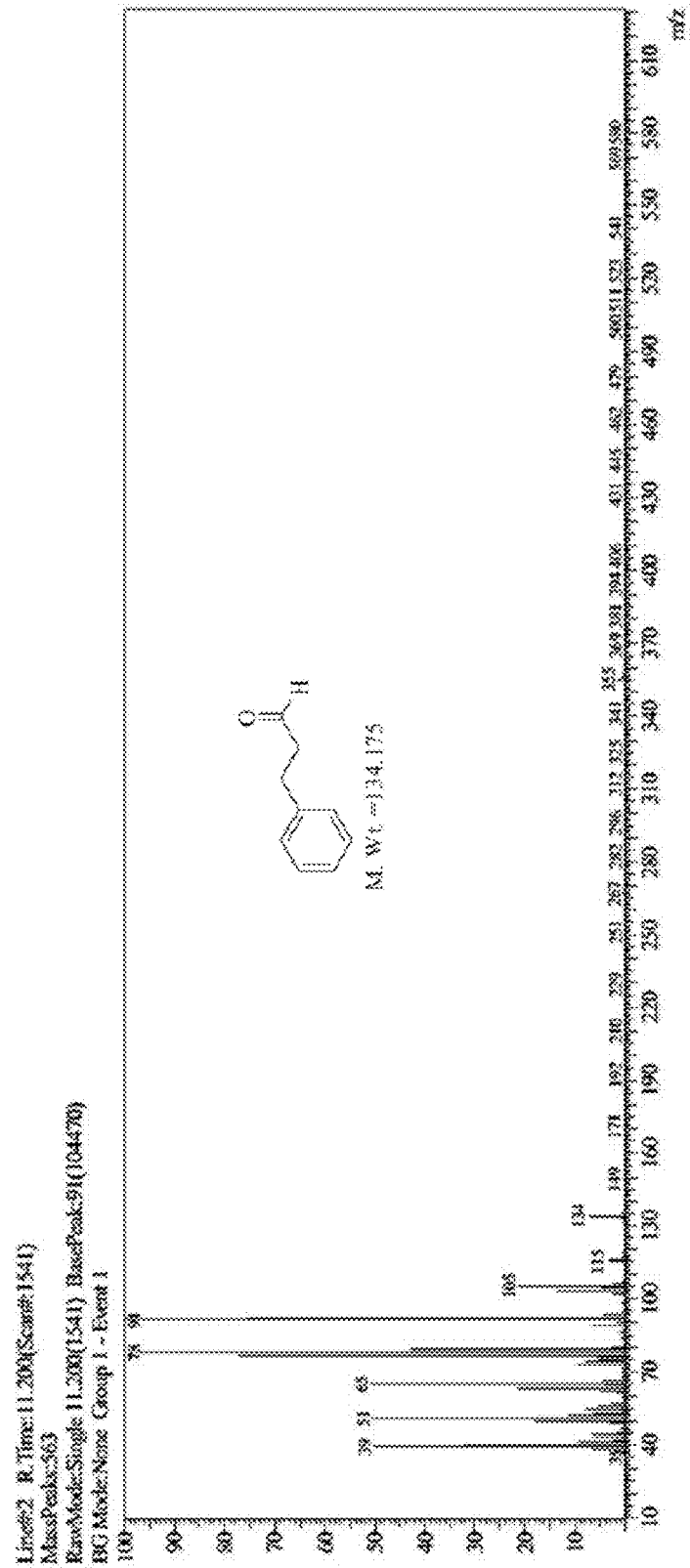
FIG. 19 is a mass spectrum of the hydroformylated products of styrene formed in THF at 45° C.
Figure 20:
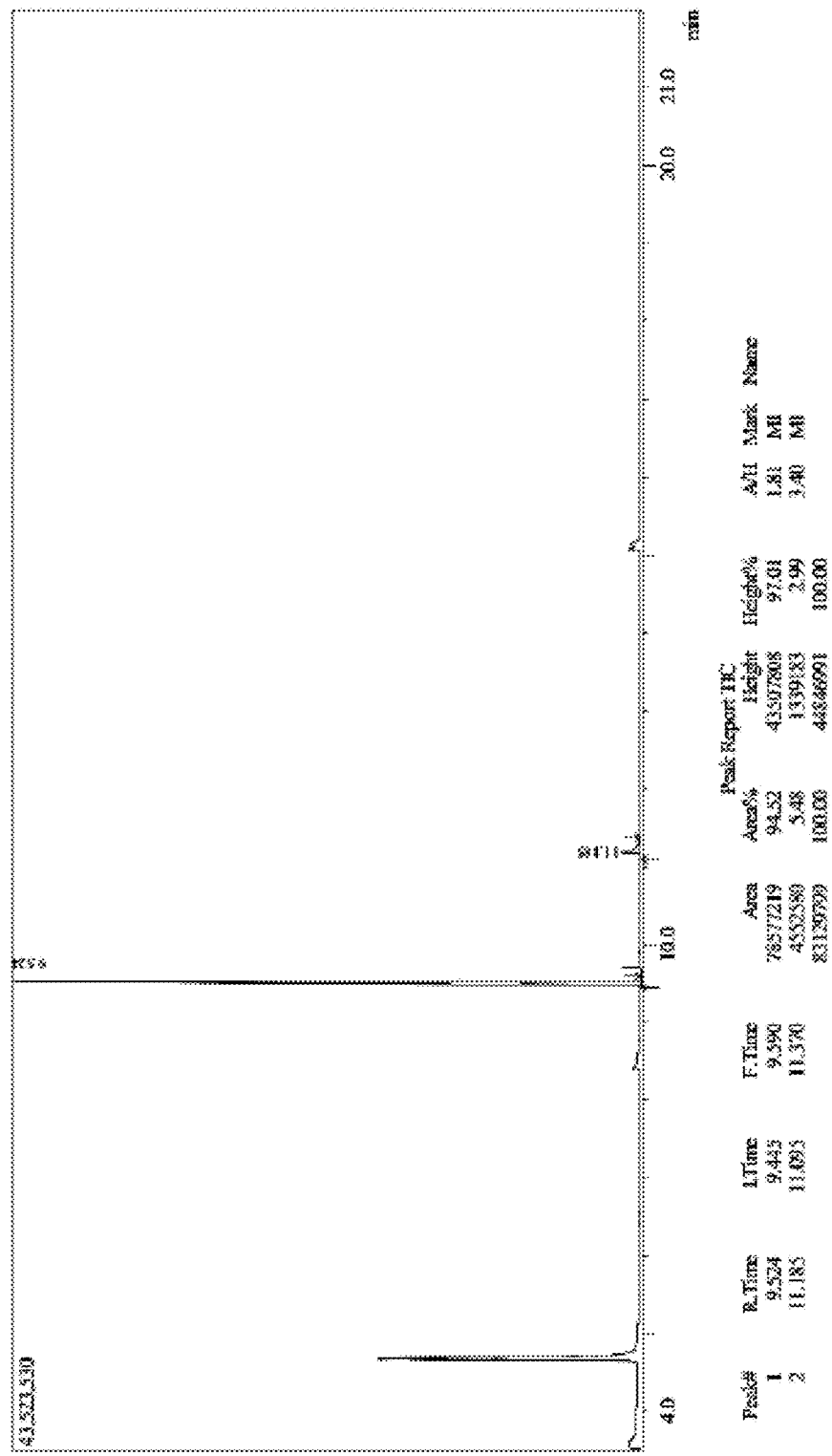
FIG. 20 is a gas chromatogram of the linear aldehyde formed by hydroformylating styrene.
Figure 21:
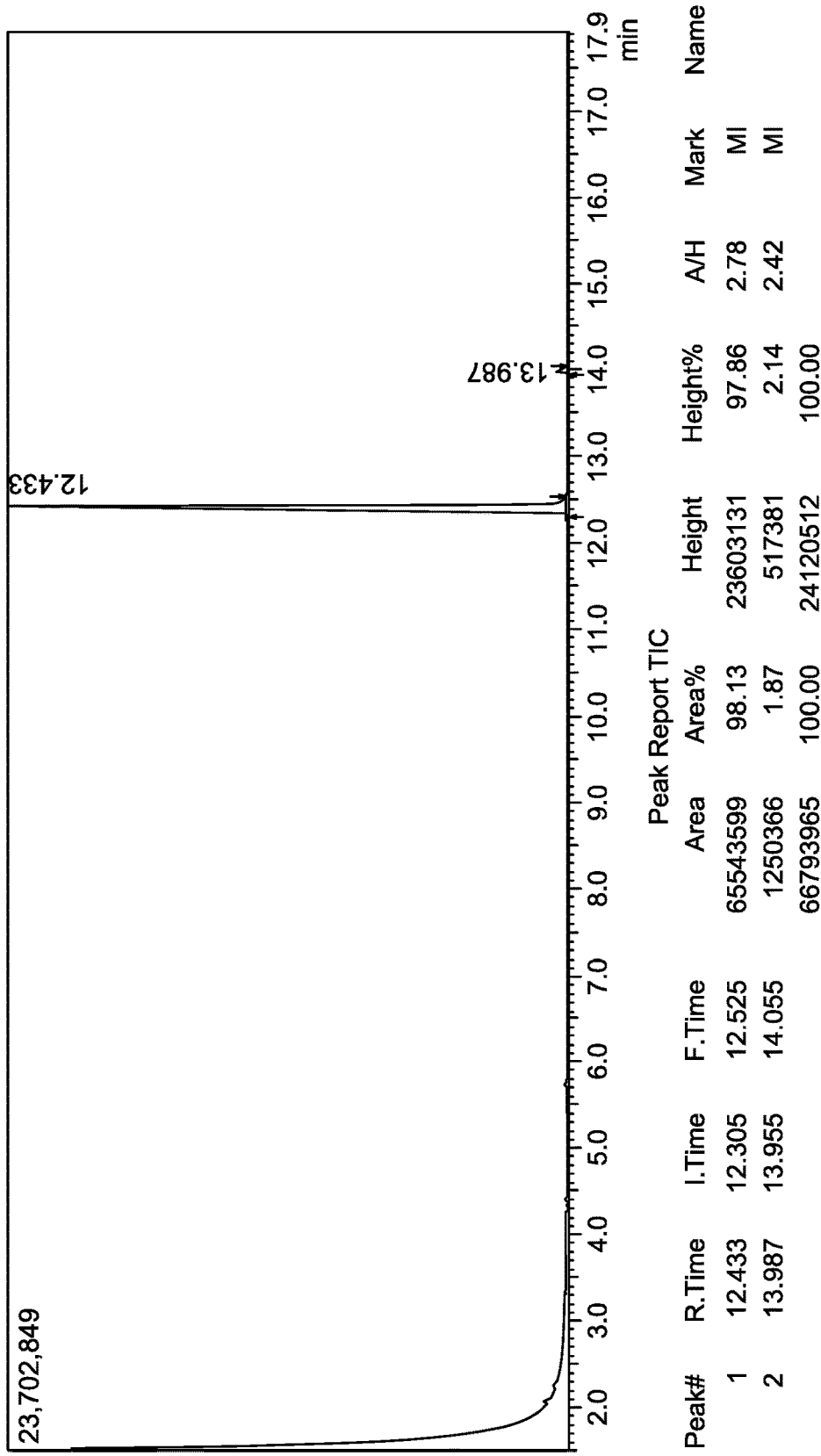
FIG. 21 is a gas chromatogram of the hydroformylated products of 4-methylstyrene formed in DCM at 45° C.
Figure 22:
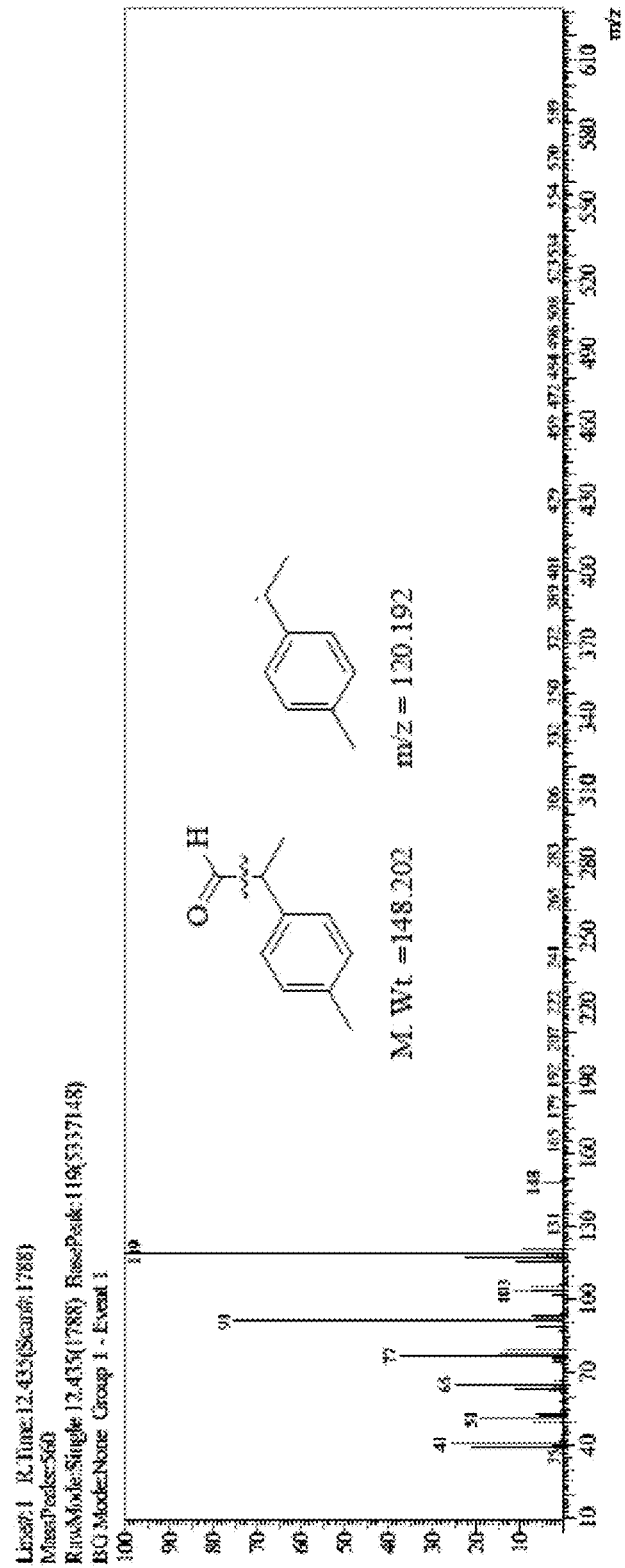
FIG. 22 is a mass spectrum of the branched aldehyde formed by hydroformylating 4-methylstyrene.
Figure 23:
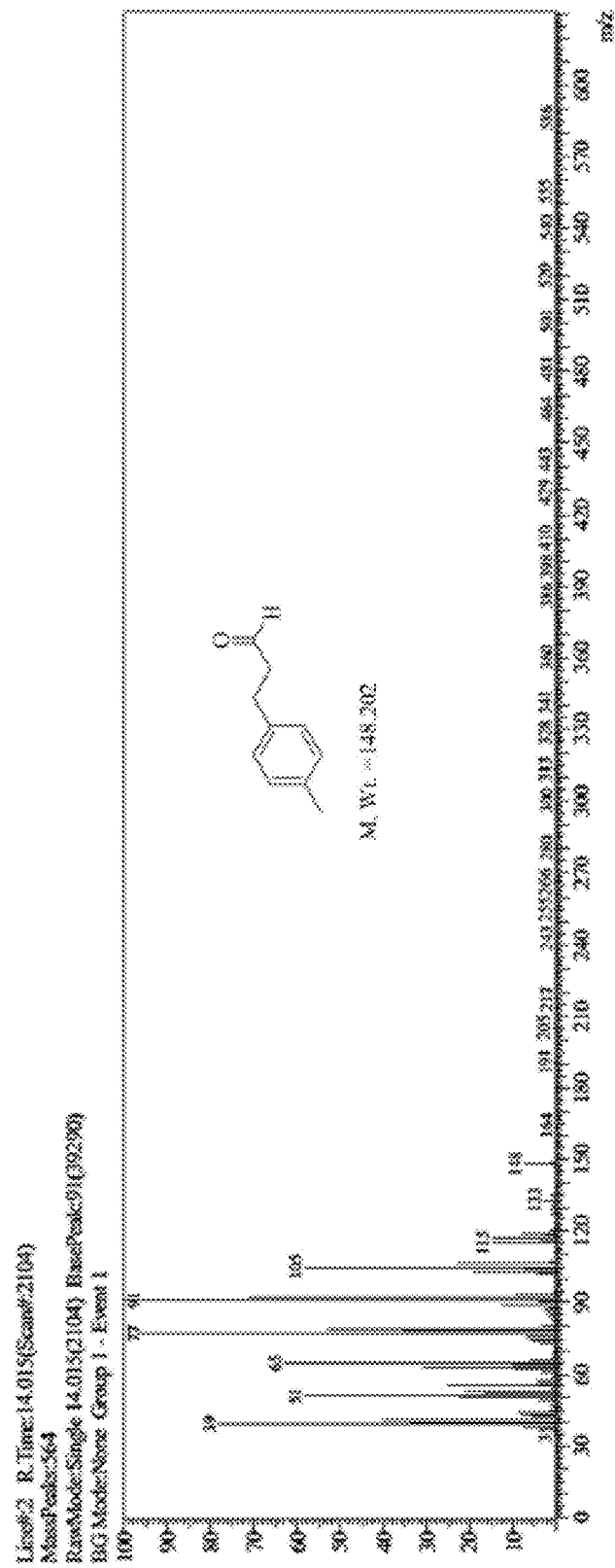
FIG. 23 is a mass spectrum of the linear aldehyde formed by hydroformylating 4-methylstyrene.
Figure 24:
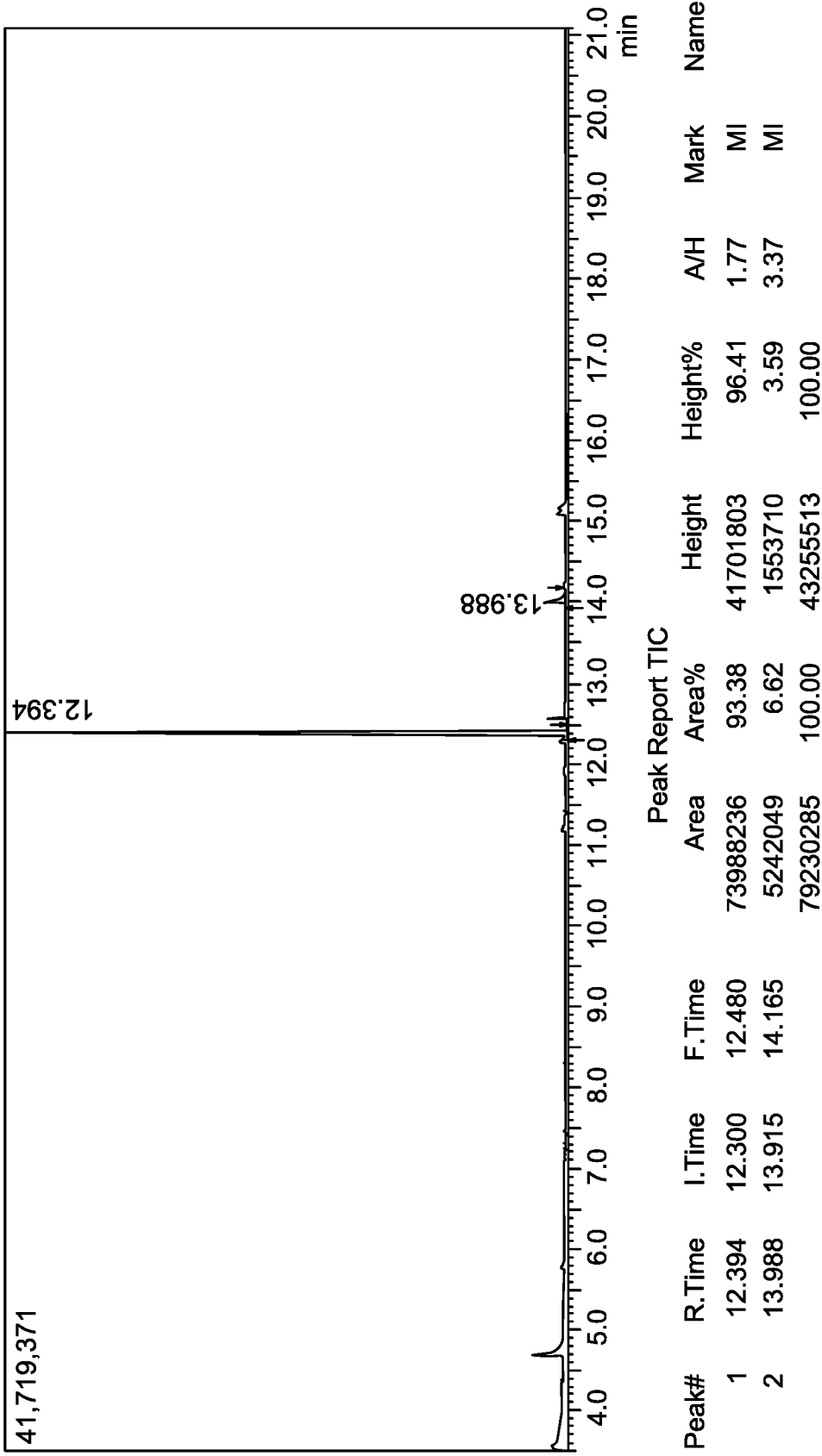
FIG. 24 is a gas chromatogram of the hydroformylated products of 4-methylstyrene formed in THF at 45° C.
Figure 25:
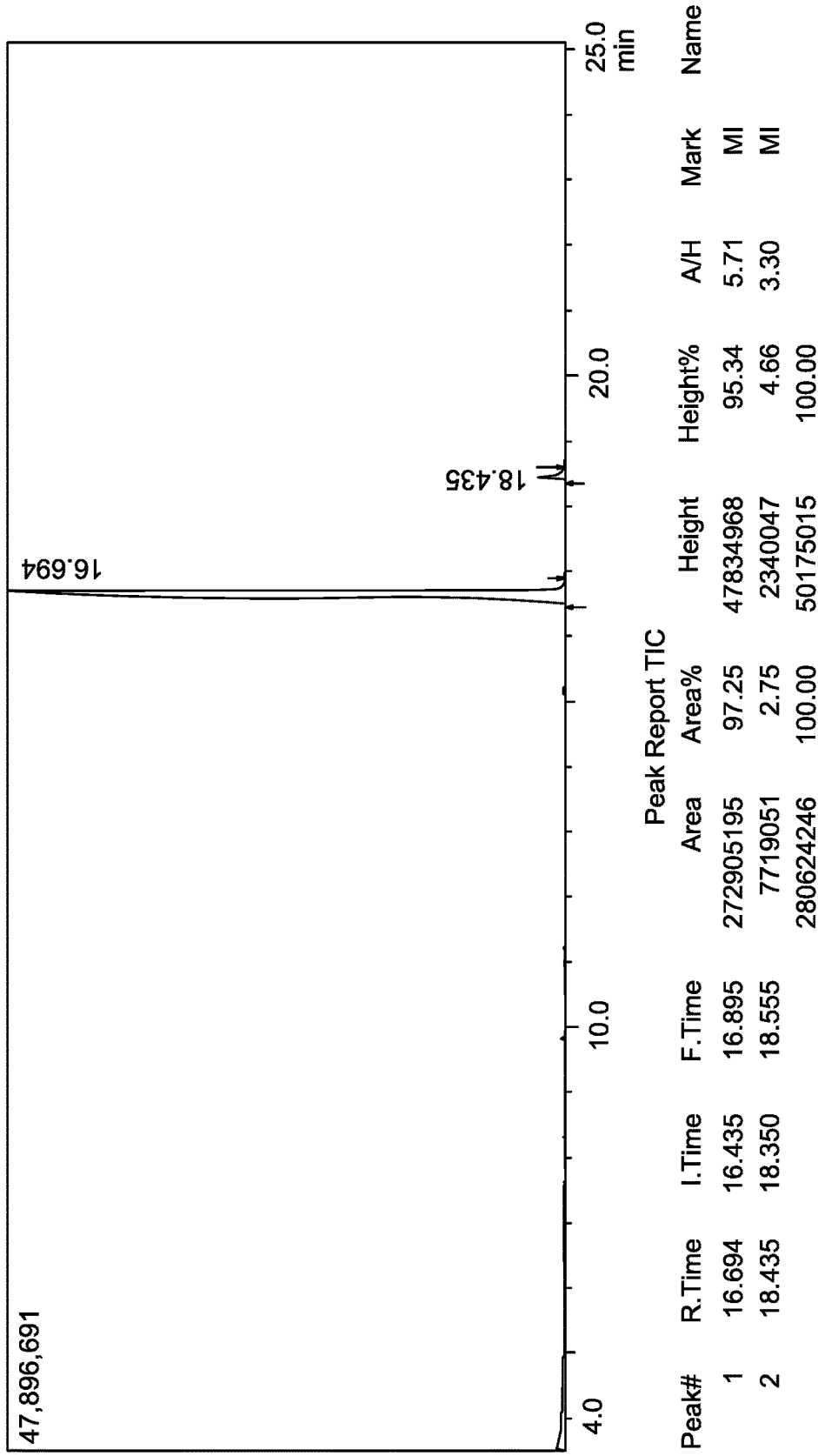
FIG. 25 is a gas chromatogram of the hydroformylated products of 4-vinylanisole formed in DCM at 45° C.
Figure 26:
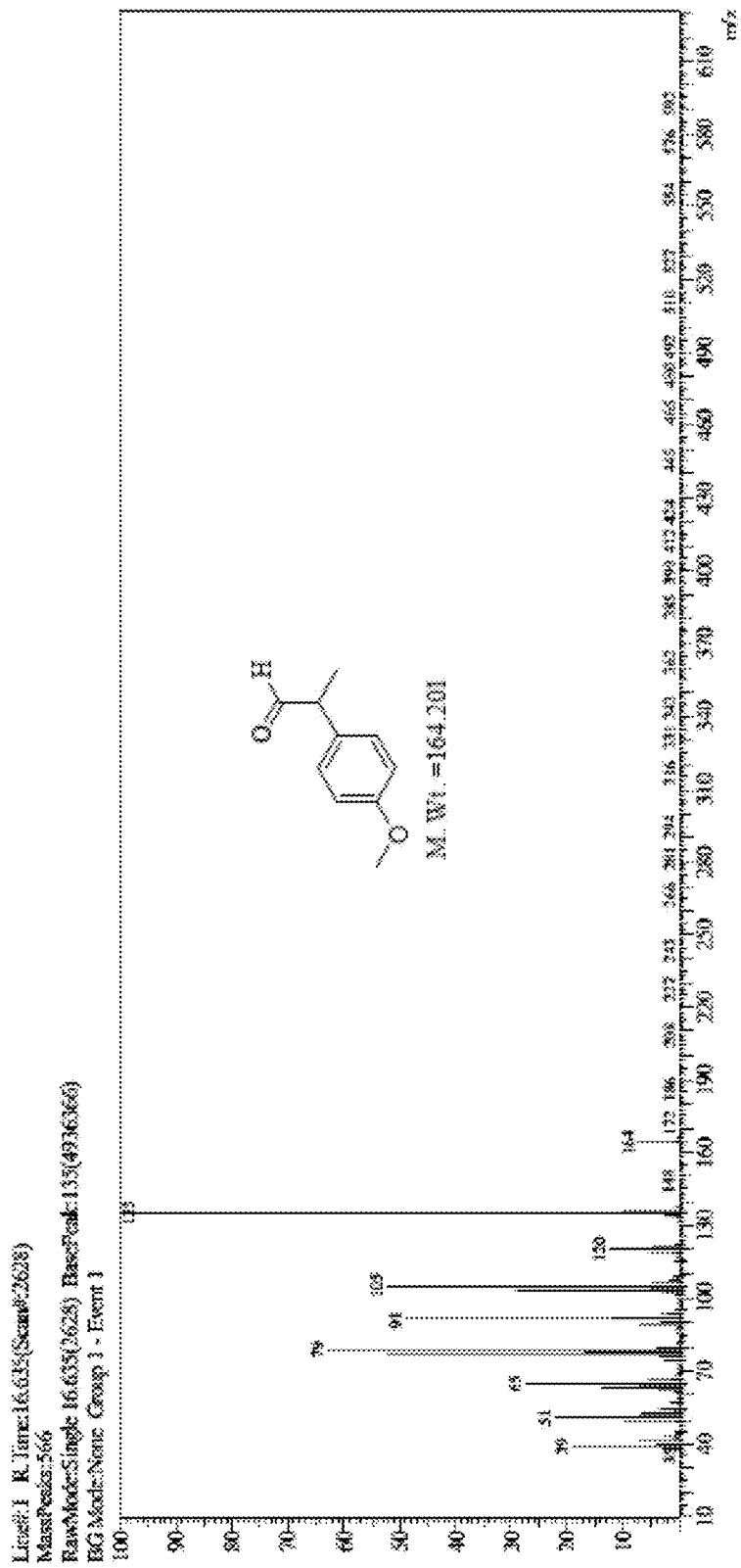
FIG. 26 is a mass spectrum of the branched aldehyde formed by hydroformylating 4-vinylanisole.
Figure 27:
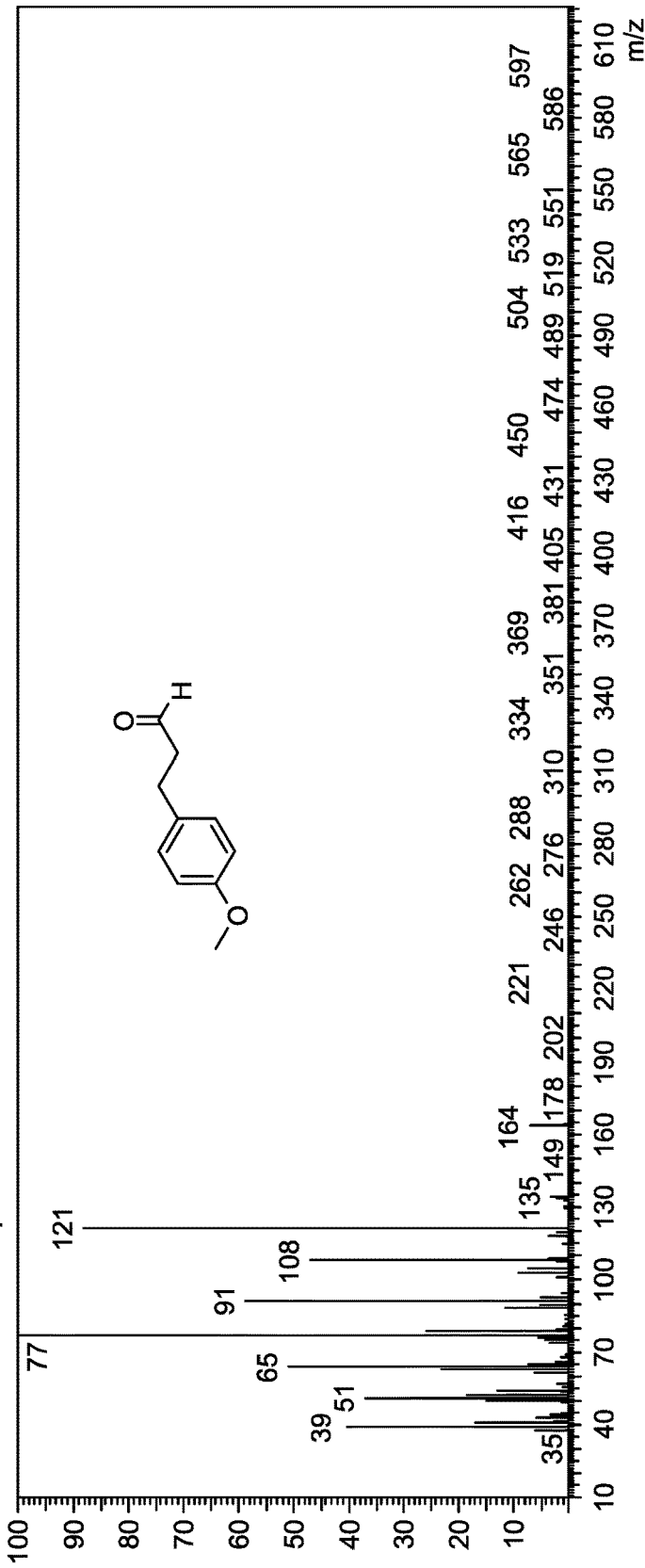
FIG. 27 is a mass spectrum of the linear aldehyde formed by hydroformylating 4-vinylanisole.
Figure 28:
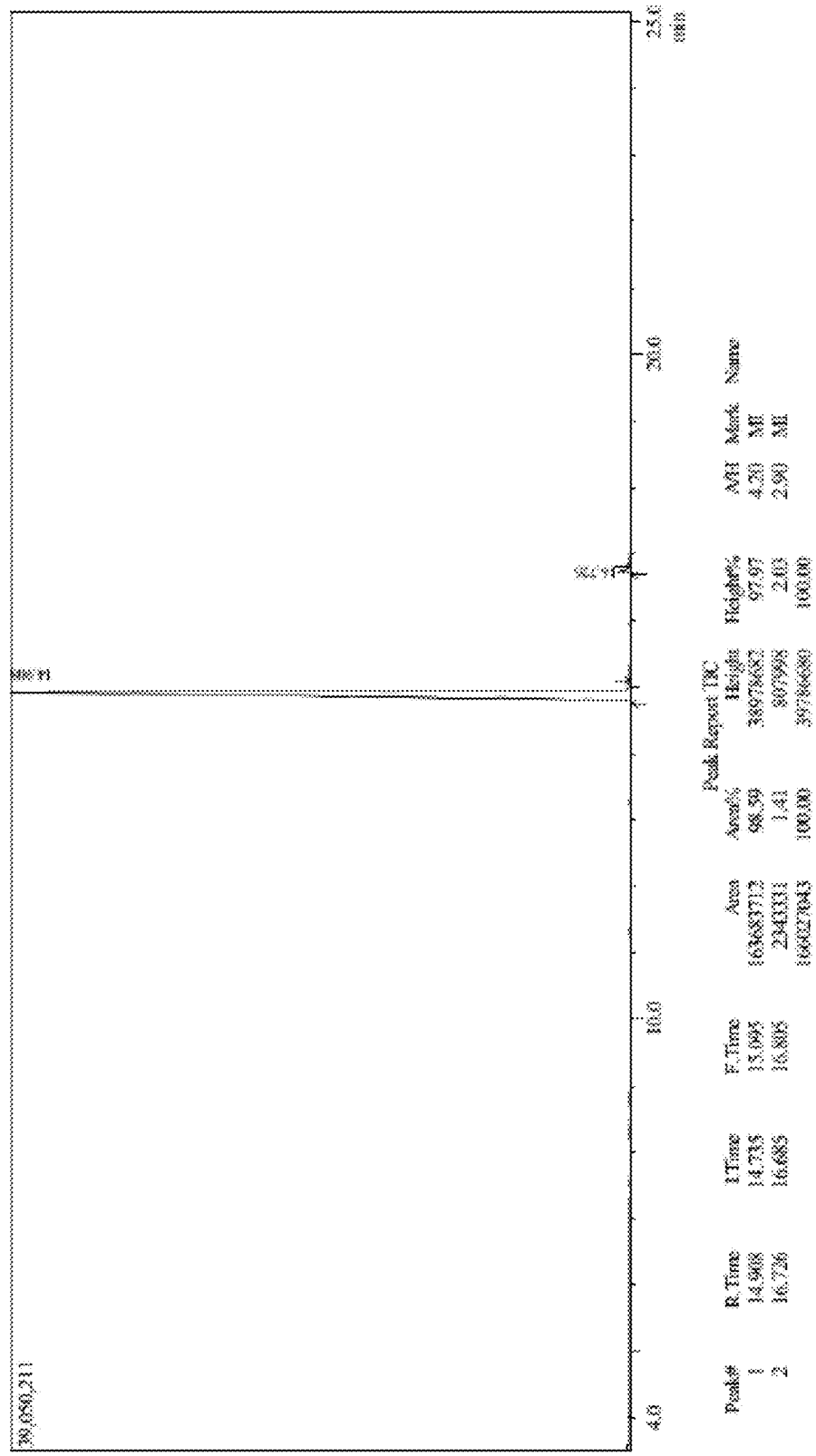
FIG. 28 is a gas chromatogram of the hydroformylated products of 4-chlorostyrene formed in DCM at 45° C.
Figure 29:
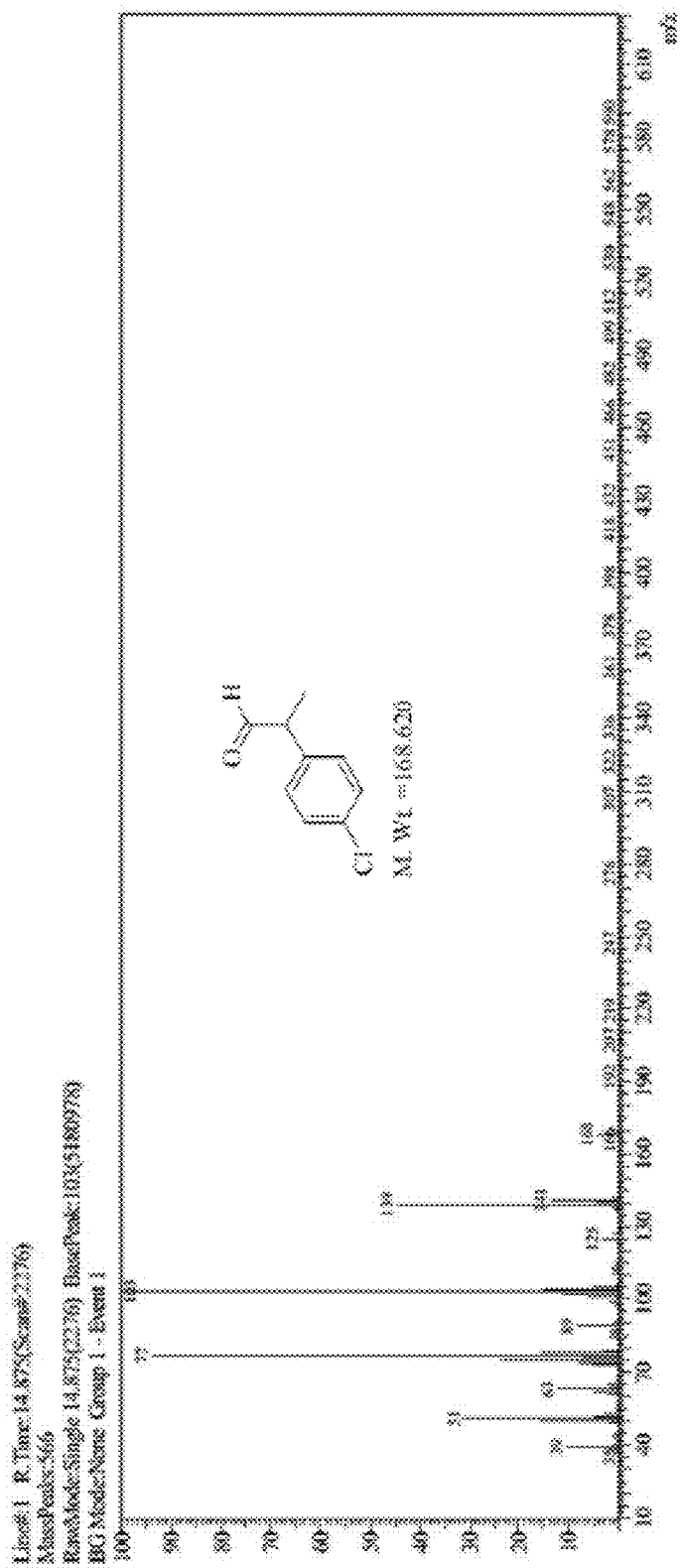
FIG. 29 is a mass spectrum of the branched aldehyde formed by hydroformylating 4-chlorostyrene.
Figure 30:
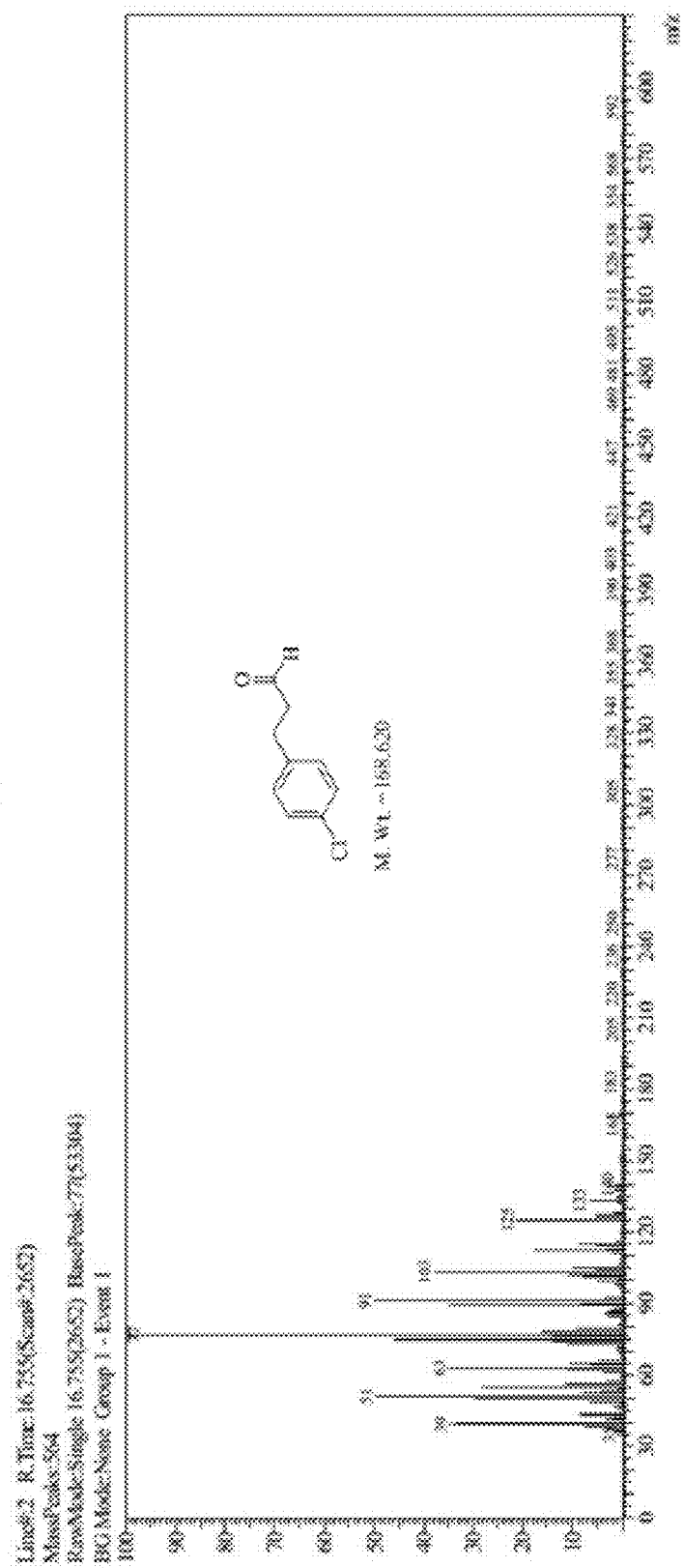
FIG. 30 is a mass spectrum of the linear aldehyde formed by hydroformylating 4-chlorostyrene.
Figure 31:
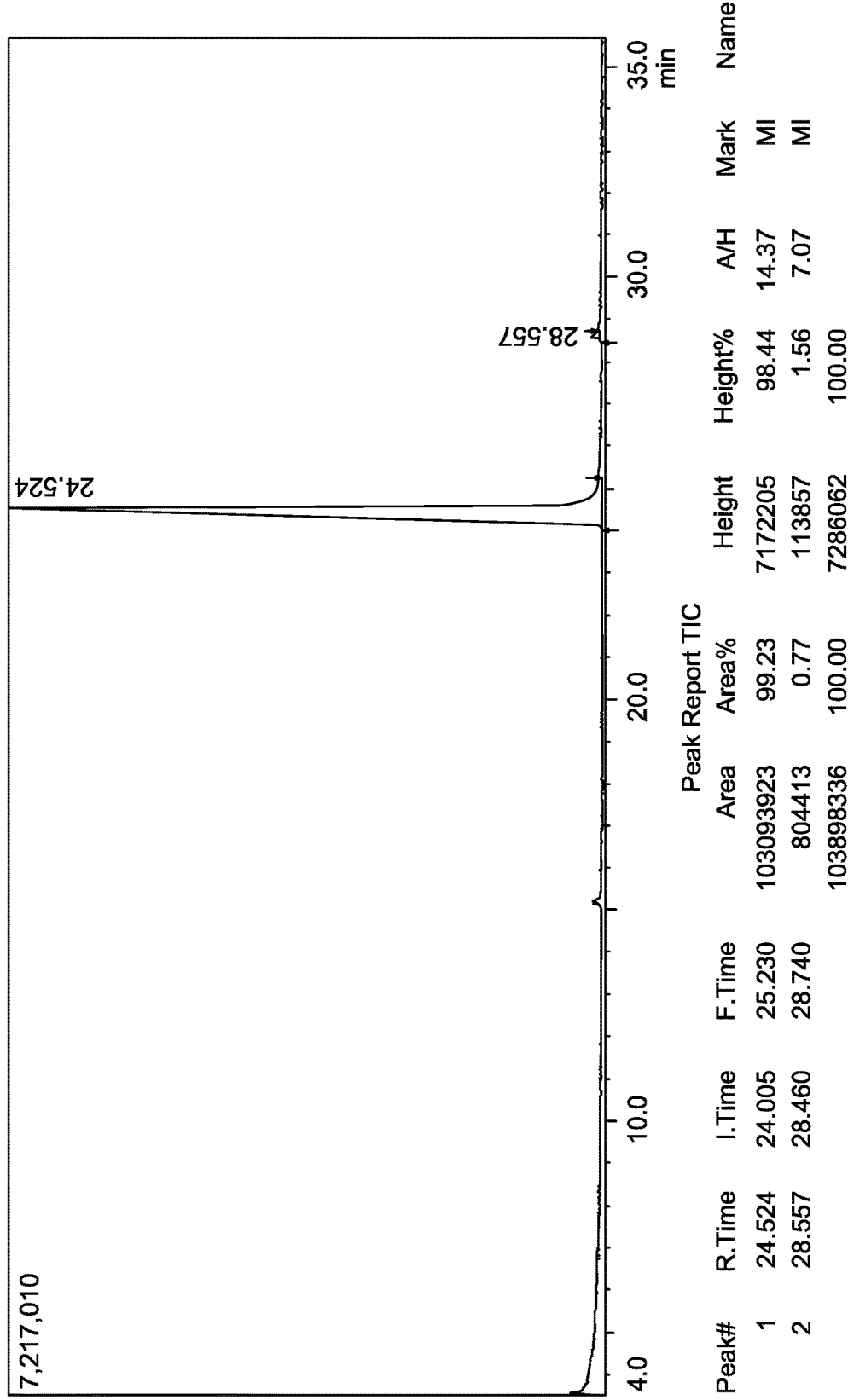
FIG. 31 is a gas chromatogram of the hydroformylated products of 3-nitrostyrene formed in DCM at 45° C.
Figure 32:
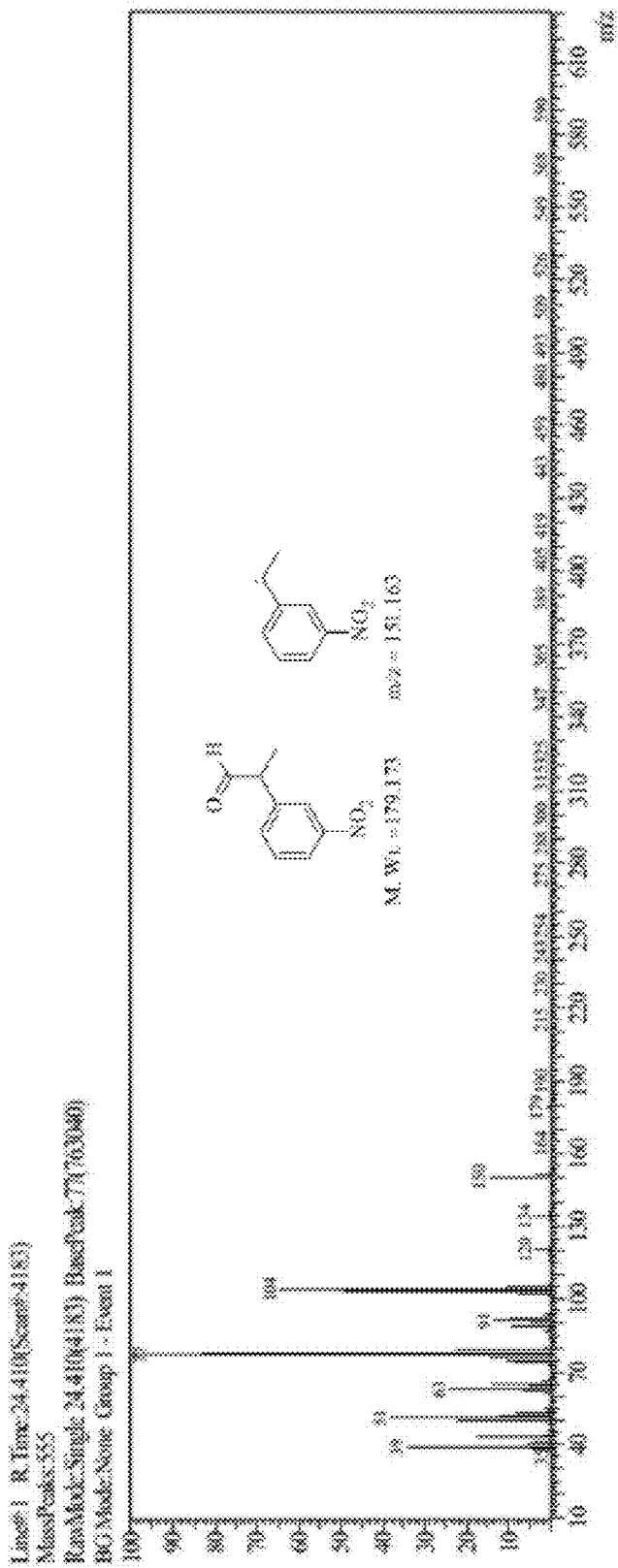
FIG. 32 is a mass spectrum of the branched aldehyde formed by hydroformylating 3-nitrostyrene.
Figure 33:
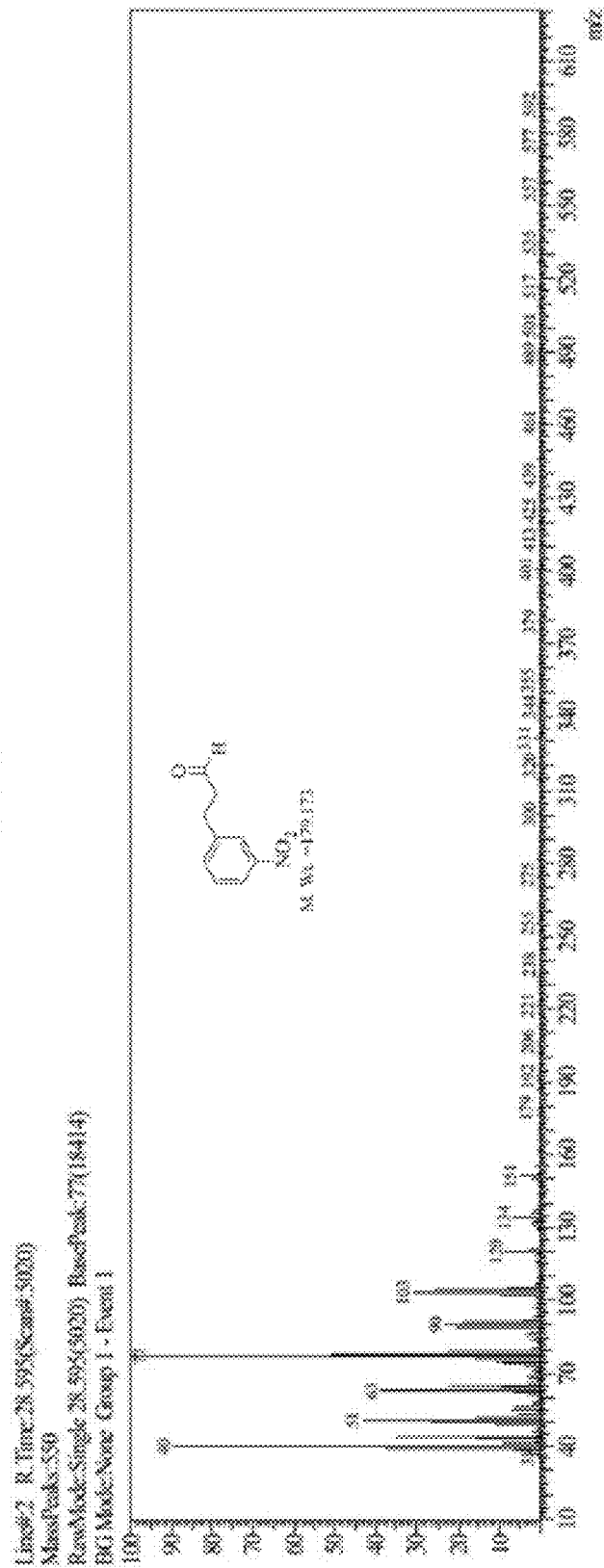
FIG. 33 is a mass spectrum of the linear aldehyde formed by hydroformylating 3-nitrostyrene.
Figure 34:
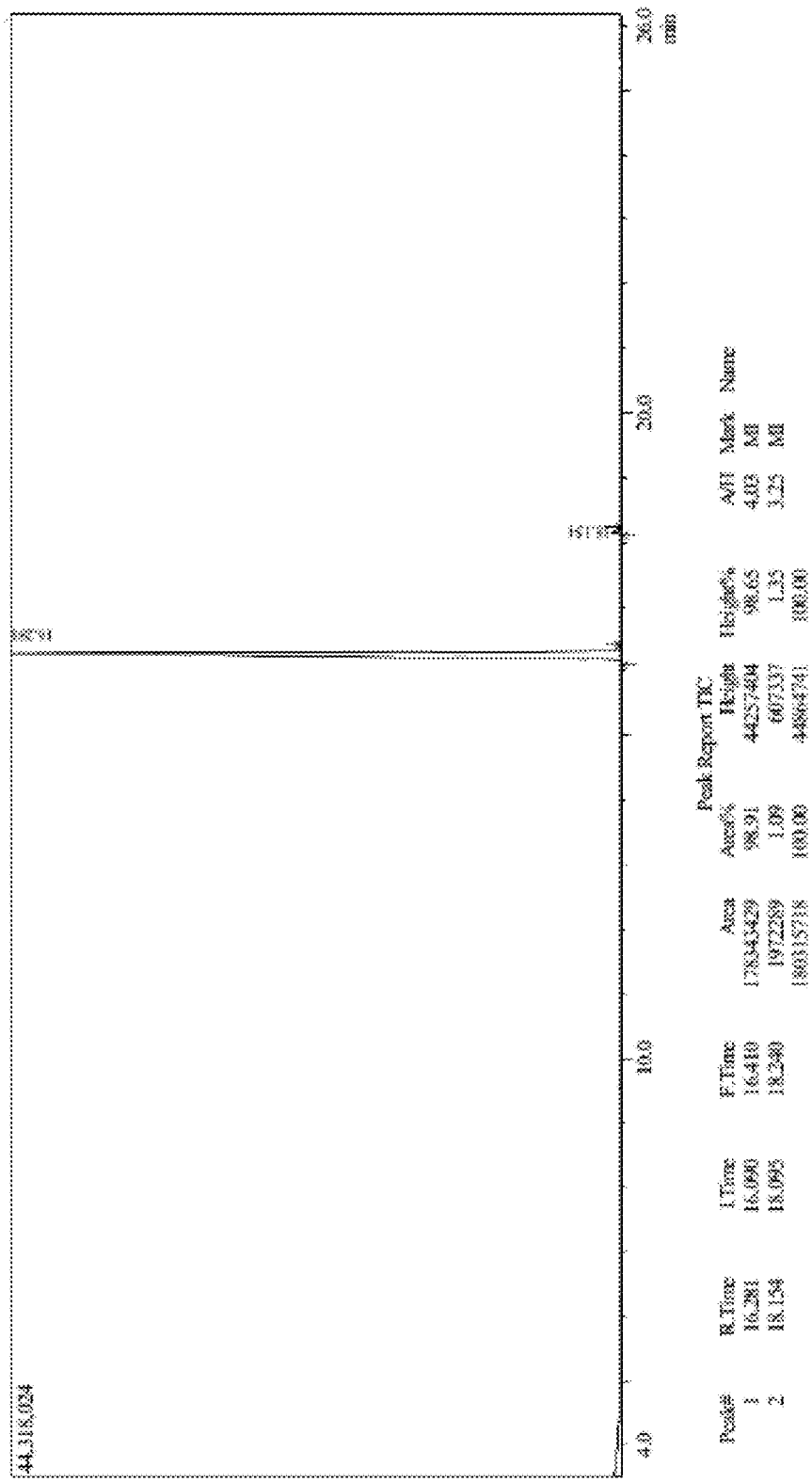
FIG. 34 is a gas chromatogram of the hydroformylated products of 2-bromostyrene formed in DCM at 45° C.
Figure 35:
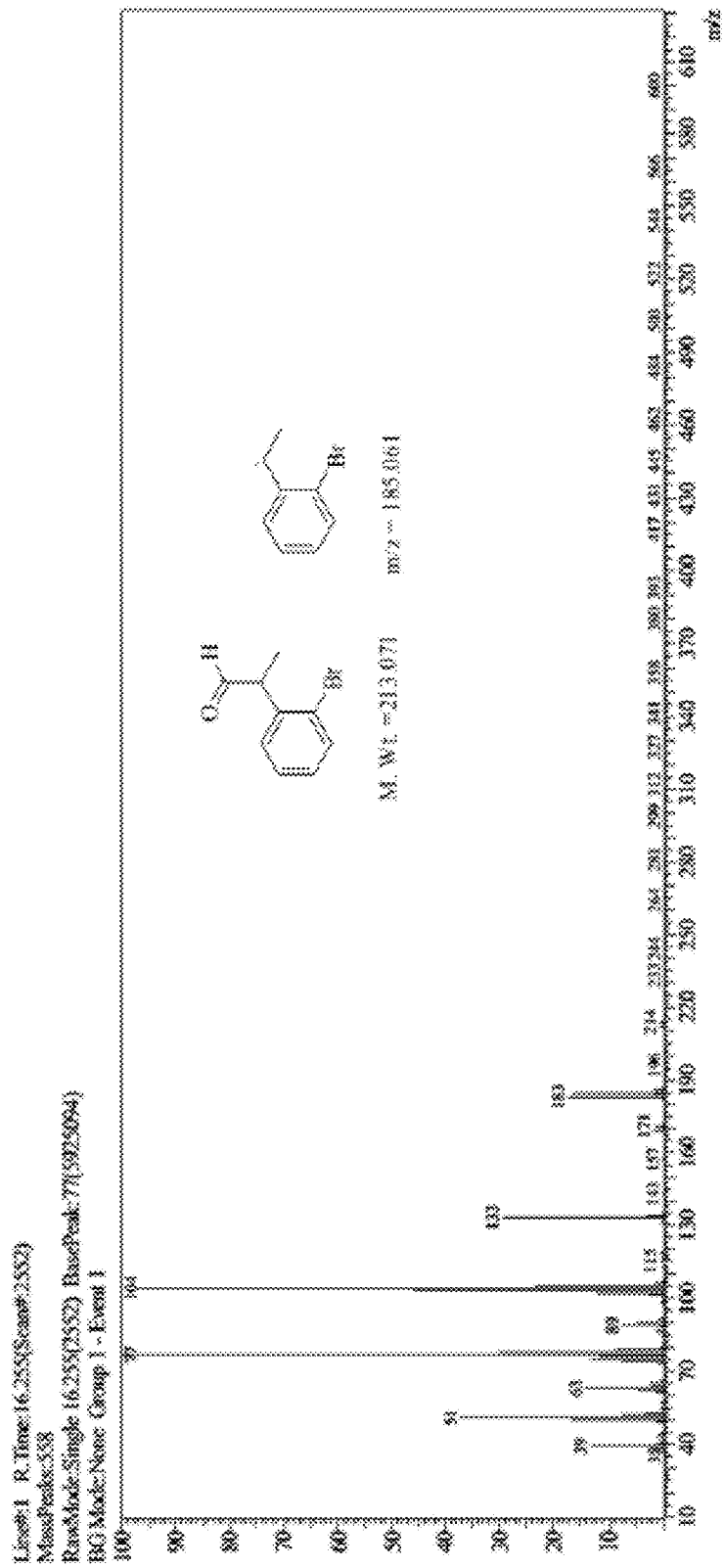
FIG. 35 is a mass spectrum of the branched aldehyde formed by hydroformylating 2-bromostyrene.
Figure 36:
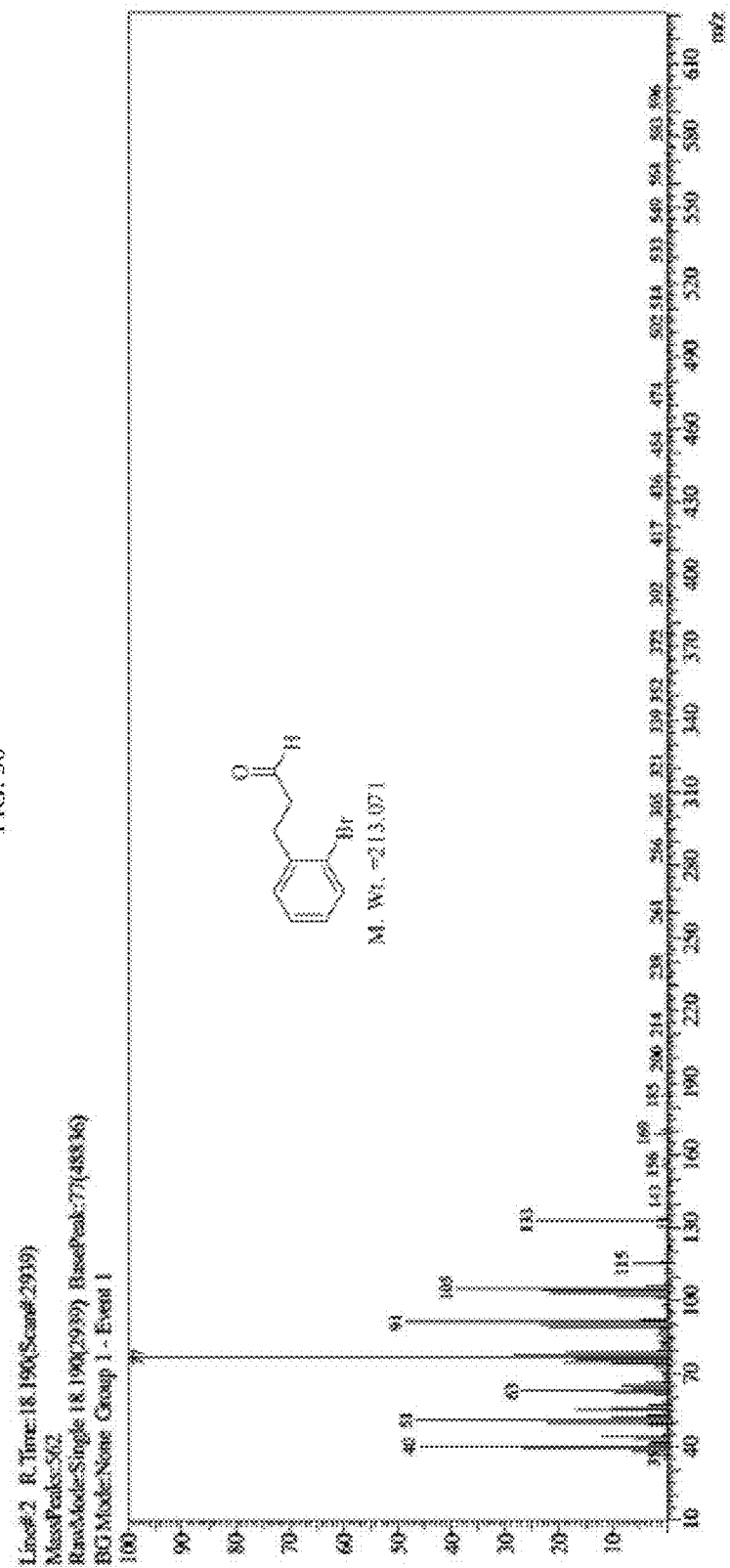
FIG. 36 is a mass spectrum of the linear aldehyde formed by hydroformylating 2-bromostyrene.
Figure 37:
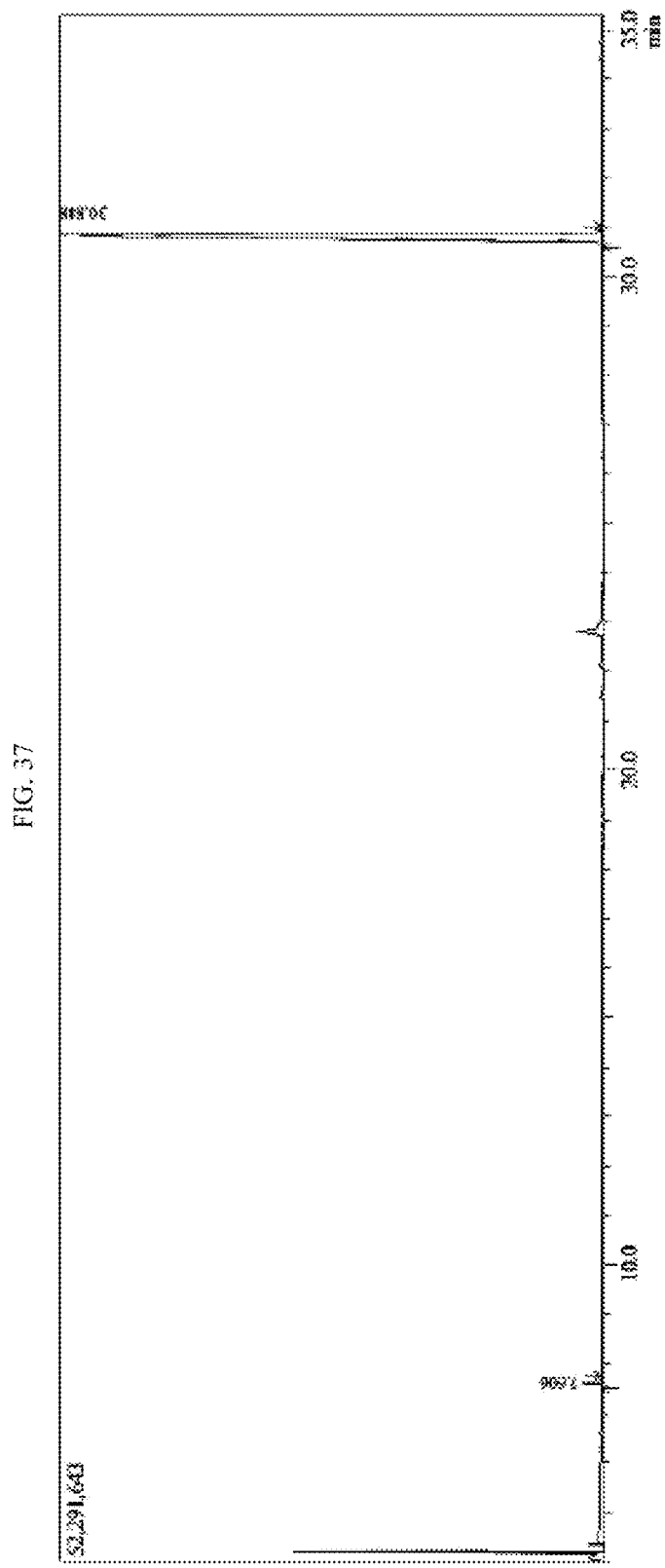
FIG. 37 is a gas chromatogram of the Mizoroki-Heck reaction product of styrene and iodobenzene formed at 95° C.
Figure 38:
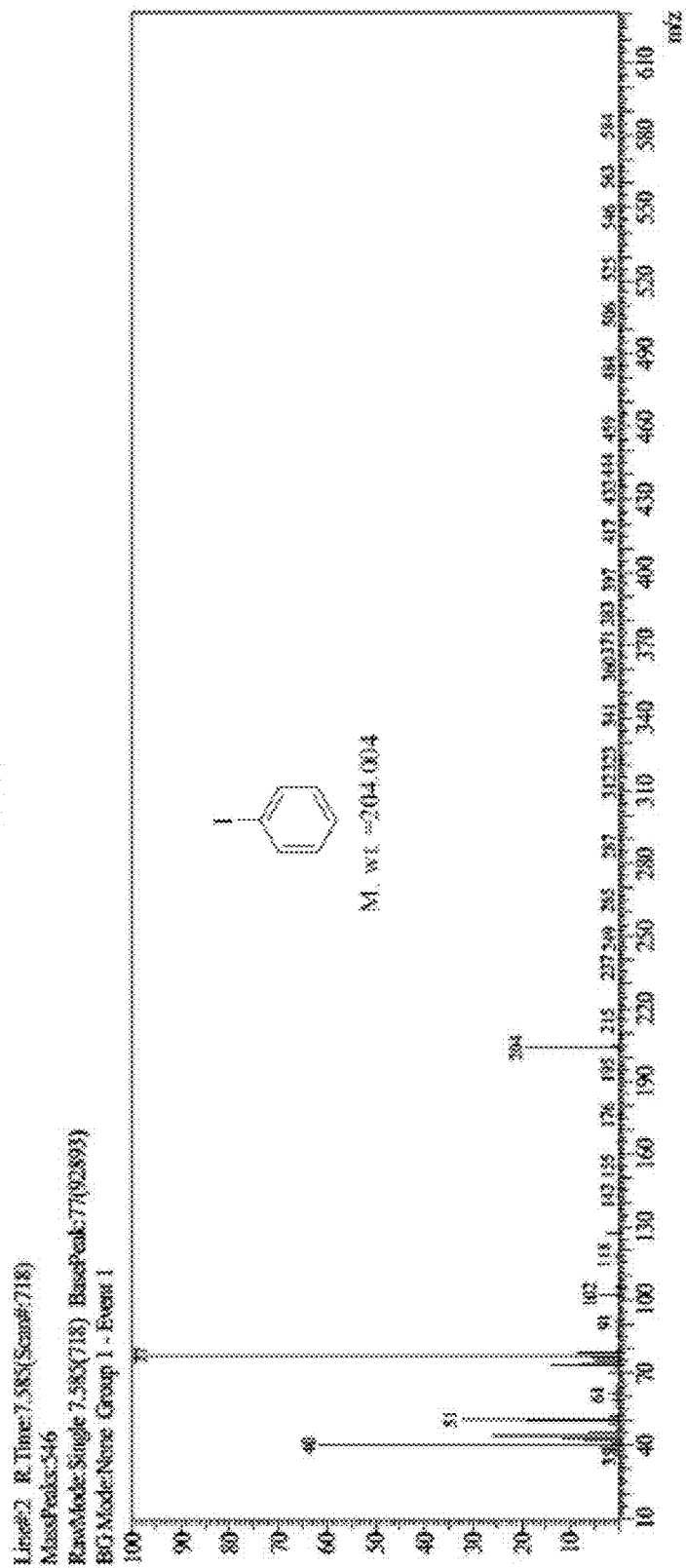
FIG. 38 is a mass spectrum of iodobenzene at Rt=7.585 minutes.
Figure 39:
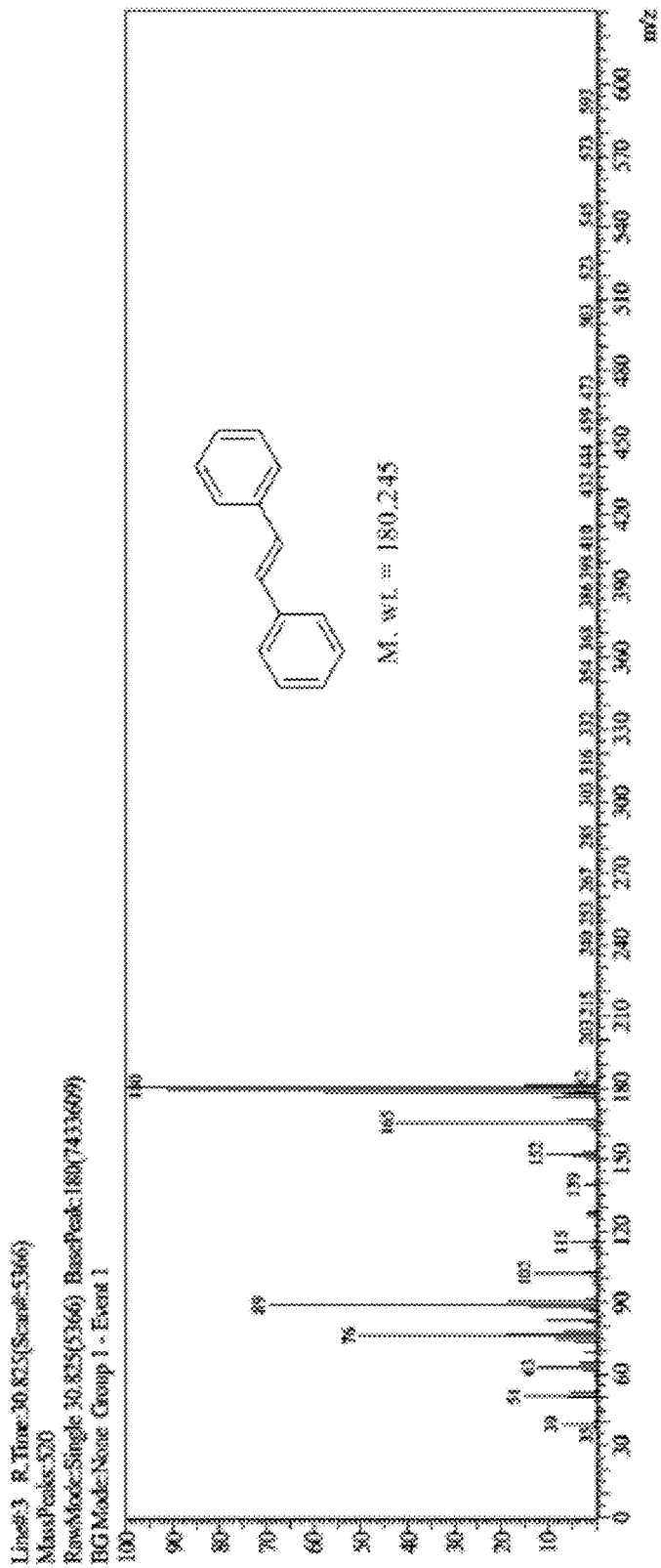
FIG. 39 is a mass spectrum of the coupling reaction product of styrene and iodobenzene.
Figure 40:
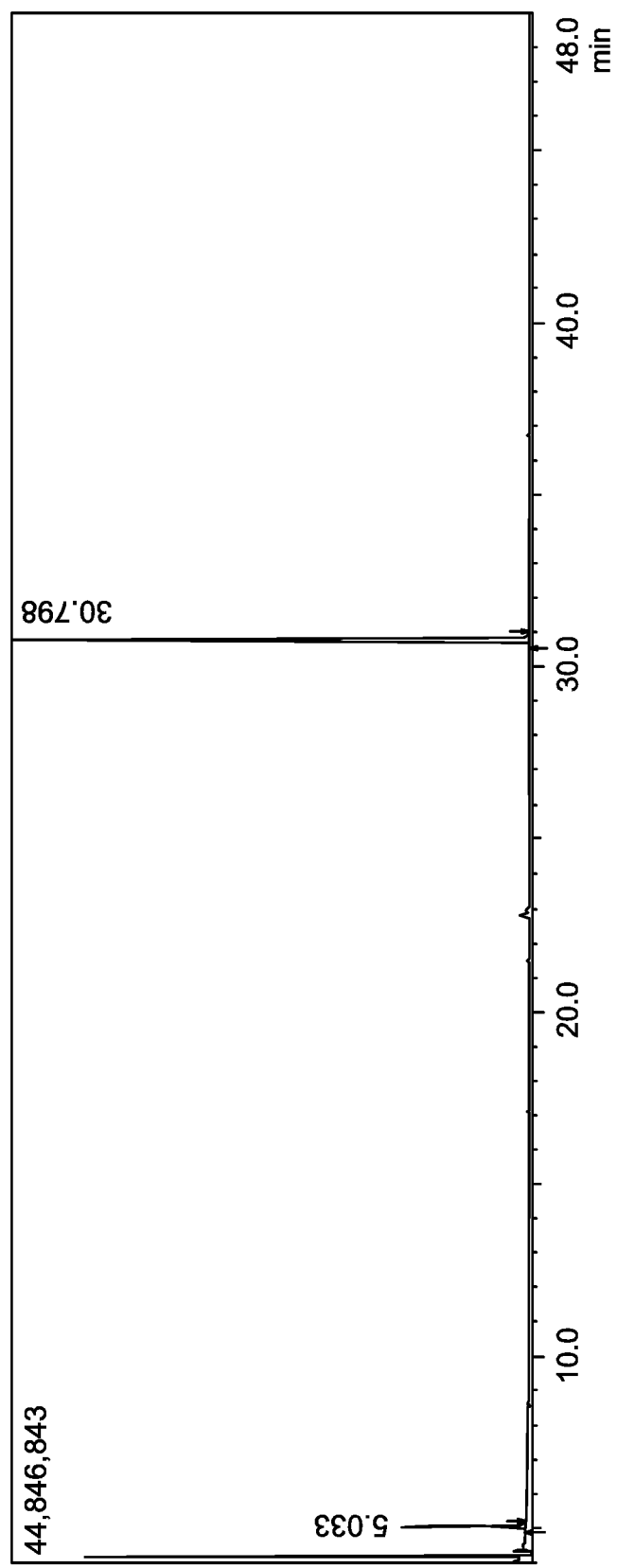
FIG. 40 is a gas chromatogram of the Mizoroki-Heck reaction product of styrene and bromobenzene formed at 95° C. after 1 hour.
Figure 41:
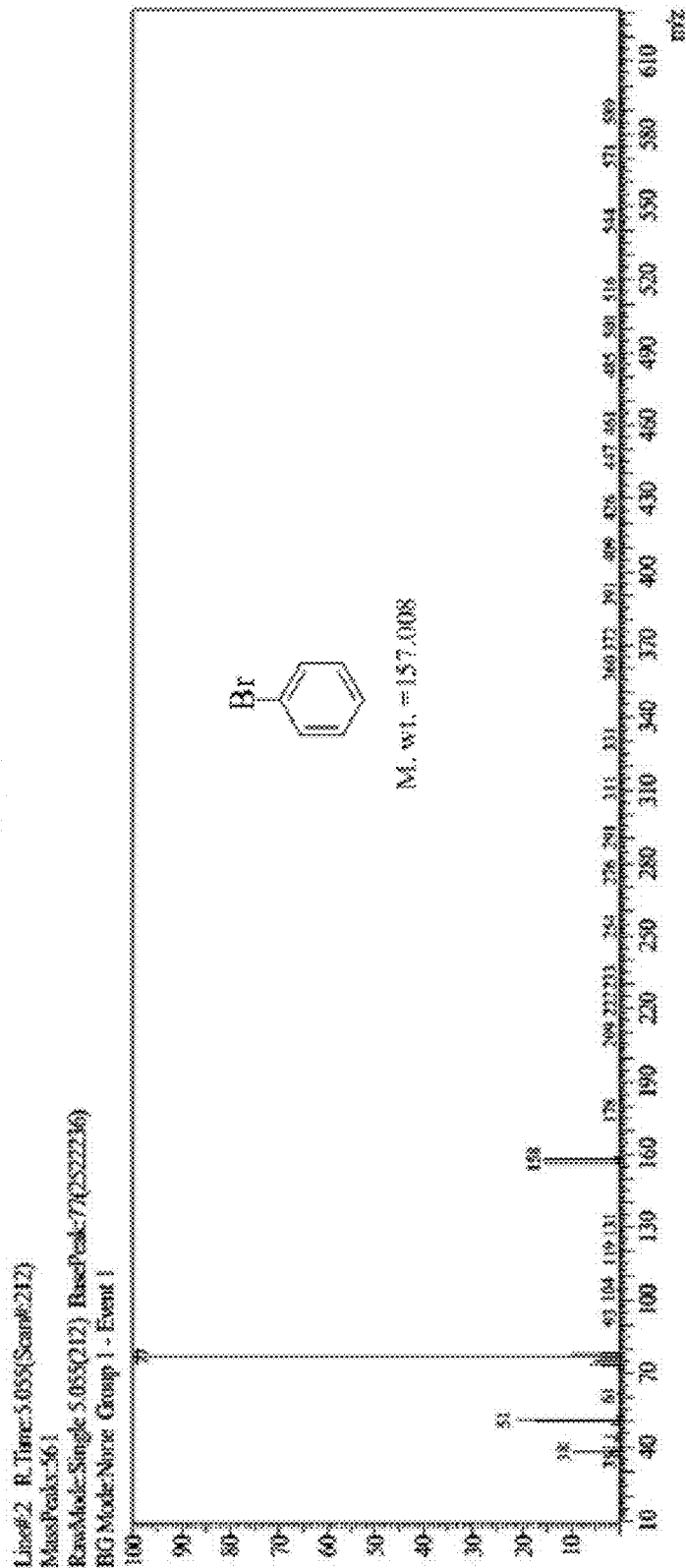
FIG. 41 is a mass spectrum of bromobenzene at Rt=5.055 minutes.
Figure 42:
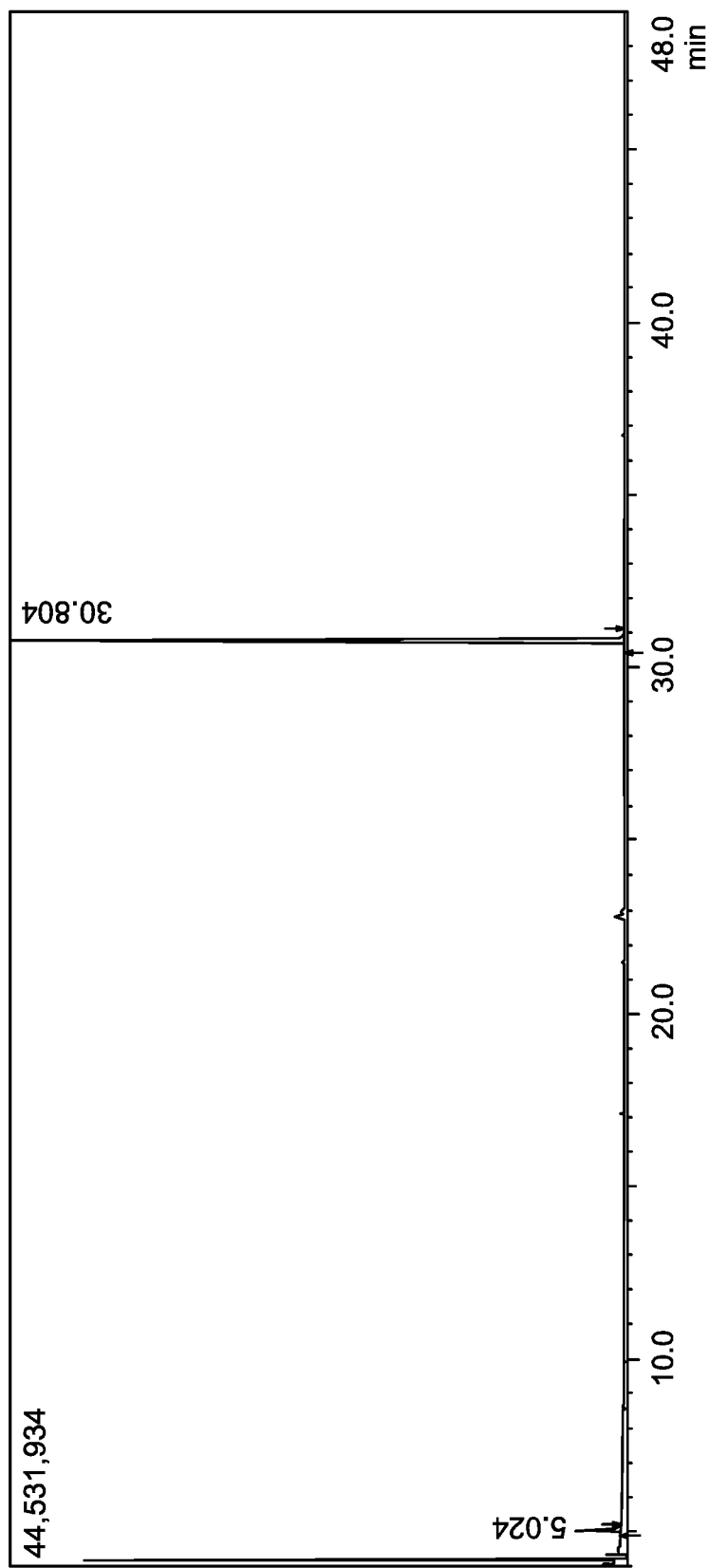
FIG. 42 is a gas chromatogram of the Mizoroki-Heck reaction product of styrene and bromobenzene formed at 95° C. after 2 hours.
Figure 43:
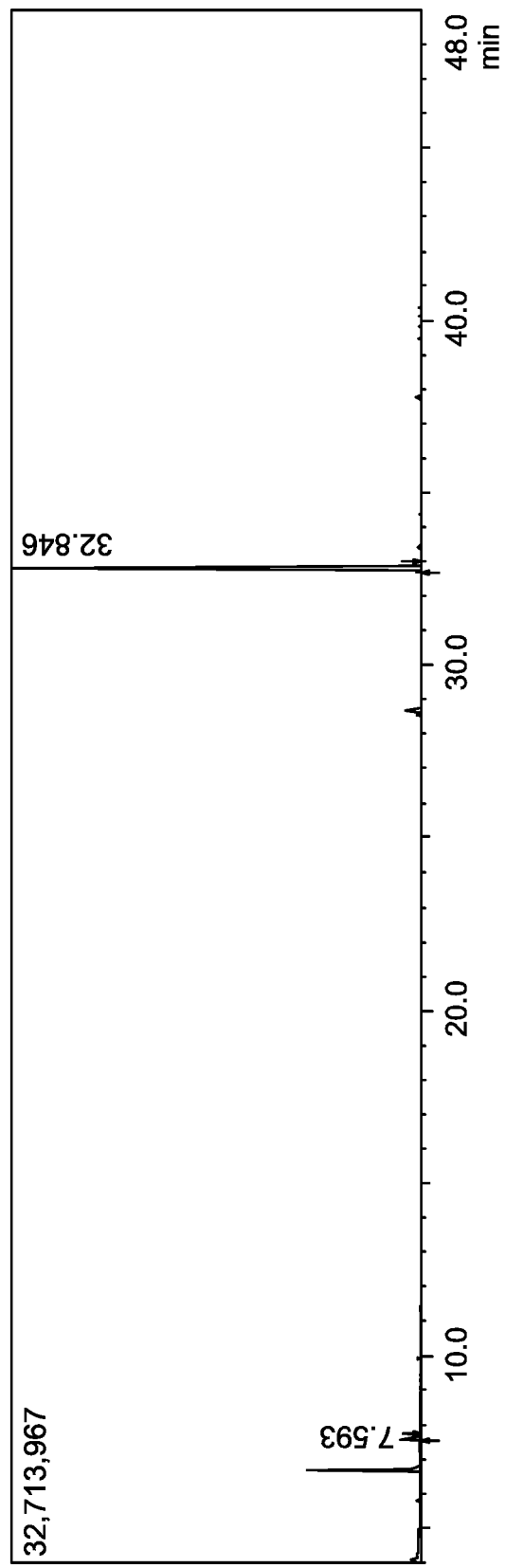
FIG. 43 is a gas chromatogram of the Mizoroki-Heck reaction product of 4-methylstyrene and iodobenzene formed at 95° C.
Figure 44:
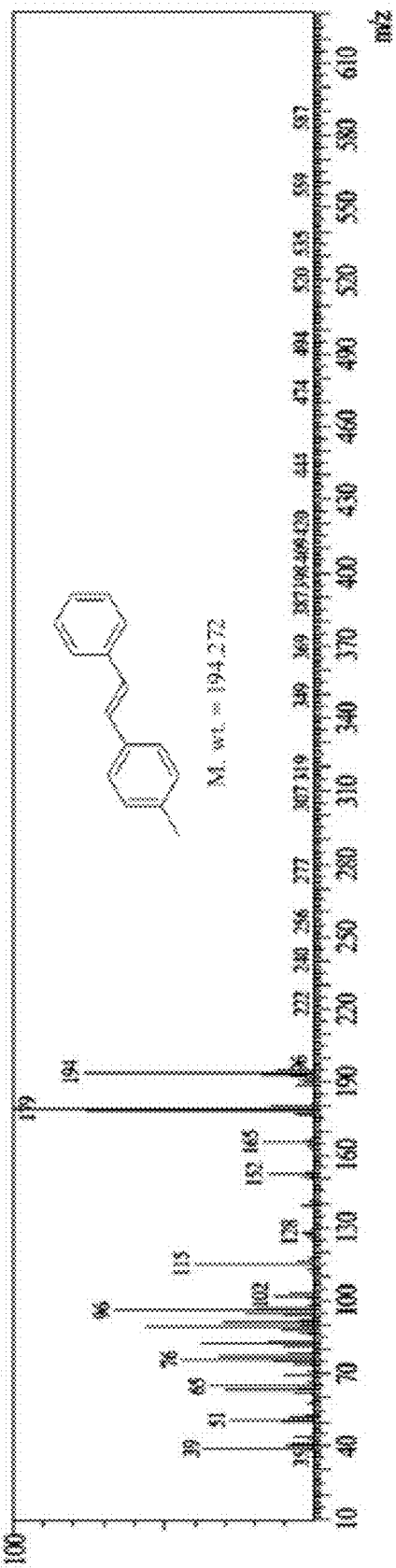
FIG. 44 is a mass spectrum of the Mizoroki-Heck reaction product of 4-methylstyrene.
Figure 45:
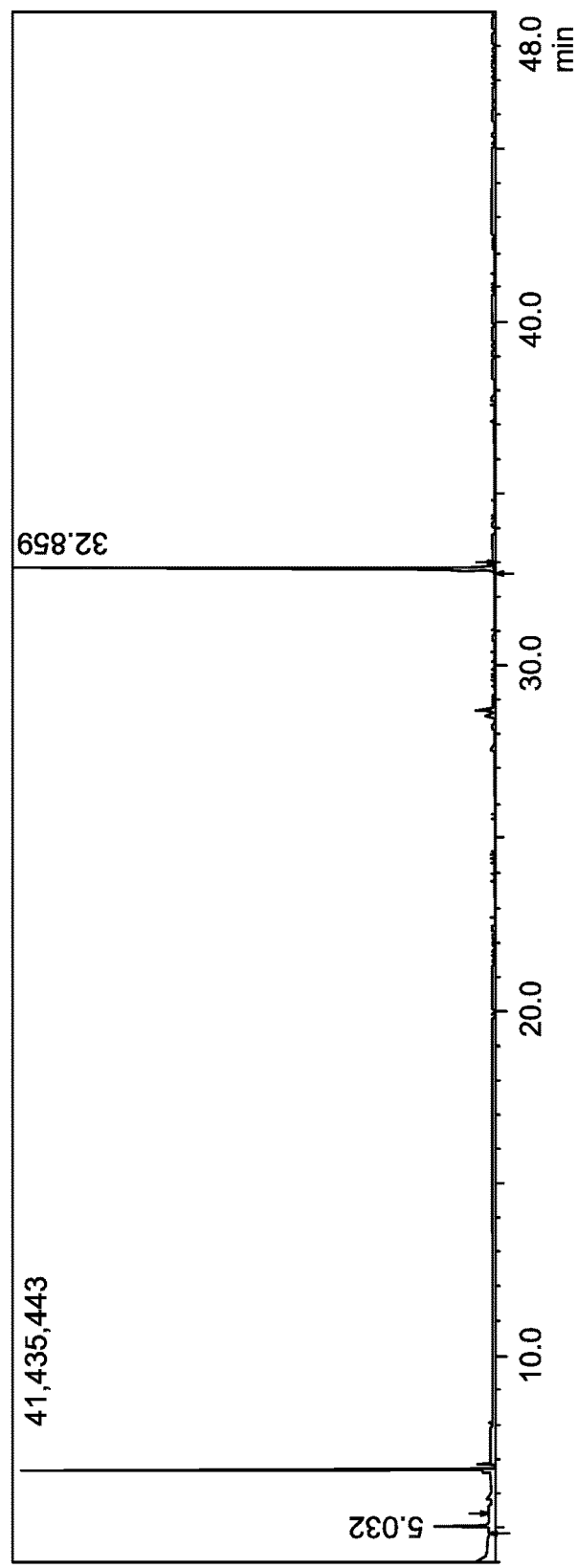
FIG. 45 is a gas chromatogram of the Mizoroki-Heck reaction product of 4-methylstyrene and bromobenzene formed at 95° C. after 30 minutes.
Figure 46:
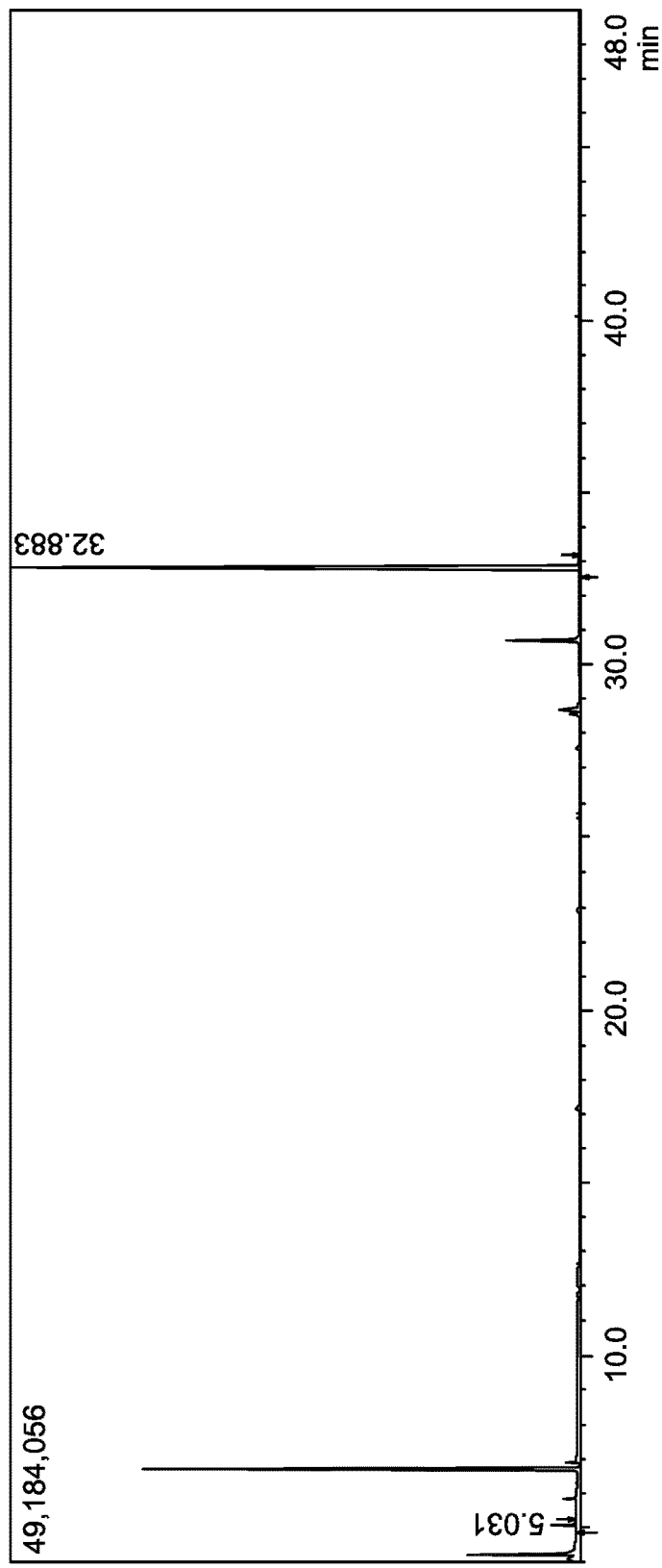
FIG. 46 is a gas chromatogram of the Mizoroki-Heck reaction product of 4-methylstyrene and bromobenzene formed at 95° C. after 2 hours.
Figure 47:
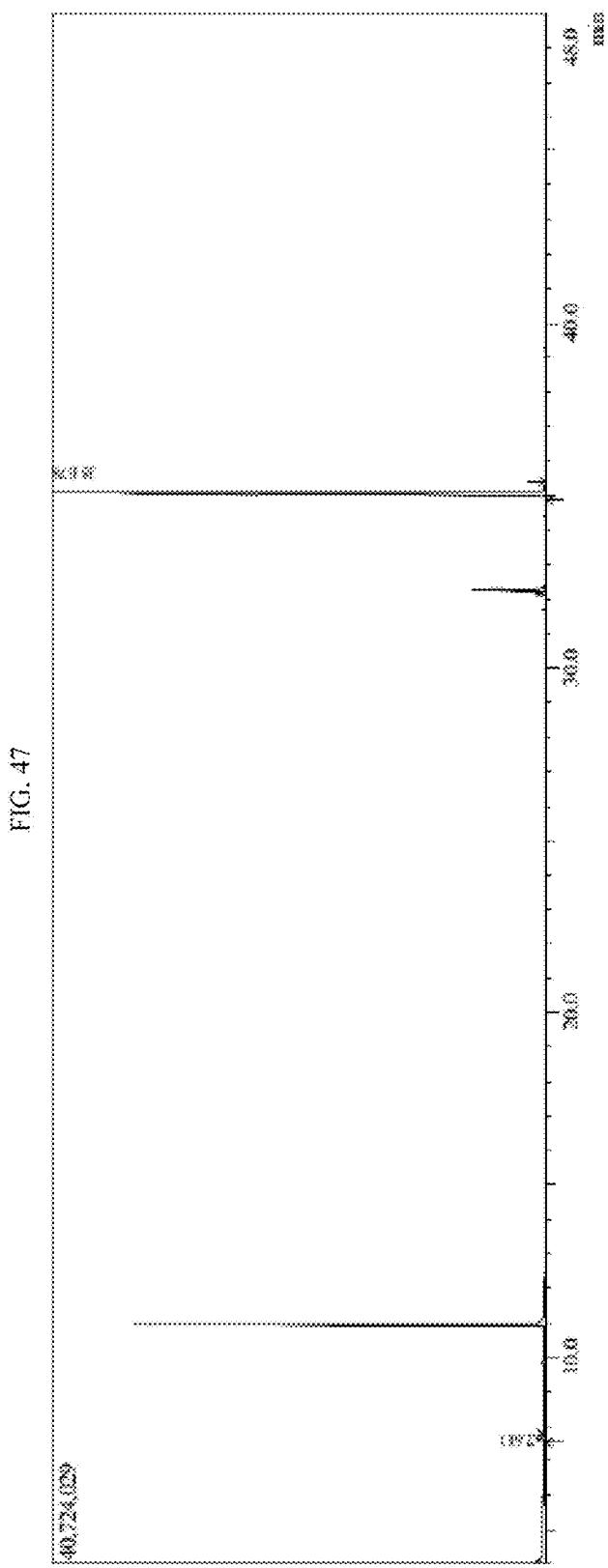
FIG. 47 is a gas chromatogram of the Mizoroki-Heck reaction product of 4-vinylanisole and iodobenzene formed at 95° C. after 30 minutes.
Figure 48:
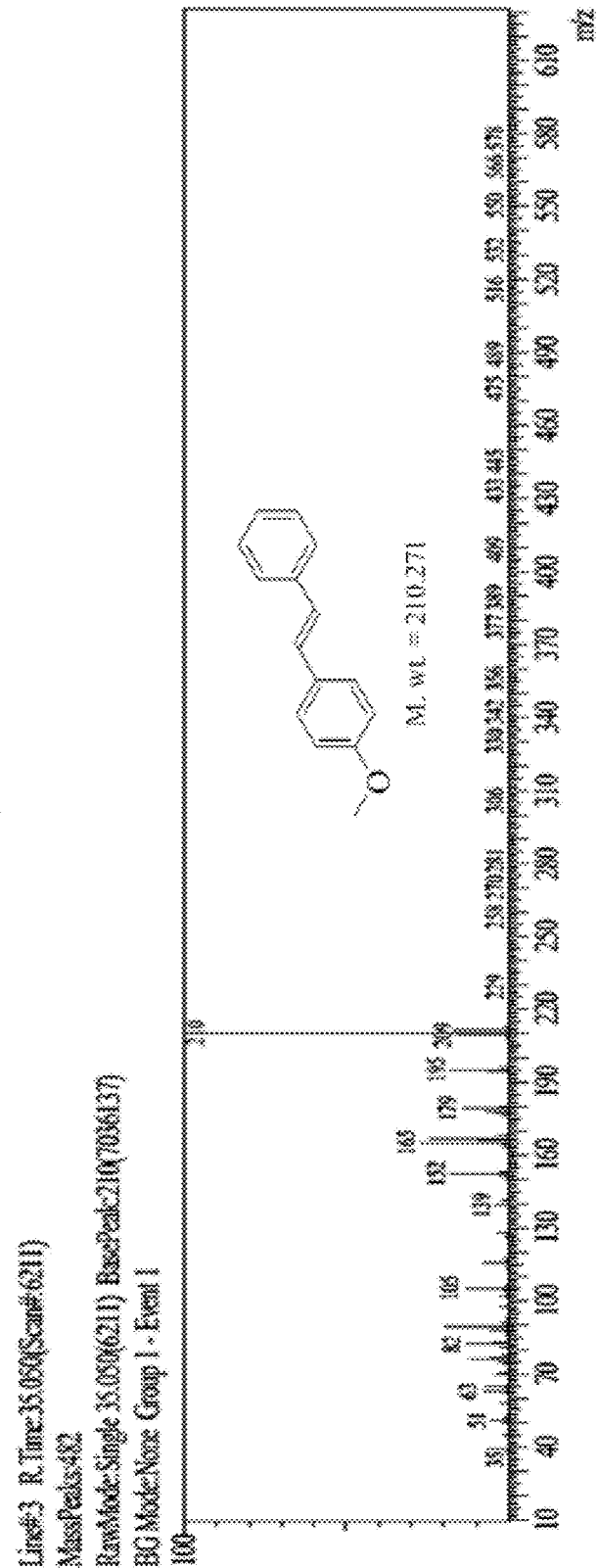
FIG. 48 is a mass spectrum of the Mizoroki-Heck coupling reaction product of 4-vinylanisole.
Figure 49:
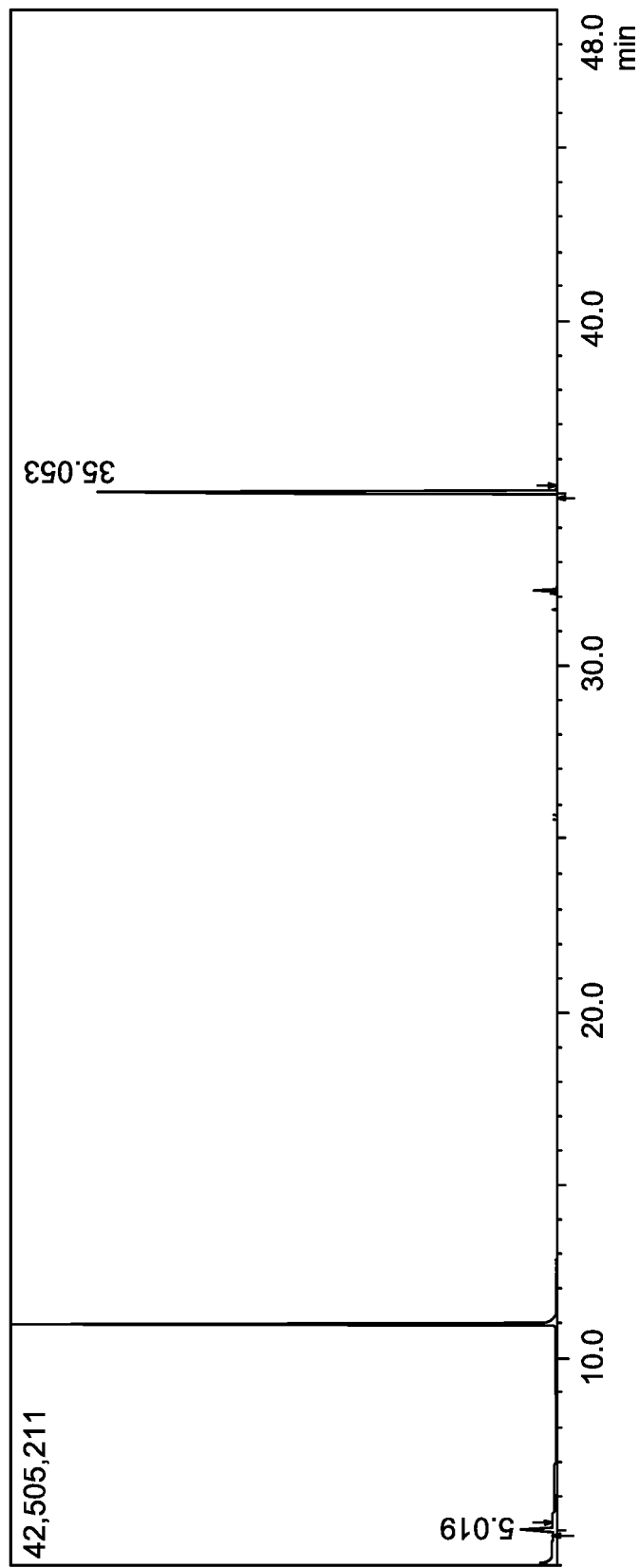
FIG. 49 is a gas chromatogram of the Mizoroki-Heck reaction product of 4-vinylanisole and bromobenzene formed at 95° C. after 1 hour.
Figure 50:
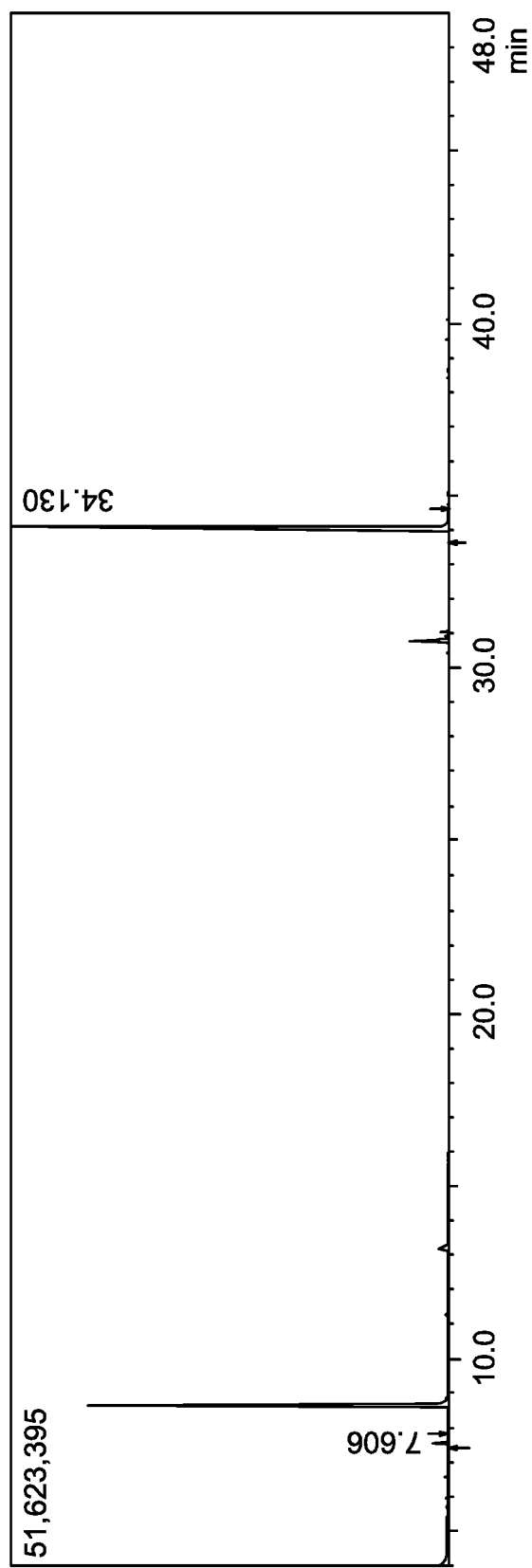
FIG. 50 is a gas chromatogram of the Mizoroki-Heck reaction product of 4-chlorostyrene and iodobenzene formed at 95° C. after 30 minutes.
Figure 51:
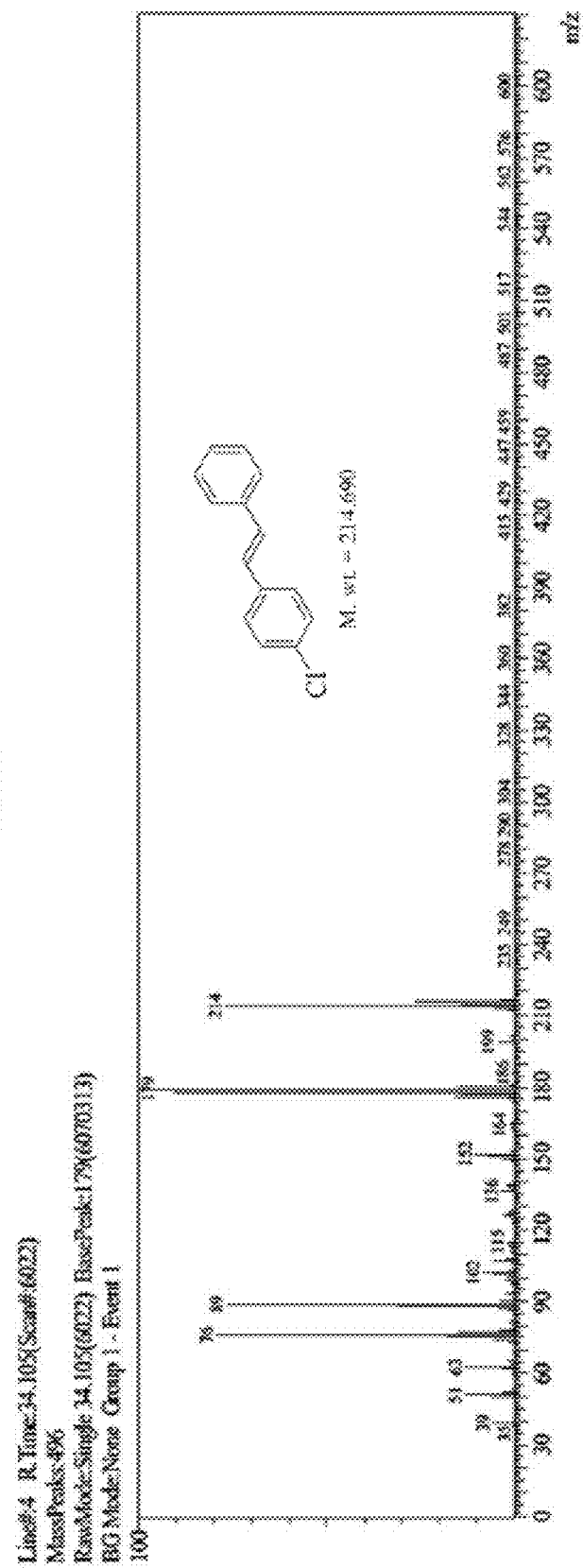
FIG. 51 is a mass spectrum of the Mizoroki-Heck coupling reaction product of 4-chlorostyrene.
Figure 52:
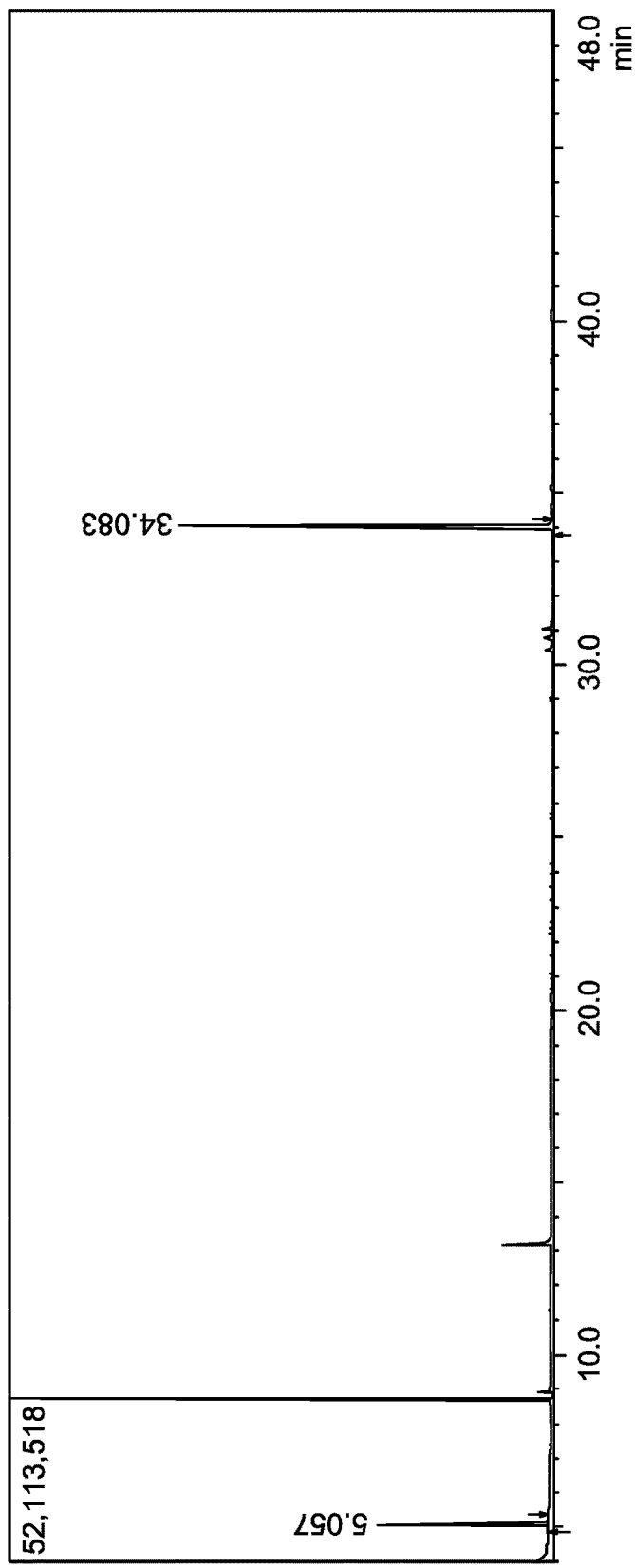
FIG. 52 is a gas chromatogram of the Mizoroki-Heck reaction product of 4-chlorostyrene and bromobenzene formed at 95° C. after 1 hour.
Figure 53:
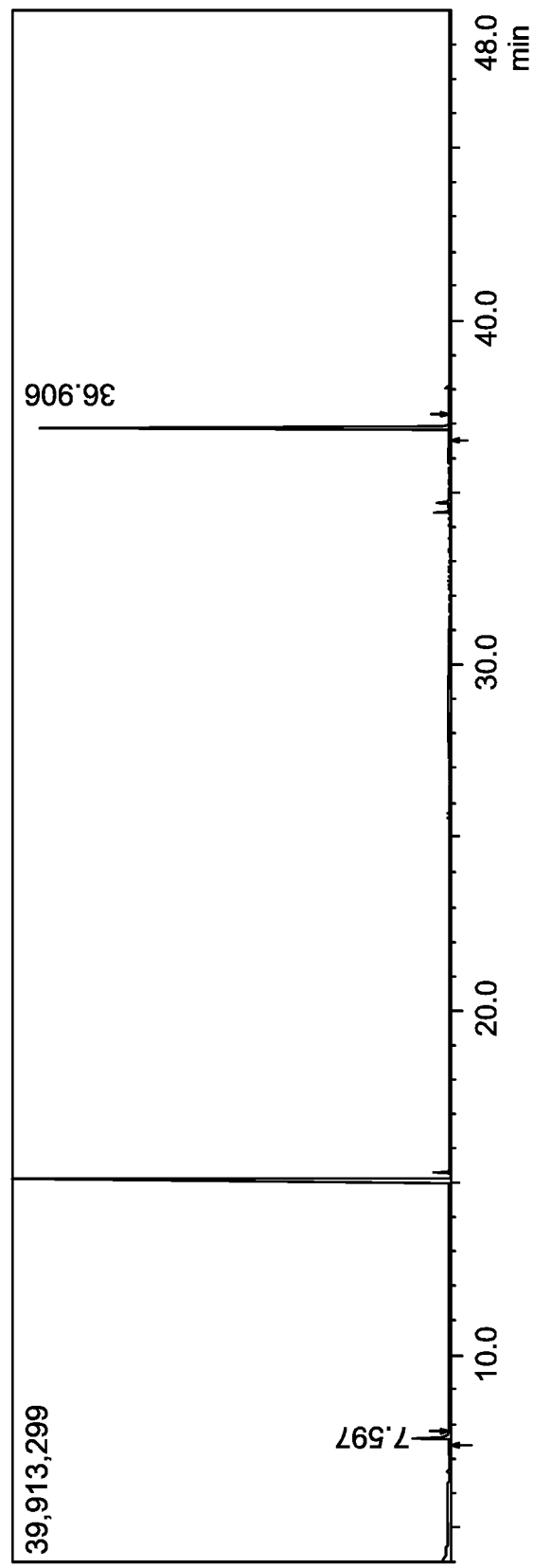
FIG. 53 is a gas chromatogram of the Mizoroki-Heck reaction product of 3-nitrostyrene and iodobenzene formed at 95° C. after 30 minutes.
Figure 54:
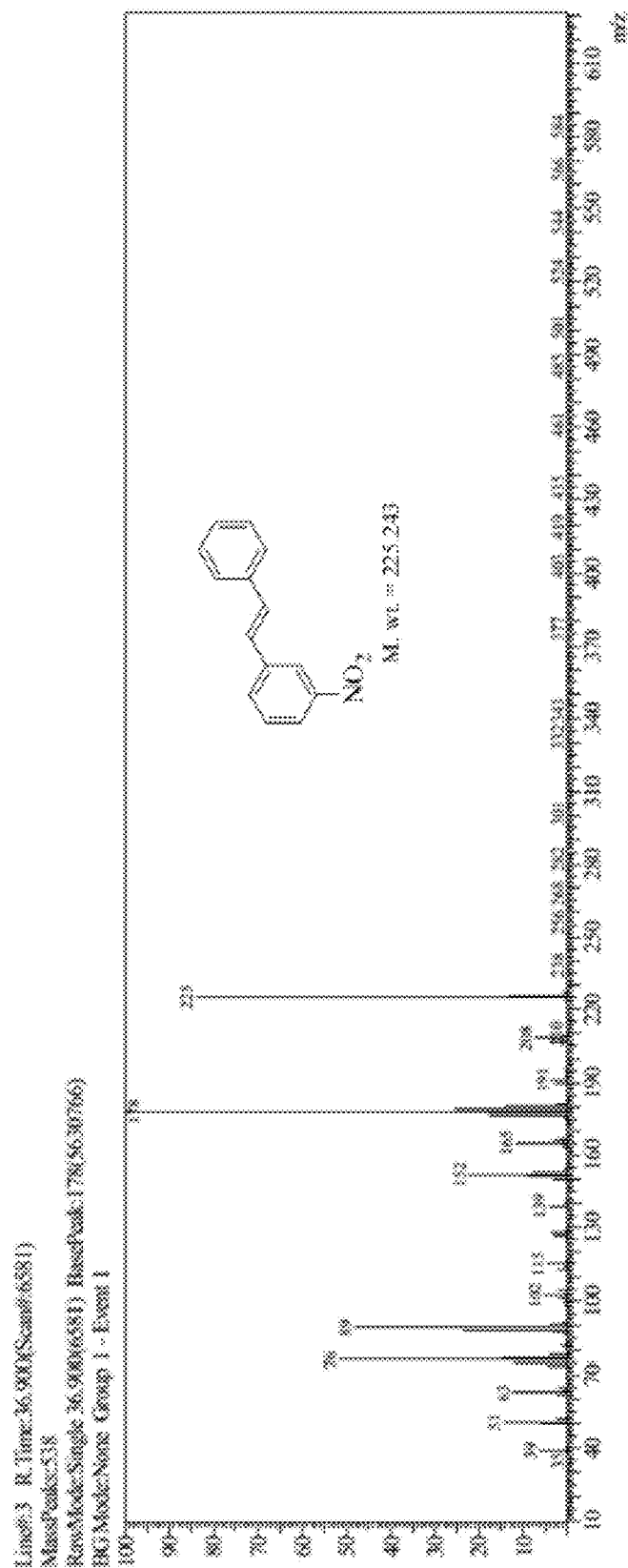
FIG. 54 is a mass spectrum of the Mizoroki-Heck coupling reaction product of 3-nitrostyrene.

FIGS. 1B, 1C, 1D, and 1E are the transmission electron micrographs of $Fe_3O_4$, $Fe_3O_4@$dop-BPPF, $Fe_3O_4@$dop-BPPF-Pd, and $Fe_3O_4@$dop-BPPF-Rh, respectively. The micrographs show that the nanoparticles are spherically-shaped and uniformly distributed. The average diameter was 6-8 nm. The high-resolution transmission electron micrograph and selected area electron diffraction (SAED) image are shown in FIGS. 1F and 1G, respectively. The interplanar distance was determined to be consistent with the literature data (T. Rajh, L. X. Chen, K. Lukas, T. Liu, M. C. Thurnauer, D. M. Tiede, J. Phys. Chem. B 106 (2002) 10543-10552, incorporated herein by reference in its entirety). The SAED data also revealed higher order crystallinity, which was further confirmed by the X-ray diffraction (XRD) signature of the nanomaterial. The peaks located at 30.22°, 35.70°, 43.10°, 53.40°, 57.10° and 63.20° indicate the formation of a nanocrystalline cubic (Fd3m) spinel $Fe_3O_4$ nanostructure (JCPDS card No. 01-075-0449) (N. Pinna, S. Grancharov, P. Beato, P. Bonville, M. Antonietti, M. Niederberger, Chem. Mater. 17 (2005) 3044-3049, incorporated herein by reference in its entirety). Therefore, coating the nanoparticles with dop-BPPF followed by complexation with Pd/Rh did not alter the original crystal structure of the parent compound ($Fe_3O_4$). Qualitative and quantitative phase analyses were carried out using the Rietveld method. The XRD patterns were refined by the Rietveld method (see FIGS. 12A, 12B, 13A, 13B, 14A, 14B, 15A, and 15B) and confirmed the formation of a single phase (the goodness fit factor was close to 1) (see Table 1). The calculated crystallite size was determined to be approximately 8.5 nm for all of the samples, which was in good agreement with the size obtained from TEM analysis. The calculated lattice parameter was approximately 8.36 Å, which was close to that of bulk magnetite. Elemental maps, as shown in FIGS. 3A-3D, indicate the uniform anchoring of the ferrocenylphosphine ligands and the complexed ligand with Rh and Pd on the surface of the nanoparticles. The presence of these elements was confirmed by the EDS results (see FIGS. 16A and 16B).

The Fourier transform infrared (FTIR) spectroscopic data revealed a vibration red shift of Fe-O by 7 nm from 583 nm for the parent magnetite with a bare surface. The characteristic aromatic C—H stretching at 2938 $cm^{-1}$ and aromatic C—C at 1428 $cm^{-1}$ confirmed the presence of dop-BPPF on the surface.

Figure 10:
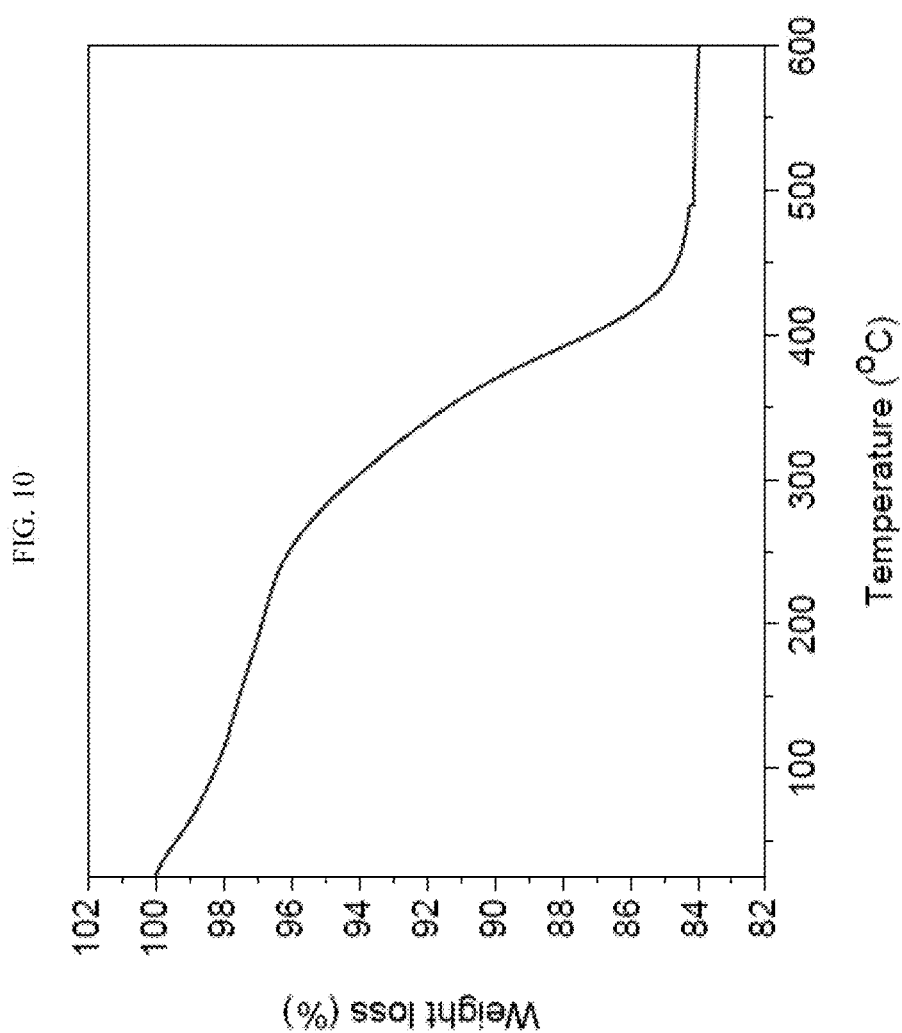
FIG. 10 is a thermogravimetry curve of $Fe_3O_4$@dop-BPPF under argon atmosphere.
Figure 11:
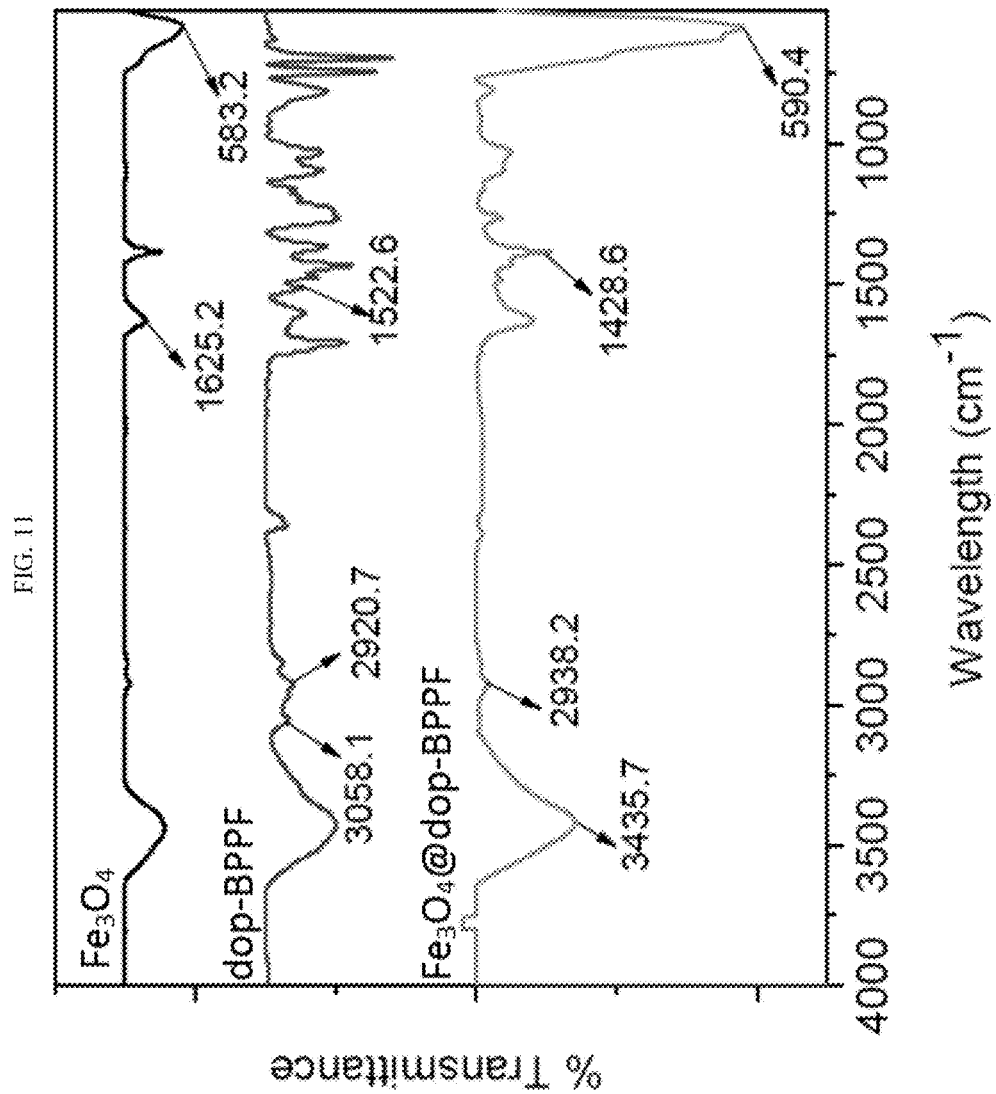
FIG. 11 is an overlay of FT-IR spectra of $Fe_3O_4$, dop-BPPF, and $Fe_3O_4$@dop-BPPF.
Figures 12A, 12B:
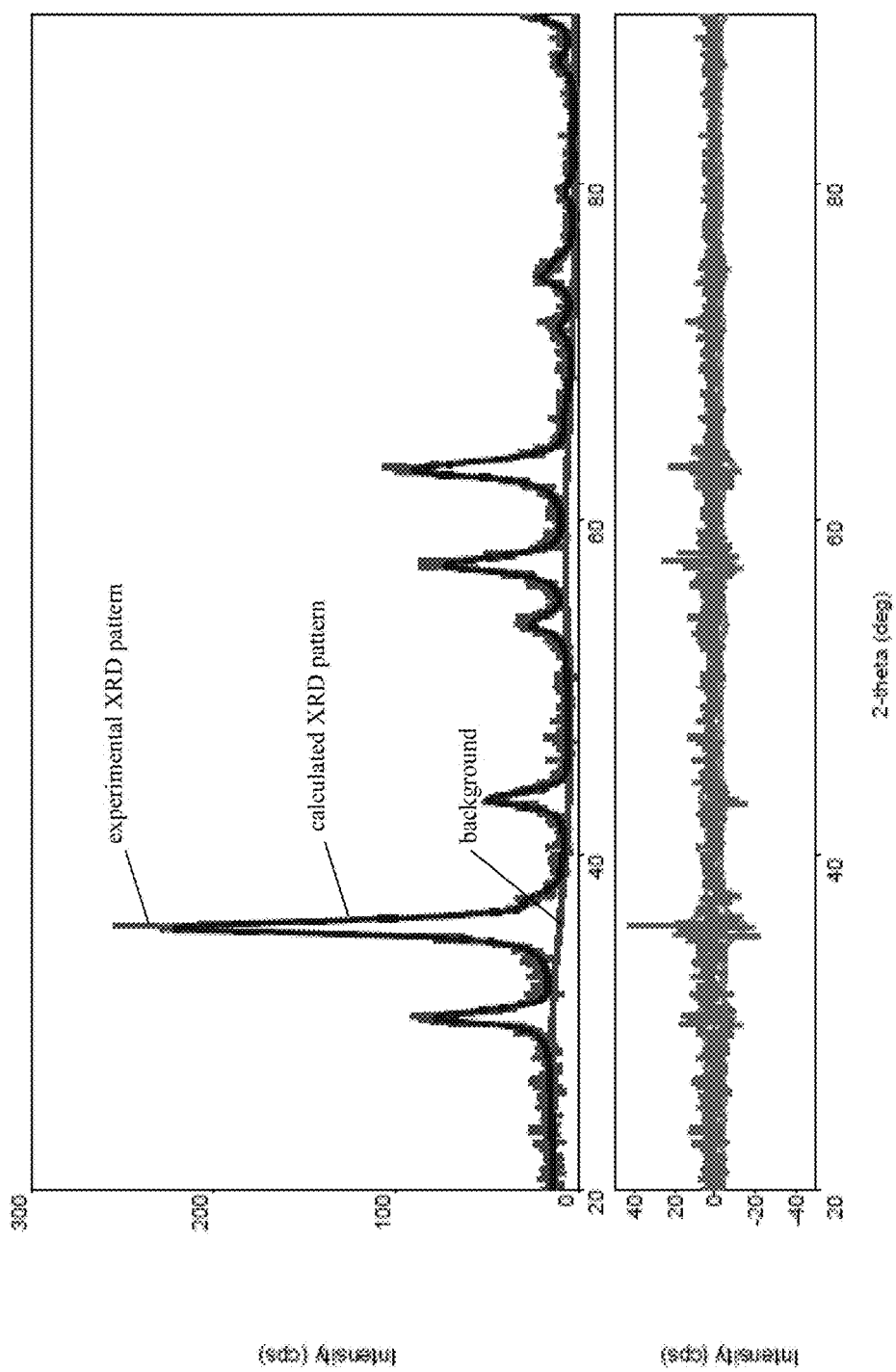
FIG. 12A is an overlap of the experimental and refined XRD patterns of $Fe_3O_4$.
FIG. 12B shows the difference between the refined and experimental XRD patterns of $Fe_3O_4$.
Figures 13A, 13B:
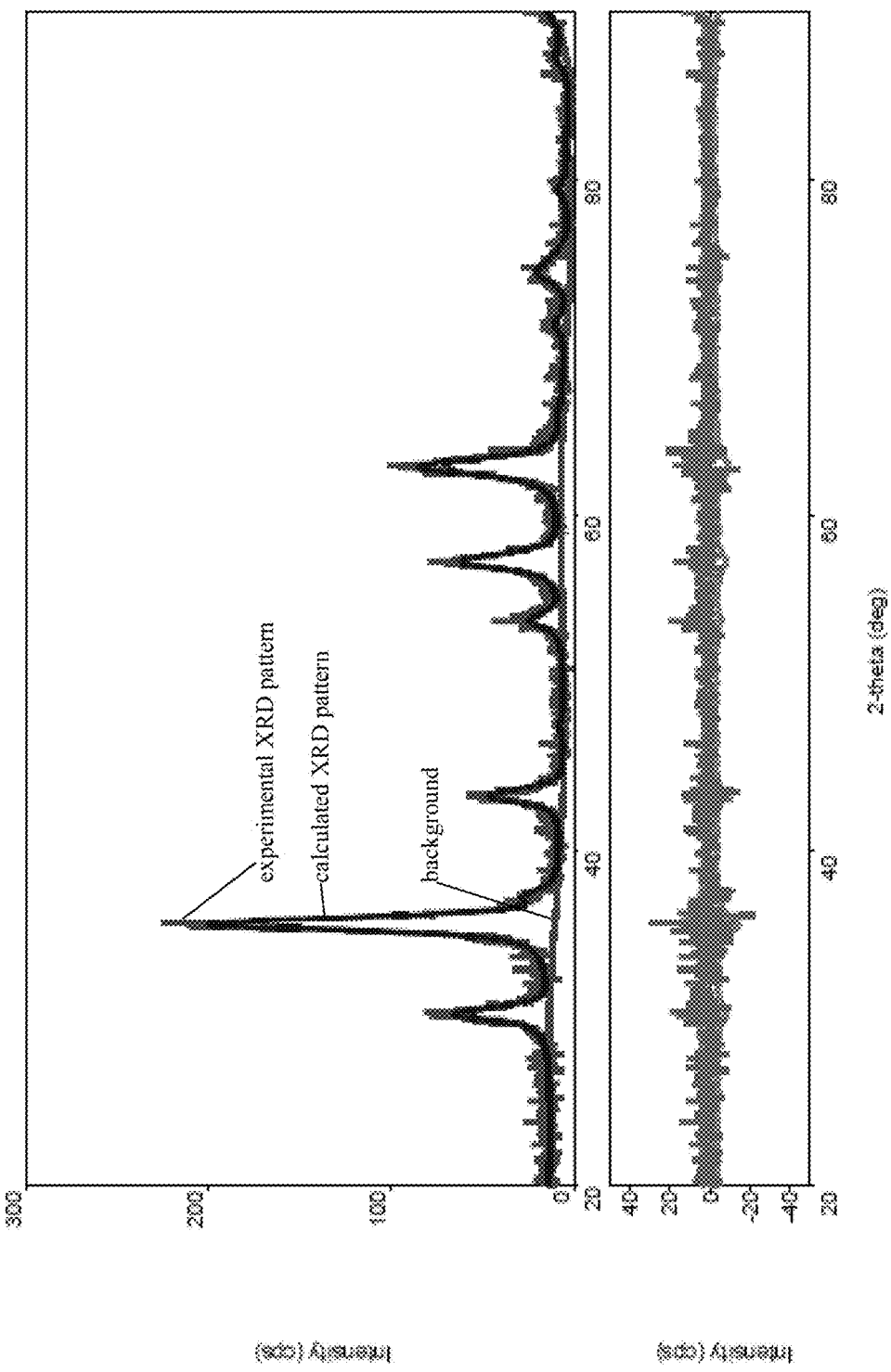
FIG. 13A is an overlap of the experimental and refined XRD patterns of $Fe_3O_4$@dop-BPPF.
FIG. 13B shows the difference between the refined and experimental XRD patterns of $Fe_3O_4$@dop-BPPF.
Figures 14A, 14B:
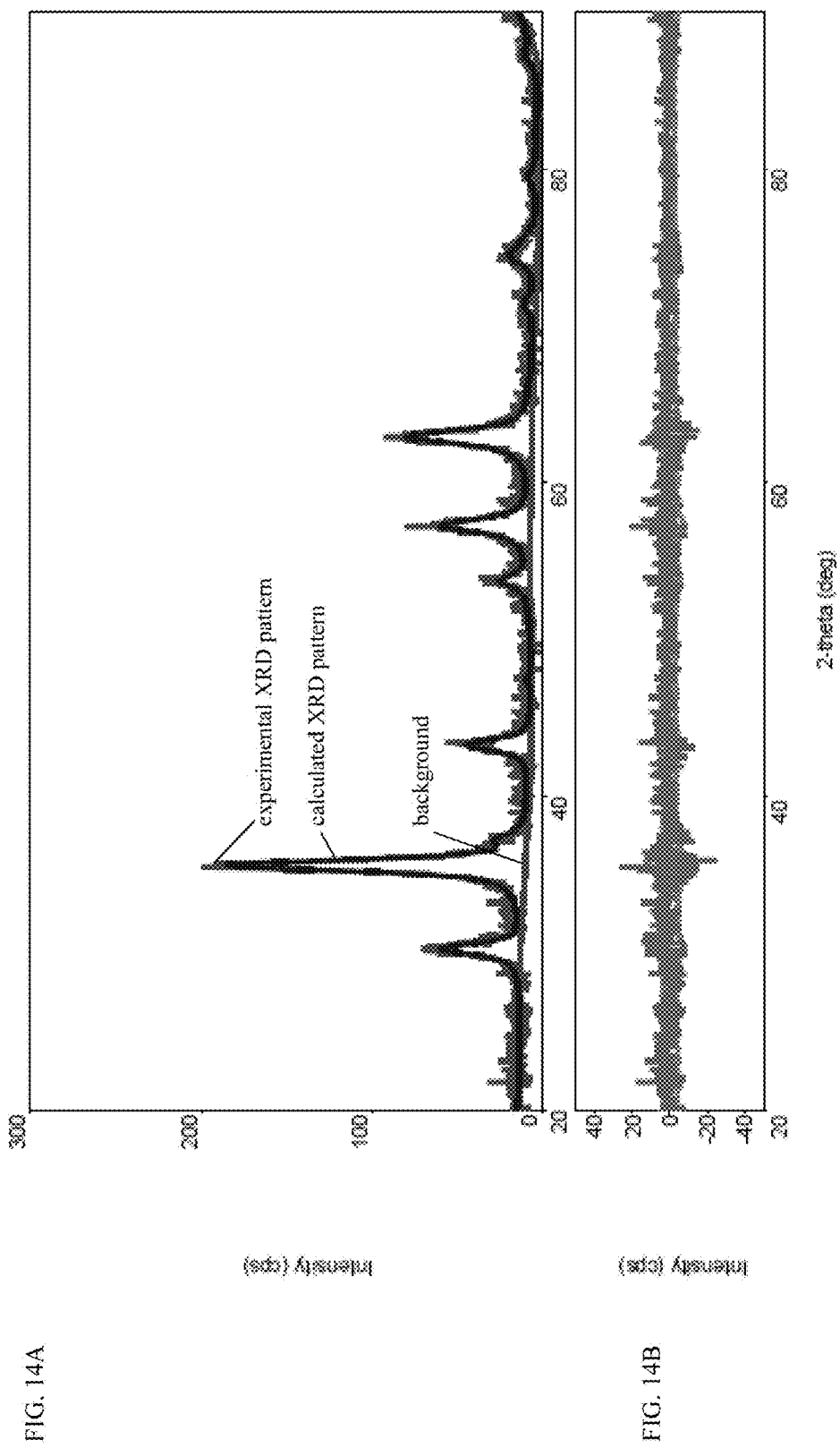
FIG. 14A is an overlap of the experimental and refined XRD patterns of $Fe_3O_4$@dop-BPPF-Pd.
FIG. 14B shows the difference between the refined and experimental XRD patterns of $Fe_3O_4$@dop-BPPF-Pd.
Figures 15A, 15B:
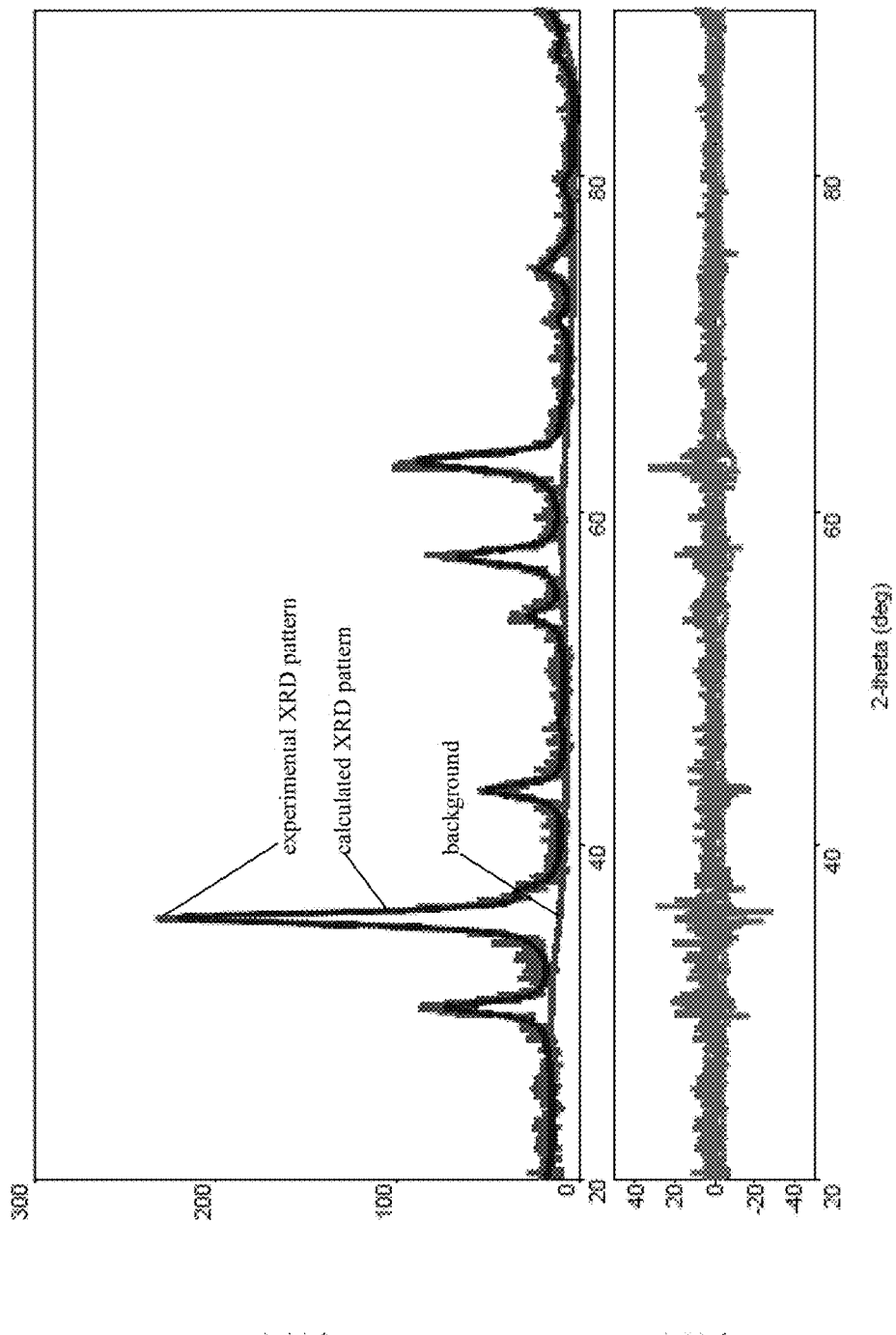
FIG. 15A is an overlap of the experimental and refined XRD patterns of $Fe_3O_4$@dop-BPPF-Rh.
FIG. 15B shows the difference between the refined and experimental XRD patterns of $Fe_3O_4$@dop-BPPF-Rh.

The thermal stability of dop-BPPF was investigated, and the stepwise weight loss profile was determined under an argon atmosphere in a temperature range of 25-600° C. (see FIG. 10). The amount of weight loss was determined to be approximately 14%, which indicated that the amount of loading on the nanoparticle surface was 0.2 mmol of dop-BPPF per gram of magnetic nanoparticles. These data were further confirmed by the amount of phosphine determined from the EDS results.

Figure 4A:
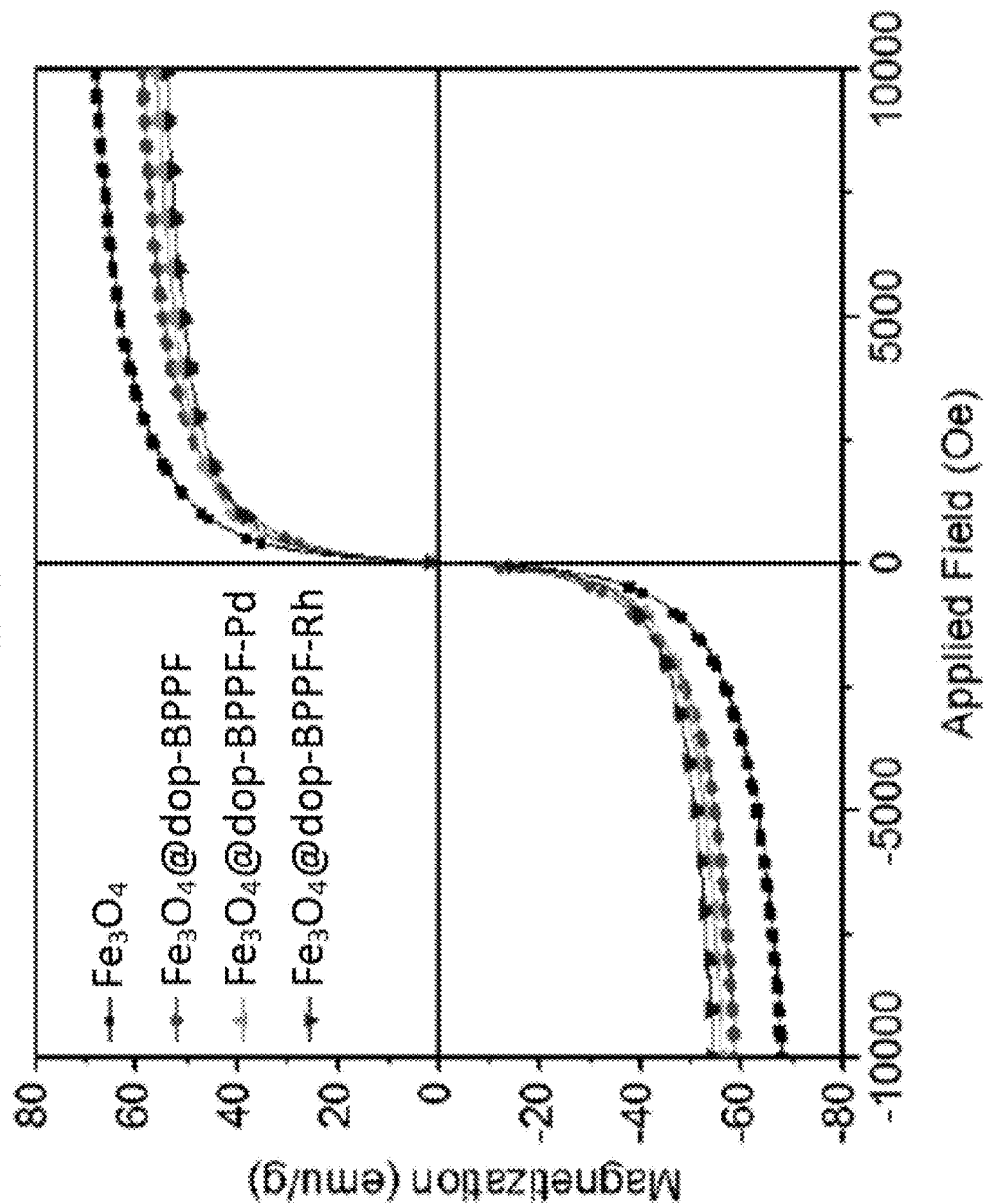
FIG. 4A illustrates the magnetic hysteresis loops of $Fe_3O_4$, $Fe_3O_4$@dop-BPPF, $Fe_3O_4$@dop-BPPF-Pd, and $Fe_3O_4$@dop-BPPF-Rh at room temperature with a 1 tesla magnet.
Figure 4B:
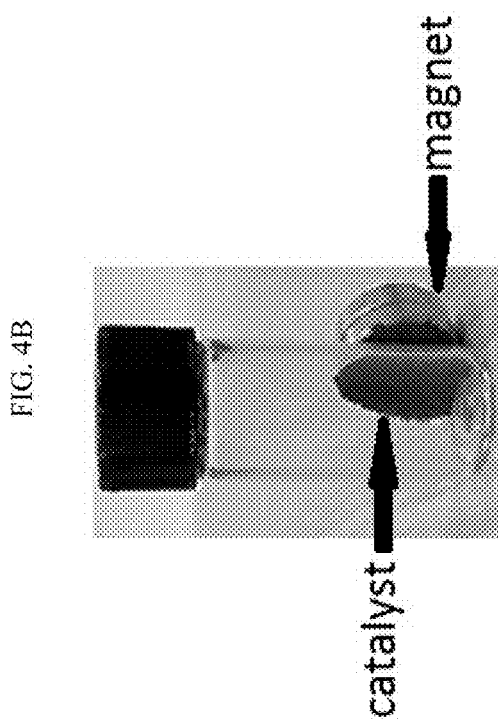
FIG. 4B shows the $Fe_3O_4$@dop-BPPF-Rh particles in the vial are attracted to the magnet placed outside the vial.

The recorded magnetic data revealed the superparamagnetic nature of all of the samples at room temperature (see FIG. 4A). Prior to coating, the magnetization of the bare surface of the magnetite ($Fe_3O_4$) was 67 emu $g^{-1}$, and the magnetization the surface-coated nanoparticles ($Fe_3O_4$@dop-BPPF) was 58 emu $g^{-1}$. The saturation magnetization value slightly decreased due to the coating with dop-BPPF and complexation with Pd and Rh. It is important to note that the coercivity (Hc) and remanence (Mr) were not affected by the surface functionalization and complexation processes. The coating of dop-BPPF and presence of Pd/Rh did not substantially affect the bulk magnetization, which is very important for the separation process, and these data were further confirmed by the physical use of a magnet near to the vial containing the particles (see FIG. 4B).

TABLE 1

Structural, microstructural of magnetite $Fe_3O_4$ before and after coating and complexation with Pd and Rh.

| | Crystallite size (nm) | Microstrain (%) | Lattice parameter (Å) | Goodness of fit |
|---|---|---|---|---|
| $Fe_3O_4$ | 8.4 | 0.360 | 8.372(4) | 1.0726 |
| $Fe_3O_4$@dop-BPPF | 8.5 | 0.478 | 8.365(4) | 1.1276 |
| $Fe_3O_4$@dop-BPPF-Pd | 8.6 | 0.500 | 8.363(4) | 1.1079 |
| $Fe_3O_4$@dop-BPPF-Rh | 8.4 | 0.340 | 8.359(4) | 1.1300 |

TABLE 2

Magnetic properties investigation data of magnetite $Fe_3O_4$ before and after coating and complexation with Pd and Rh.

| | Coercivity, $H_c$ (Oe) | Remanence, $M_r$ (emu/g) | Saturation magnetization, $M_s$ (emu/g) |
|---|---|---|---|
| $Fe_3O_4$ | 3.965 | 0.802 | 68.03 |
| $Fe_3O_4$@dop-BPPF | 4.322 | 0.645 | 58.75 |
| $Fe_3O_4$@dop-BPPF-Rh | 4.480 | 0708 | 56.00 |
| $Fe_3O_4$@dop-BPPF-Pd | 4.614 | 0.722 | 54.15 |

EXAMPLE 4 PROCEDURE FOR THE HYDROFORMYLATION REACTION

This reaction was carried out in a functional fume hood fitted with good suction. The functionalized magnetic nanoparticles, $Fe_3O_4$@dop-BPPF-Rh (50 mg), styrene (1.0 mmol, 0.12 mL) and freshly distilled THF (10 mL) were added to a Teflon-lined autoclave equipped with a pressure gauge and a mechanical stirrer under an argon atmosphere. Next, the inert atmosphere was replaced with a mild pressure release of $CO/H_2$ gas for three cycles. Then, the autoclave was pressurized with $CO/H_2$ (1:1) at 1000 psi, and the temperature was maintained at 45° C. After completion of the reaction, the pressure was released, and the sample was passed through a short silica gel column followed by injection into a gas chromatograph to determine the conversion and regioselectivity values.

The catalytic activity was evaluated using various substituted styrenes and n-alkenes at 45° C. with a mixture of carbon monoxide and hydrogen (1:1) under a pressure of 1000 psi. The results are shown in Table 3. A study on the reaction conditions was performed using styrene as a model substrate. At 45° C., 85% conversion of styrene to the corresponding aldehyde was achieved with a branched (B) to linear (L) ratio of 8:1 at 200 psi (entry #1). As the reaction temperature increased to 70° C., the yield improved but the regioselectivity was lost (entry #2). The solvent polarity played an important role in the selectivity. Based on the results in Table 1, a more polar solvent negatively affected the selectivity. Among all of the tested solvents, dichloromethane was the most efficient solvent for this reaction. For example, although a high selectivity (B:L=17:1) was obtained by employing a pressure of 1000 psi in THF at 45° C., a substantial improvement was observed when the same reaction was performed in dichloromethane, and the regioselectivity increased to 28:1 from 17:1 (entries #3 and 4) and to 52:1 from 14:1 (entries #6 and 7) for styrene and 4-methylstyrene, respectively.

Styrene substituted with different electron-withdrawing and -donating groups were used as substrates for the hydroformylation reaction. Although no noticeable change in the reactivity was observed, a profound effect was observed for the selectivity. The selectivity ratio for the branched to linear isomers of nitrostyrene and bromostyrene was 99:1 (entries #10 and 11). The hydroformylation of styrene under solvent-free conditions resulted in 86% conversion (entry #5) with 85% branched isomer. Thus, this system can be employed as a green catalyst in the hydroformylation reaction without the use of any organic solvents. For n-alkene, the reactivity of the catalyst was slow. The conversion of 1-octene (entry #14) reached 85% but the linear aldehyde was formed (B:L=0:100). This result was consistent with previously reported data. Also, no hydrogenated product was observed in the Rh-catalyzed hydroformylation.

The recyclability of the catalysts was investigated by employing the reaction conditions described herein. After the first round of catalysis, the nanocatalysts were washed with dichloromethane to remove any unwanted materials and reused for the 2$^{nd}$ round of catalysis without the addition of more Rh metal precursor. A gradual loss in the catalytic activity was observed after the 4$^{th}$ run, which may be due to the high pressure being employed in the reaction system, and the active catalyst was leached from the surface of the magnetic nanoparticles.

conversion was 50% (entry #1). In this reaction, the base played a crucial role in the regeneration of Pd active species. Therefore, $K_2CO_3$, $Et_3N$ and KOH were used in the DMF:$H_2O$ (1:1) solvent mixture, and the highest conversion was obtained using KOH (entry #2) compared to that using potassium carbonate or triethylamine (entries #3 and 4). The solvent effect was investigated by employing a series of

TABLE 3

Hydroformylation$^a$ of olefins using $Fe_3O_4$@dop-BPPF and [Rh(NBD)Cl]$_2$ metal precursor.

| Entry | Substrate | Time (h) | Pressure (psi) | Solvent | Temp (° C.) | Conv.$^b$ (%) | Branch. (B) | Linear (L) | Ratio (B:L) |
|---|---|---|---|---|---|---|---|---|---|
| 1 | Styrene | 9 | 200 | THF | 45 | 85 | 88.6 | 11.4 | 8 |
| 2 | Styrene | 10 | 200 | THF | 70 | 91 | 48.1 | 51.9 | 0.9 |
| 3 | Styrene | 8 | 1000 | THF | 45 | >99 | 94.5 | 5.5 | 17 |
| 4 | Styrene | 8 | 1000 | DCM | 45 | >99 | 96.4 | 3.6 | 28 |
| 5 | Styrene | 14 | 1000 | No solv. | 45 | 86 | 85.4 | 14.6 | 6 |
| 6 | 4-Methylstyrene | 14 | 1000 | THF | 45 | >99 | 93.4 | 6.6 | 14 |
| 7 | 4-Methylstyrene | 14 | 1000 | DCM | 45 | >99 | 98.1 | 1.9 | 52 |
| 8 | 4-Vinylanisole | 14 | 1000 | DCM | 45 | >99 | 97.2 | 2.8 | 35 |
| 9 | 4-Chlorosyrene | 12 | 1000 | DCM | 45 | >99 | 98.6 | 1.4 | 70 |
| 10 | 3-Nitrostyrene | 13 | 1000 | DCM | 45 | >99 | 99 | 1 | 99 |
| 11 | 2-Bromostyrene | 13 | 1000 | DCM | 45 | >99 | 99 | 1 | 99 |
| 12 | Vinylbenzoate | 16 | 1000 | DCM | 45 | 96 | | | |
| 13 | 1-Octene | 16 | 1000 | DCM | 45 | 85 | — | 100 | −100 |

$^a$1 mmol of styrene in 10 mL anhydrous solvent under syn gas (CO:$H_2$ 1:1) pressure using 50 mg of $Fe_3O_4$@dop-BPPF-Rh and Rh-metal precursor
$^b$determined by GC and identified by GC-MS;
nd: not determined

EXAMPLE 5 PROCEDURE FOR THE MIZOROKI-HECK REACTION

This reaction was performed in a reaction tube fitted with a magnetic stirrer and a Teflon stopper, and the reaction tube was in a parallel reactor. To a suspension of the catalyst, $Fe_3O_4$@dop-BPPF-Pd (50 mg), in DMF:water (1:1) (10 mL), styrene (1.0 mmol, 0.12 mL) and potassium hydroxide (1.0 mmol, 56 mg) were added. The temperature was maintained at 90° C. The progress of the reaction was monitored by a gas chromatograph, which was connected to a mass detector, and the product was extracted using ethyl acetate. The concentrated solution was passed through a short silica gel column and eluted with hexane:ethyl acetate (9:1).

In a study of the reaction conditions of the Mizoroki-Heck reaction, styrene and iodobenzene were chosen as the model substrates to evaluate the catalytic activity. The results are shown in Table 4. The effect of the temperature was investigated. A higher temperature was determined to be effective, which was confirmed by the results in entries #1 and 2. At 95° C., styrene was quantitatively converted to its corresponding product. However, at a lower temperature, the solvent systems, such as water, toluene, DMF, and DMF:water (1:1). The catalytic yield in pure water was only 67% (entry #5), which may be due to the insolubility of organic substrate in water and thus the substrate was not able to contact the metal reaction sites effectively. However, the DMF:water (1:1) mixture was a better solvent compared to that of pure DMF (entries #2 and 7).

TABLE 4

A study of the reaction conditions of the Mizoroki-Heck reaction between iodobenzene and styrene.

TABLE 4-continued

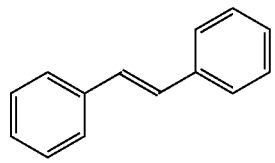 [SMILES: C(=C\c1ccccc1)/c1ccccc1]

| Entry | Base | Temp (° C.) | Solvent | Conversion[a] (%) |
|---|---|---|---|---|
| 1 | KOH | 60 | DMF-H$_2$O (1:1) | 50 |
| 2 | KOH | 95 | DMF-H$_2$O (1:1) | 99 |
| 3 | K$_2$CO$_3$ | 95 | DMF-H$_2$O (1:1) | 69 |
| 4 | Et$_3$N | 95 | DMF-H$_2$O (1:1) | 56 |
| 5 | KOH | 95 | H$_2$O | 67 |
| 6 | KOH | 95 | Toluene | 44 |
| 7 | KOH | 95 | DMF | 81 |

[a]Conversion measured after 30 minutes of reaction
Yields are based on iodobenzene;
[b]determined by GC and identified by GC-MS Using the reaction conditions described above, the coupling reaction was extended to a range of substituted styrene substrates to explore the scope of the newly developed catalytic system, and the results are summarized in Table 5. Bromobenzene was much less reactive with styrene than the corresponding iodobenzene (entries #1 and 2). However, prolonging the reaction time to 2-24 hours resulted in quantitative conversion. This result indicated the catalyst was stable for the extended reaction time. The electron-withdrawing group in the para and meta positions of styrene (entries #7-10) decreased the reaction rate. For example, using 4-chlorostyrene (entries #7 and 8), the maximum conversion was 69% after 24 hours, and the same trend was observed for 3-nitrostyrene (entry #10), which yielded 85% of the coupling product. Also, no biphenyl product was observed in the Pd-catalyzed Mizoroki-Heck reaction.

Figure 5:
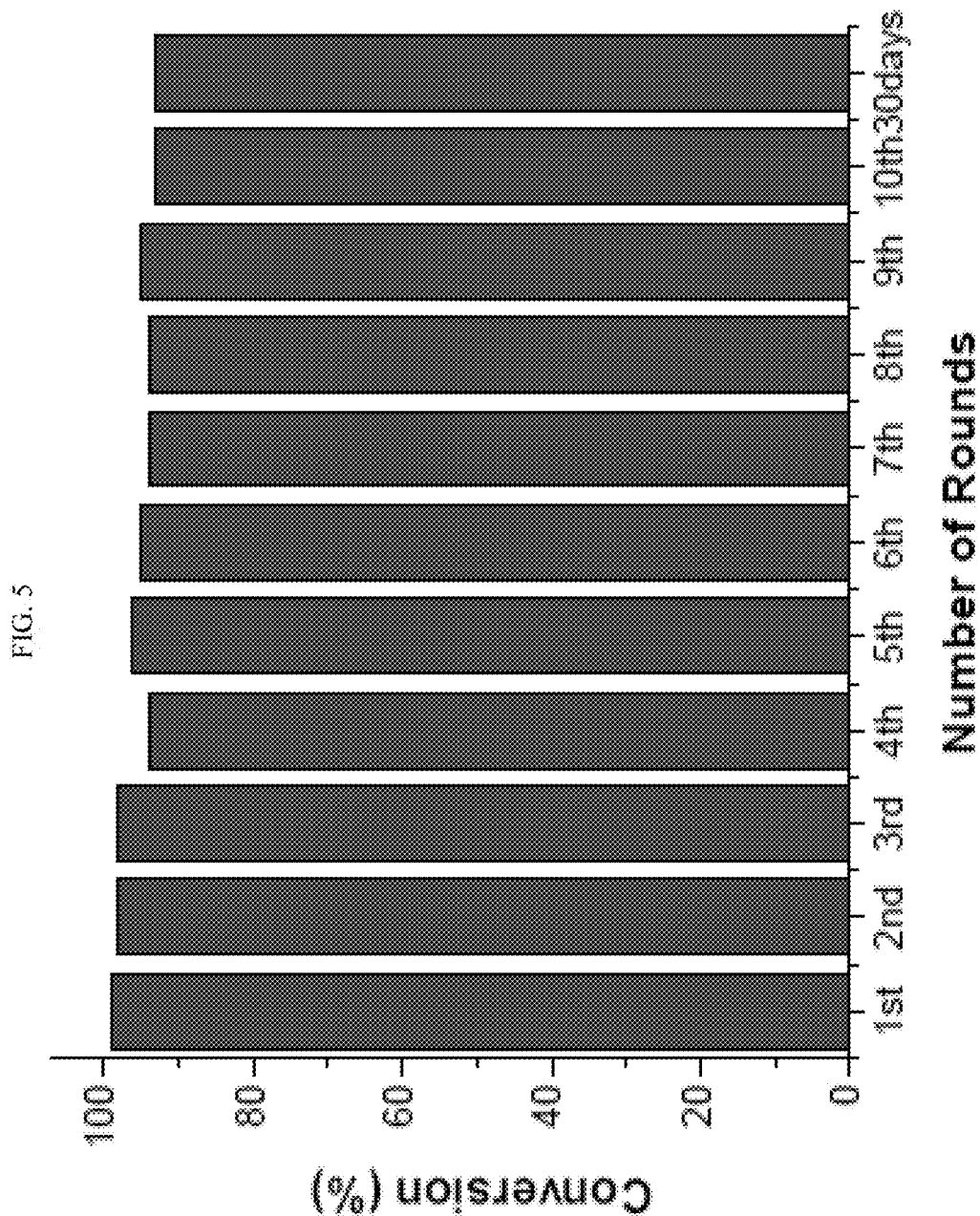
FIG. 5 is a graph illustrating the conversion of Mizoroki-Heck reactions catalyzed by a recycled catalyst.

The reusability of the nanocatalysts was investigated using the reaction of styrene and iodobenzene at 95° C., in a DMF:water 1:1 solvent mixture, and KOH base. The results are shown in FIG. 5 as a bar chart. After completion of the coupling reaction, the catalyst was collected by placing an external magnet at the bottom of the reaction vessel, and the solution was decanted for work up and gas chromatography. The collected catalyst particles were repeatedly washed with ethyl acetate and water prior to use in the next round of catalysis. The catalyst exhibited a consistent activity up to the 10$^{th}$ consecutive cycle after the reaction time was increased to 12 hours. Intrigued by its robustness, the collected catalysts from the 10$^{th}$ cycle were placed in the same coupling reaction for 30 days, and surprisingly, the observed loss of activity remained almost the same.

TABLE 5

A study of the reaction conditions for the Mizoroki-Heck reaction[a] between aryl halide and substituted styrene.

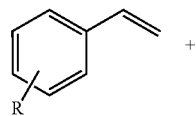

+

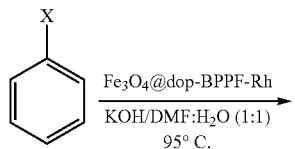

| Entry | Substrate (R) | Halide (X) | Time (min) | Conversion[b] |
|---|---|---|---|---|
| 1 | H | I | 30 | 99 |
| 2 | H | Br | 30 | 78 |
|   |   |   | 60 | 80 |
|   |   |   | 120 | 96 |
|   |   |   | 24 h | 99 |
| 3 | 4-CH$_3$ | I | 30 | 96 |
| 4 | 4-CH$_3$ | Br | 30 | 87 |
|   |   |   | 60 | 95 |
|   |   |   | 120 | 98 |
| 5 | 4-OCH$_3$ | I | 30 | 99 |
| 6 | 4-OCH$_3$ | Br | 30 | 77 |
|   |   |   | 60 | 94 |
|   |   |   | 120 | 96 |
| 7 | 4-Cl | I | 30 | 98 |
| 8 | 4-Cl | Br | 30 | 35 |
|   |   |   | 60 | 60 |
|   |   |   | 120 | 66 |
|   |   |   | 24 h | 69 |
| 9 | 3-NO$_2$ | I | 30 | 94 |
|   |   |   | 60 | 97 |
| 10 | 3-NO$_2$ | Br | 30 | 22 |
|   |   |   | 60 | 27 |
|   |   |   | 24 h | 85 |
| 11 | 2-Br | I | 30 | 96 |

[a]reactions were carried out at 95° C. in DMF:H$_2$O (1:1) using KOH as base and Fe$_3$O$_4$@dop-BPPF-Pd; yields are based on halobenzene;
[b]determined by GC and identified by GC-MS

The invention claimed is:

1. A magnetic nanoparticle functionalized with a ferrocenyl group, comprising:
   a complex represented by Formula (IIIA), Formula (IIIB), Formula (IVA), or Formula (IVB); and
   an iron(III) oxide nanoparticle;
   wherein the complex represented by Formula (IIIA) Formula (IIIB), Formula (IVA), or Formula (IVB) is:

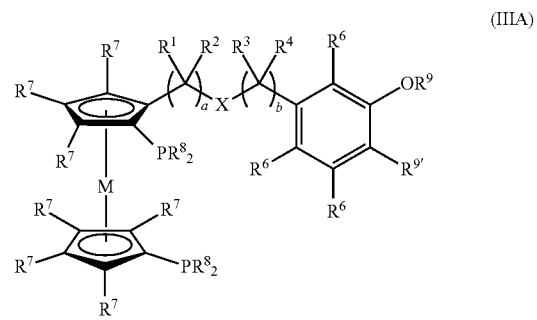

(IIIA)

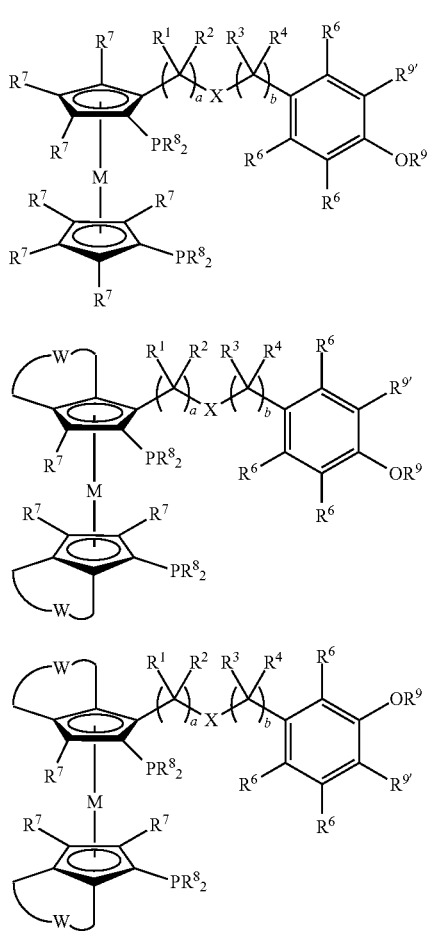

where each of $R^1$, $R^2$, $R^3$, and $R^4$ is independently a hydrogen, an optionally substituted alkyl, or an optionally substituted aryl;

each of $R^6$ and $R^7$ is independently a hydrogen, an optionally substituted alkyl, an optionally substituted aryl, an optionally substituted arylalkyl, an optionally substituted alkoxy, or an optionally substituted aryloxy;

each of $R^8$ is an optionally substituted alkyl, an optionally substituted aryl, or an optionally substituted arylalkyl;

$R^9$ is a single bond, a hydrogen, an optionally substituted alkyl, an optionally substituted aryl, or an optionally substituted arylalkyl;

$R^{9'}$ is a —O—, hydrogen, an optionally substituted alkyl, an optionally substituted aryl, an optionally substituted arylalkyl, an optionally substituted alkoxy, an optionally substituted aryloxy, or an optionally substituted arylalkoxy;

a and b are independently an integer in a range of 1-10;

X is O or NH;

M is iron;

W is an optionally substituted arylene; and wherein an oxygen atom in —$OR^9$ group in the complex represented by Formula (IIIA), Formula (IIIB), Formula (IVA), or Formula (IVB) is bound to a surface of the nanoparticle.

2. The magnetic nanoparticle of claim 1, wherein the nanoparticle has an average diameter in a range of 1-20 nm.

3. The magnetic nanoparticle of claim 1, wherein $R^1$ is an optionally substituted alkyl.

4. The magnetic nanoparticle of claim 1, wherein $R^8$ is an optionally substituted aryl.

5. The magnetic nanoparticle of claim 1, wherein the functionalized magnetic nanoparticle has a saturation magnetization in a range of 40-70 emu/g.

* * * * *